United States Patent
Popow et al.

(10) Patent No.: US 9,296,994 B2
(45) Date of Patent: Mar. 29, 2016

(54) ARCHEASE AS RNA LIGAES COMPLEX MEMBER

(71) Applicant: IMBA—INSTITUT FÜR MOLEKULARE BIOTECHNOLOGIE GMBH, Vienna (AT)

(72) Inventors: Johannes Popow, Vienna (AT); Javier Martinez, Vienna (AT); Anne Nielsen, Heidelberg (DE); Alexander Schleiffer, Vienna (AT); Theresa Henkel, Vienna (AT)

(73) Assignee: IMBA-INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 0 days.

(21) Appl. No.: 13/868,750

(22) Filed: Apr. 23, 2013

(65) Prior Publication Data

US 2013/0280763 A1    Oct. 24, 2013

(30) Foreign Application Priority Data

Apr. 23, 2012 (EP) .................................... 12165153

(51) Int. Cl.
- C12P 19/34 (2006.01)
- C12N 9/10 (2006.01)
- C07K 14/47 (2006.01)

(52) U.S. Cl.
CPC .......... *C12N 9/1007* (2013.01); *C07K 14/4705* (2013.01)

(58) Field of Classification Search
CPC .......... C07K 14/47; C12N 9/10; C12P 19/34; C12Q 2600/00
See application file for complete search history.

(56) References Cited

FOREIGN PATENT DOCUMENTS

| WO | 2012028606 | 3/2012 |
| WO | 2013119690 | 8/2013 |

OTHER PUBLICATIONS

Carrasco et al., "The Differentiation and Stress Response factor XBP-1 drives multiple myeloma pathogenesis", Cancer Cell, 11(4):349-360 (2007).
Fellmann et al., "Functional Identification of Optimized RNAi Triggers Using a Massively Parallel Sensor Assay", Molecular Cell, 41:733-746 (2011).
Fonseca et al., "Endoplasmic reticulum stress and pancreatic β-cell death", Trends in Endocrinology and Metabolism, 22(7):266-274 (2011).
Hassan et al., "Influenza A viral replication is blocked by inhibition of the inositol-requiring Enzyme 1 (IRE1) Stress Pathway", The Journal of Biological Chemistry, 287(7):4679-4689 (2012).
Papandreou et al., "Identification of an Ire1alpha endonuclease specific inhibitor with cytotoxic activity against human multiple myeloma", Blood, 117-1311-1314 (2011).
Popow et al., "HSPC117 is the Essential Subunit of Human RNA tRNA Splicing Ligase Complex", Science, 331:760-764 (2011).
Popow et al., "Diversity and roles of (t)RNA ligases", Cellular and Molecular Life Sciences, 69:2657-2670 (2012).
Walter et al., "The unfolded protein response: From stress pathway to Homeostatic regulation", Science, 334:1081-1086 (2011).
Yee et al., "An NMR Approach to Structural Proteomics", PNAS, 99(4):1825-1830 (2002).
Cao et al., "Combined proteomic-RNAi screen for host factors involved in human hepatitis delta virus replication", RNA, 15:1971-1979 (2009).
Canaves, Jaume M. "Predicted role for the archease protein family based on structural and sequence analysis of TM1083 and MTH1598, two proteins structurally characterized through structural genomics efforts", Proteins: Structure, Function, and Bioinformatics, 56:19-27 (2004).
International Search Report for PCT/EP2013/058374 dated Oct. 25, 2013, with Written Opinion.
Response to Non-Final Office Action in U.S. Appl. No. 13/760,920 filed Apr. 28, 2014.

*Primary Examiner* — Tracy Vivlemore
*Assistant Examiner* — Kate Poliakova-Georgantas
(74) *Attorney, Agent, or Firm* — Sughrue Mion, PLLC

(57) ABSTRACT

The present invention relates to the use of Archease proteins as RNA ligase enhancer, methods of ligating RNA molecules, kits for these methods and uses and transgenic cells.

Figure 2:
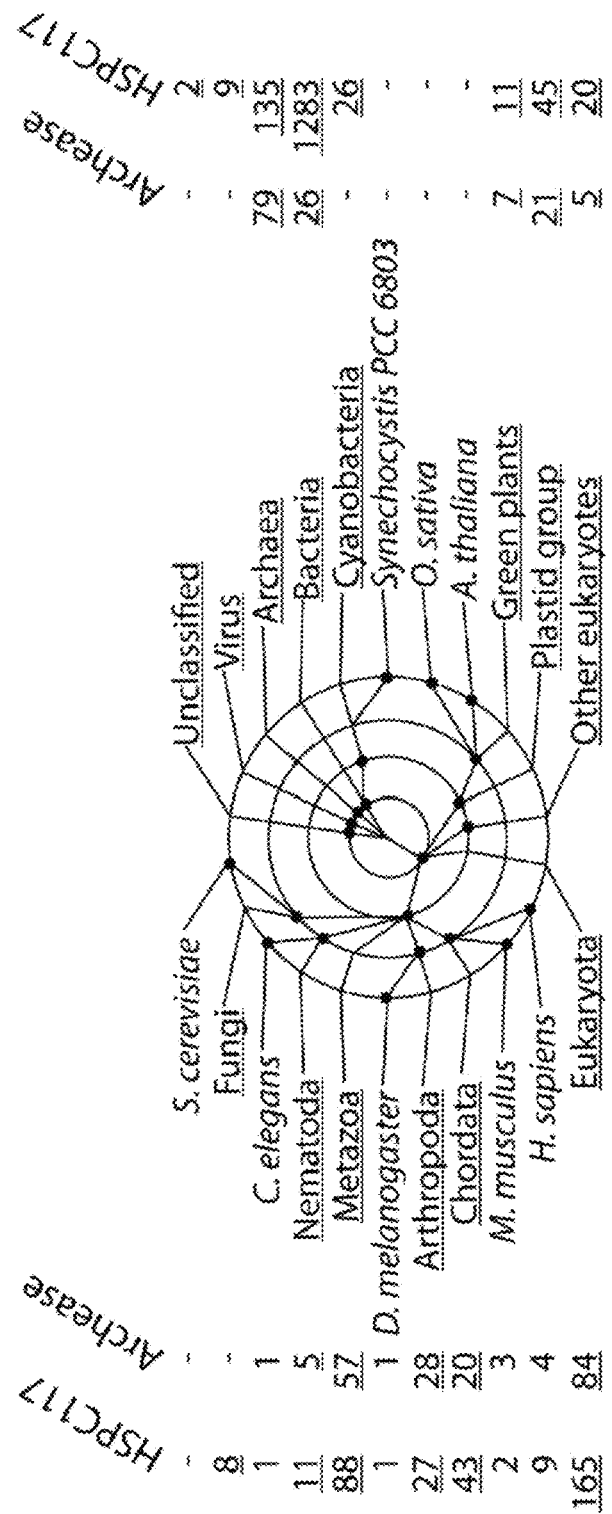

14 Claims, 16 Drawing Sheets
(9 of 16 Drawing Sheet(s) Filed in Color)

Figure 1
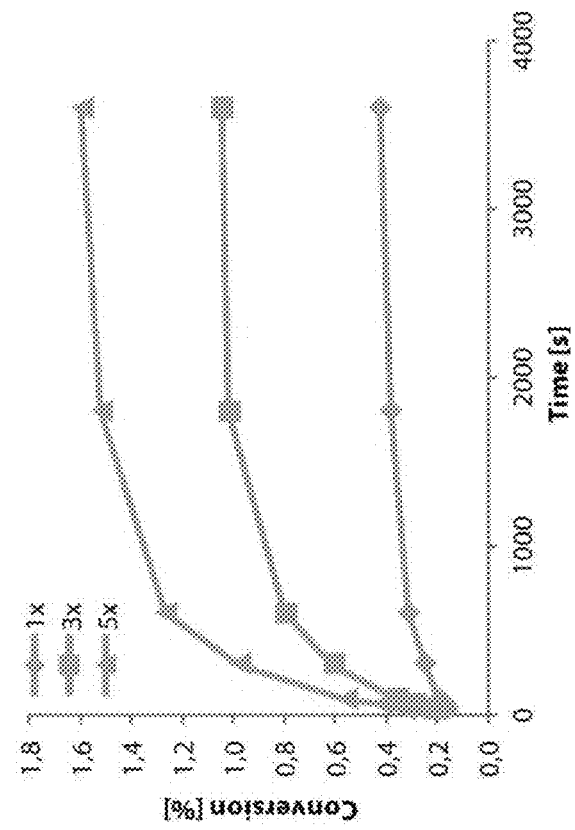
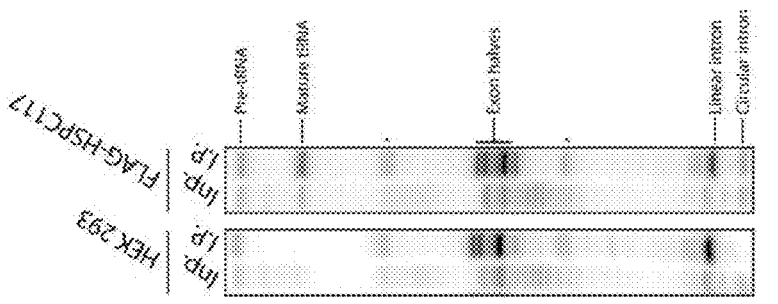
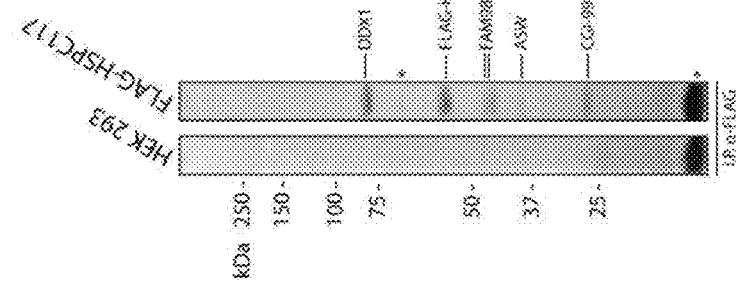

Figure 3
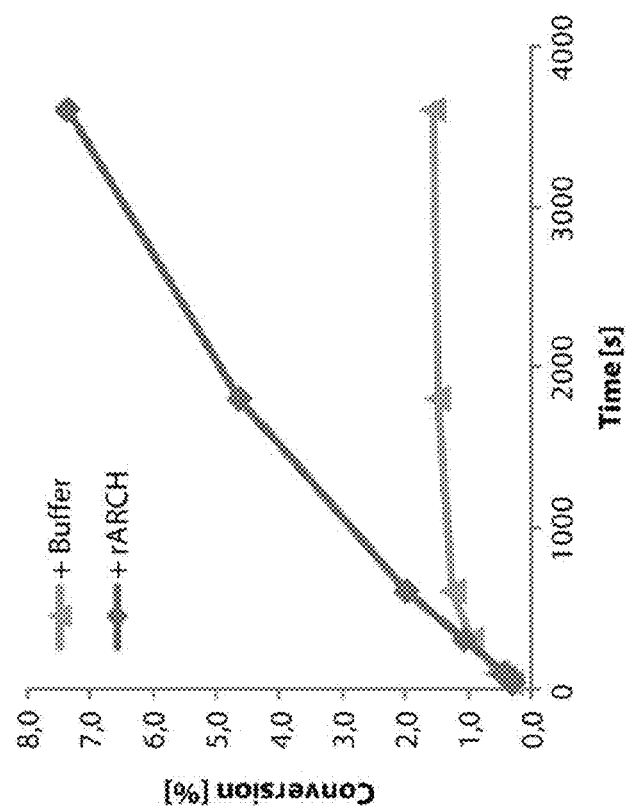
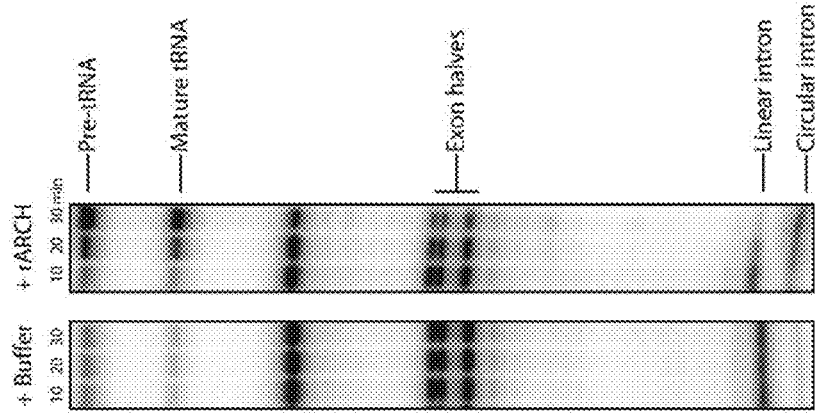

Figure 4
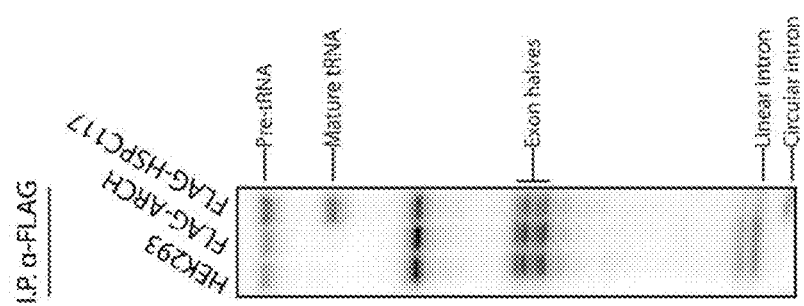
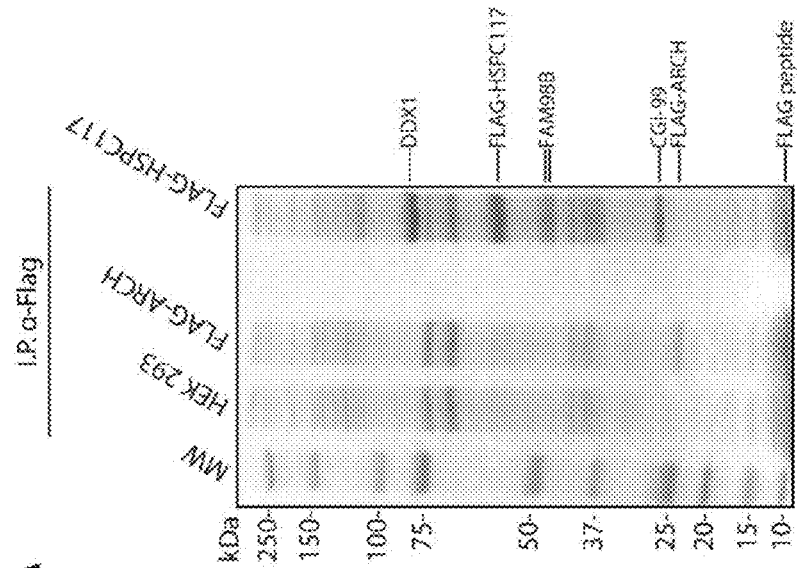

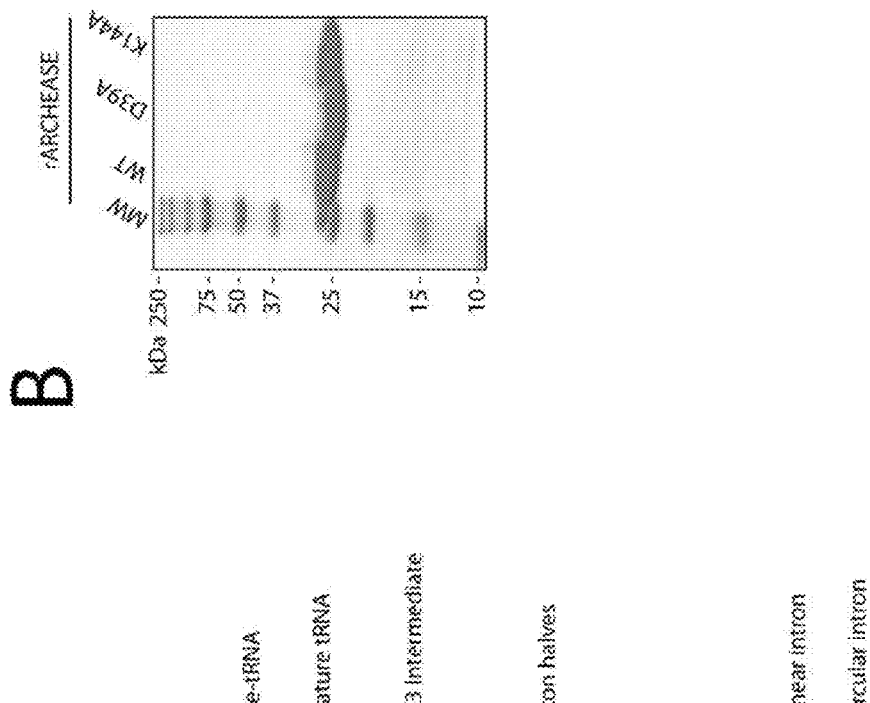
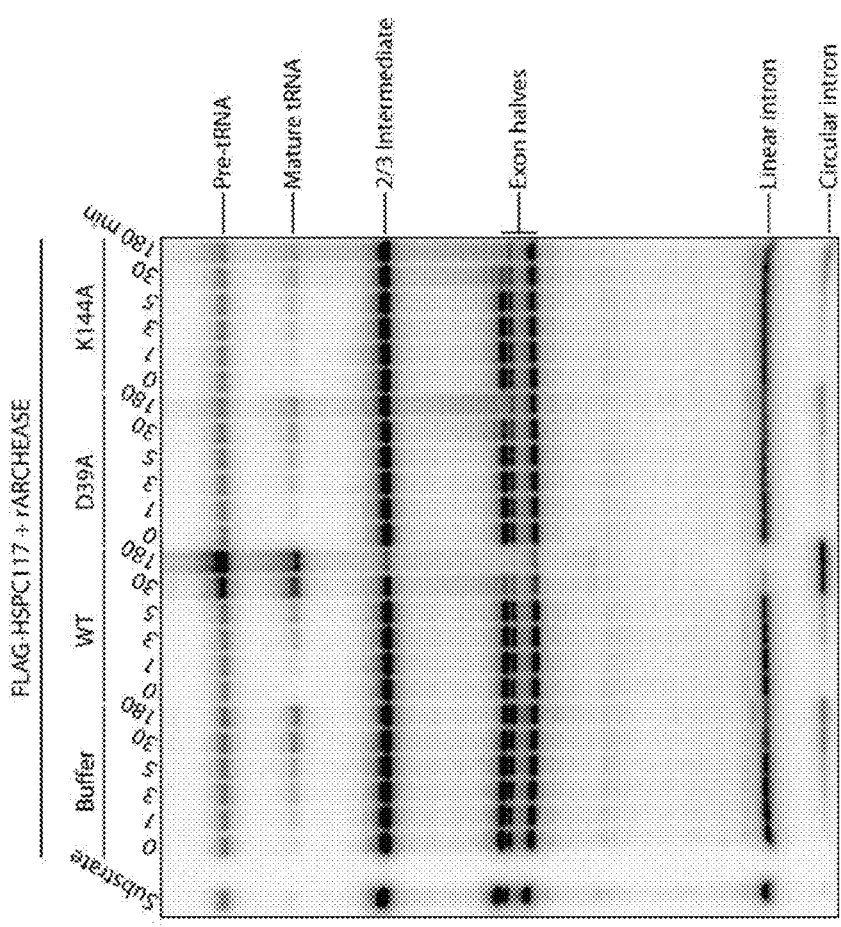
Figure 6

Figure 8
A
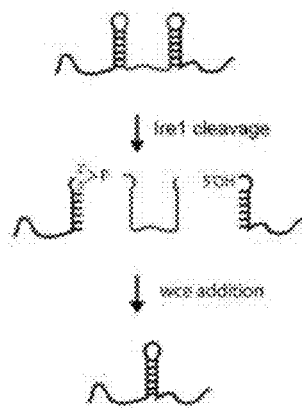
B
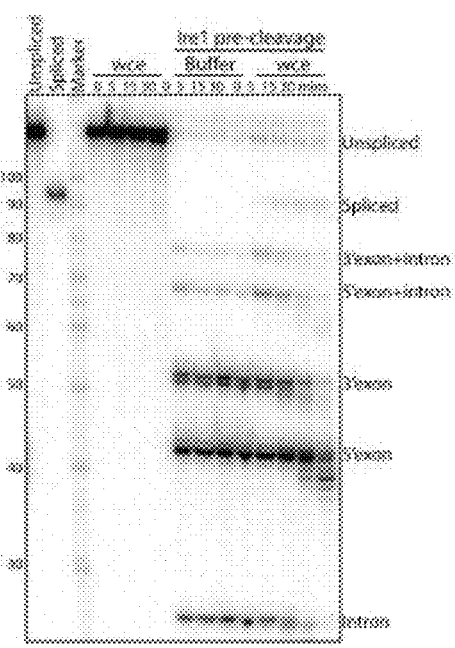
C
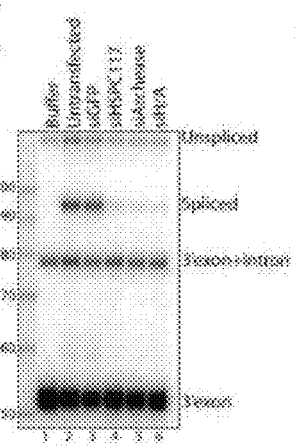
D
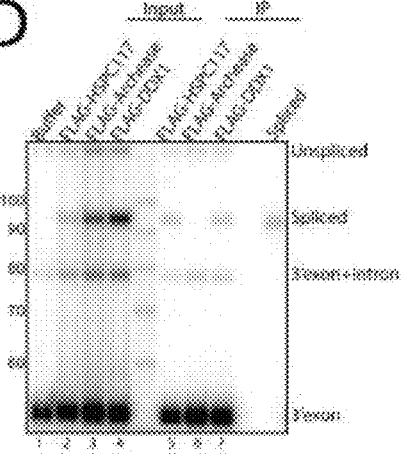
E
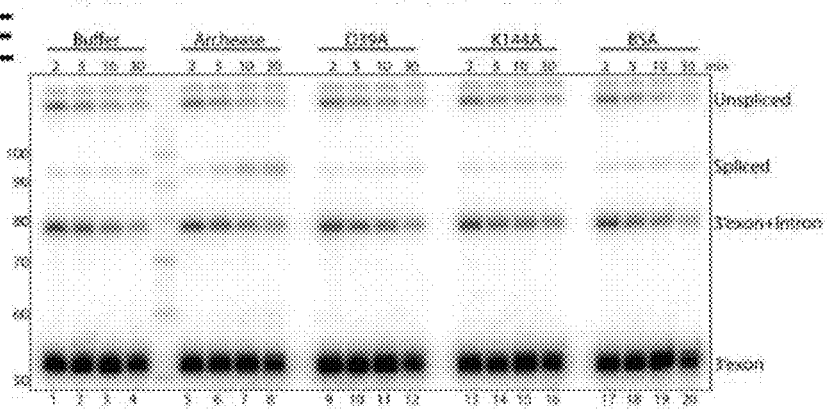

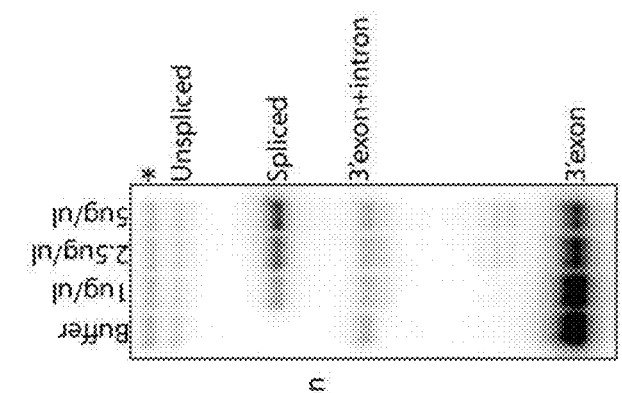
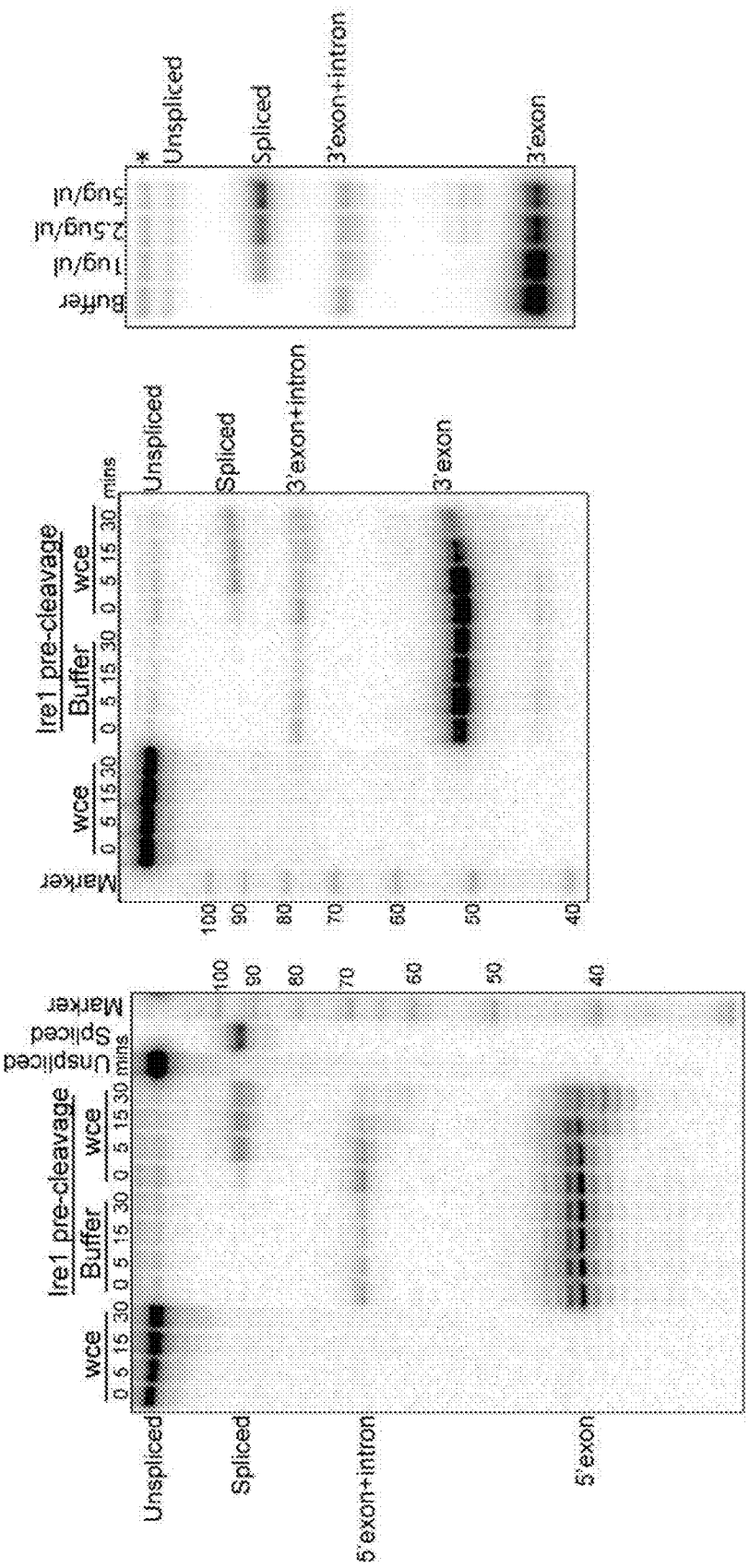

Figure 17
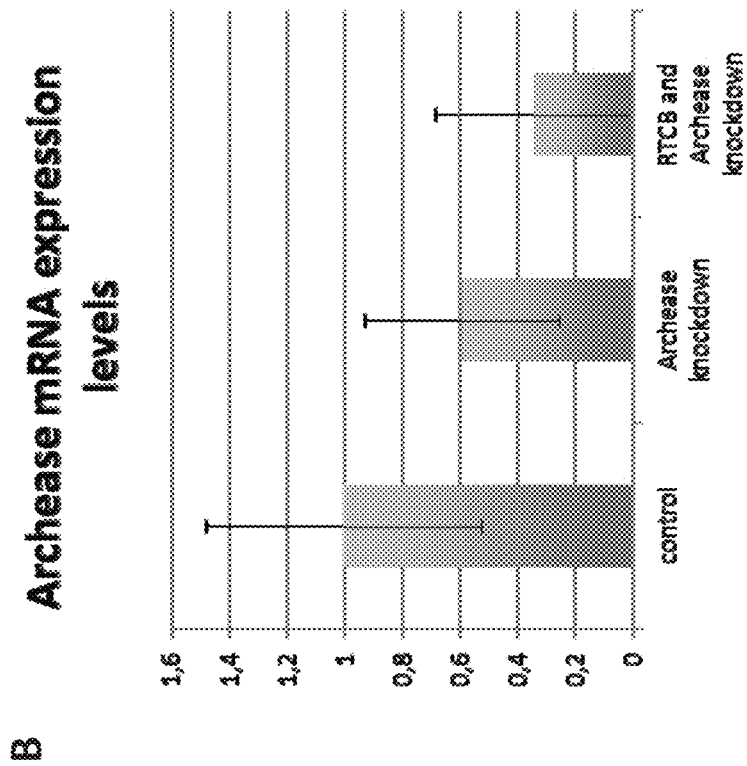
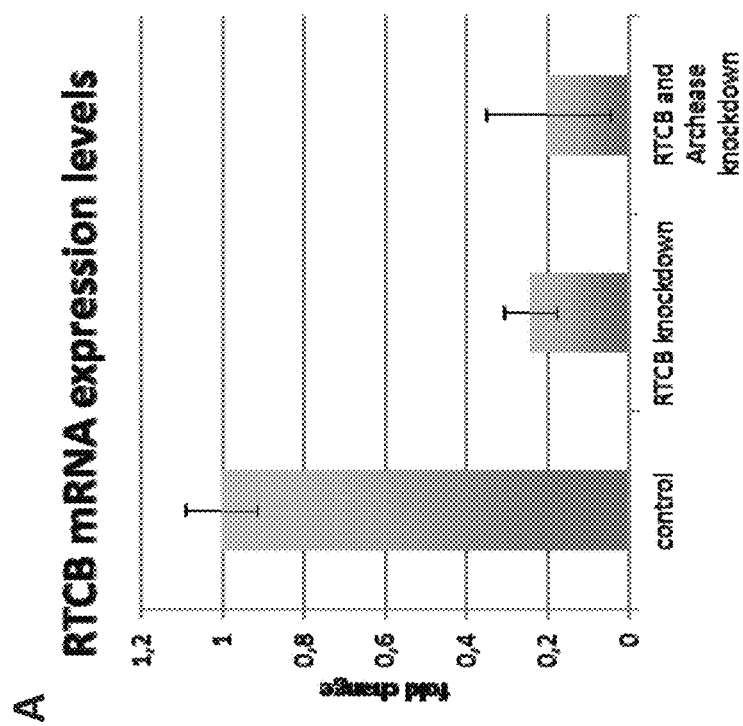

ARCHEASE AS RNA LIGAES COMPLEX MEMBER

CROSS-REFERENCE TO RELATED APPLICATION

This application relates to and claims the benefit of priority from European Patent Application No. 12165153.3, filed on Apr. 23, 2012, the entire disclosure of which is incorporated herein by reference.

The present invention relates to the field of cell and molecular biology tools, in particular to enzyme complexes with RNA ligase activity, said complexes or their parts for analysis and therapeutics.

The Endoplasmic Reticulum (ER) maintains homeostasis in protein folding, modification and secretion by sensing and responding to stress conditions leading to the accumulation of unfolded proteins in the ER lumen. The Unfolded Protein Response (UPR) signals from the ER to the nucleus through three stress-responsive signalling pathways in mammals. The most conserved UPR signalling pathway is initiated by Ire1, an ER resident transmembrane protein that responds to unfolded proteins in the ER lumen by dimerisation, autophosphorylation and activation of a cytoplasmic nuclease domain. Ire1 cleaves the mRNA encoding the transcription factor Xbp1 removing a 26 nt intron in the ORF. Religation of the exon halves by an unknown RNA ligase causes a frameshift, which allows translation to proceed past a stop codon. The resulting full-length protein (referred to as Xbp1s) moves to the nucleus and activates downstream target genes to help restore ER homeostasis.

In yeast, both tRNA splicing and non-conventional mRNA splicing during the UPR are executed by the tRNA ligase Trl1 through a 5'P dependent ligation pathway. This is possible because mRNA cleavage by Ire1 and pre-tRNA cleavage by the Sen endonuclease complex (TSEN) both generate 2'-3' cyclic phosphate and 5'hydroxyl termini amenable for Trl1. The mammalian tRNA ligase recently identified as a pentameric protein complex with HSPC117 as the catalytic component (Popow et al., 2011), required similar termini but ligates through a different mechanism.

Previously, the inventors have identified HSPC177 as RNA ligase (WO 2012/028606 A1). Splicing of several human pre-tRNAs requires the removal of introns and the ligation of the generated 5' and 3' exons by HSPC117 homologous proteins found in bacteria, archaea and vertebrates but generally not in plants and fungi.

It is a goal to identify ligases or their cofactors involved in non-conventional splicing induced by the Unfolded Protein Response (UPR), a stress response caused by misfolded proteins in cells, especially in the ER.

The present invention is based on the finding that Archease, while not being sufficient for splicing activity on its own, is required for efficient ligation of nucleic acids. Although ligases may be active on their own, Archease is able to strongly boost ligase activity. The invention thus provides the use of Archease for enhancing the ligase activity of a ligase enzyme. The invention also encompasses inhibition of Archease to reduce splicing activity, especially upon UPR, in a cell, which may cause cell death, e.g. by apoptosis or breakdown of cell metabolism, or reduction of cell growth or protein production. The invention is further defined by the subject matter of the claims.

Despite years of intense study, the identity of the ligation process in non-conventional splicing has eluded discovery in mammalian cells. While HSPC117 is the likely candidate for this splicing activity, it has been shown herein with certainty that ligation is dependent on Archease for stimulation of ligase activity. It is assumed that a few ligase complexes (possibly associated with the ER membrane) may suffice to induce non-conventional splicing upon induction of stress response as long as Archease is present to stimulate enzymatic rate.

Archease has been sequenced (e.g. Genbank ACC NO: NP_848642) and has been previously characterized as a protein with two SHS2 domains with one inserted into another. It usually has a three layer beta-alpha-beta sandwich domain similar to those found in chaperones. Archease proteins form a cluster of orthologous genes (KOG4528) with no detectable representatives in the plant or fungal model organisms. As used herein the expression "Archease" or "Archease protein" refers to any homologous or orthologous molecule in this cluster which has now been identified to enhance ligase reactions, especially RNA ligase reaction of e.g. spicing ligases like HSPC117. Example sequences of such Archease proteins are given in FIG. 5 as SEQ ID NO: 24 to SEQ ID NO: 44. Most Archease enzymes share the catalytic residues corresponding to D39 and/or K144 of SEQ ID NO: 28.

The ligase enhanced by the Archease can be used to catalyze the transfer of a first polynucleotide to a second polynucleotide. The ends of both polynucleotides can be connected by the ligase. This connection is usually a covalent connection of a phosphodiester bond between both polynucleotides. In particular, one polynucleotide may comprise a 3' phosphate, in particular in form of a 2',3'-cyclic phosphate, and the other may comprise a 5'-OH terminus.

In general, the polynucleotide ligation can be an inter- or intra-strand ligation. Two separate polynucleotide strands may be connected on the 3' and 5' end, respectively. Furthermore, in an intra-strand ligation, the 5' and 3' end of one polynucleotide molecule is connected.

In a further embodiment of the present invention the polynucleotide is double-stranded. In particular, the first and/or second polynucleotide molecule connected by the ligase enhanced by the Archease may comprise a double-stranded section or is fully double-stranded or alternatively single-stranded. In particular preferred, the 3' end mentioned above as well as the 5' terminus of the other polynucleotide end, which are connected by the ligase reaction, may be double-stranded. Further portions of the polynucleotide can also be single-stranded, in the case of RNA splicing there is usually a single-stranded 3' overhang of a pre-tRNA. Also, the 5' and/or 3' ends, which are connected by the ligase reaction may be single-stranded—as is usually the case in pre-tRNA processing. Double-strandedness may be a base pairing between the first and the second polynucleotide molecules, or alternatively may be base pairing to further polynucleotide strands.

In preferred embodiments the ligase is an RNA ligase. The first and/or second polynucleotide may be RNA. In particular preferred embodiments the present ligase enhanced by the Archease is used for RNA splicing. In an RNA splicing reaction an intron section is removed between two exons, which are connected by the ligase. A typical splicing reaction is the reaction of an exon1-intronexon2 sequence to exon1-exon2. Other splicing reactions may remove several introns and, optionally also exons between these intron sections.

The polynucleotides that are connected by the inventive use of the ligase may be of any length. Example polynucleotide lengths are 2 to 3000 nucleotides or base pairs in length. In special embodiments, the first polynucleotide or the second polynucleotide may be more than 1, 2, 3, 4, 5, 6, 7, 8, 9, 10, 15, 20, 25, 30, 40, 45, 50, 60, 70, 80, 90 or more than 100 nucleotides or base pairs in length. Alternatively or in addition thereto, the polynucleotide, either the first polynucleotide or second polynucleotide or both, may be up to 3000, 2000, 1500, 1200, 1000, 900, 800, 700, 600, 500, 400, 300, 200, 100, 80, 70, 60 or up to 50 nucleotides or base pairs in length.

In preferred embodiments the ligase enzyme is HSPC117. HSPC117 has been characterized previously as RNA ligase (WO 2012/028606 A1, incorporated herein by reference). The same definitions of HSPC117 molecules are used herein. In particular, the present invention relates to the use of a HSPC117 molecule as RNA ligase as a molecular biology tool and in therapeutics. HSPC117 has been sequenced (e.g. Genbank ACC NO: NP_055121 or CAG33456), and located at chromosome 22 orf 28 ("C220RF28"). HSPC117 is the human homolog of the bacterial/archaeal RtcB gene family characterised by a highly conserved domain of unknown function (UPF0027) and a unique protein fold. UPF0027 proteins form a cluster of orthologous genes (KOG3833) with no detectable representatives in the plant or fungal model organisms. This phyletic distribution is highly reminiscent of the exclusive occurrence of RNA>p ligase activity in animals and archaea. HSPC117 is also referred herein as HSPC117/C220RF28 or RtcB/HSPC117. As used herein the expression "HSPC117 molecule" refers to any homologous or orthologous molecule in this cluster which has now been identified to catalyze an RNA ligase reaction. Example sequences of such "HSPC117 molecules" are given in SEQ ID NOs: 1 to 11, 13, 15, 17, 19, 21, and 23. All HSPC117 molecules have been found to contain the catalytic cysteine residue corresponding to C122 of SEQ ID NO: 1.

In preferred embodiments, the HSPC117 molecule is set forth as in any one of SEQ ID NOs: 1, 2, 3, 4, 5, 6, 7, 8, 9, 10, 11, 13, 15, 17, 19, 21, or 23. The Homo sapiens HSPC117 is encoded by the mRNA sequence of SEQ ID NO: 46 (NCBI database accession number NM_014306) or by the coding sequence of SEQ ID NO: 12. The mRNA can be targeted by siRNA molecules for inhibition.

In preferred embodiments the inventive ligase, e.g. HSPC117, is of an animal or archaea, in particular of a mammal, such as a primate, including human, or rodent, in particular mouse or rat.

The inventive HSPC117 molecule may be further modified by one or more amino acid substitution or deletion. Furthermore, the inventive HSPC117 molecule may be expressed as part of a fusion protein and may comprise further additional amino acids or polypeptide sequences. In particular preferred, the inventive HSPC117 molecule has a sequence identity of at least 45%, 50%, 55%, 60%, 65%, 70%, 75%, 80%, 85%, 90% or at least 95% to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 17, SEQ ID NO: 19, SEQ ID NO: 21, SEQ ID NO: 23. In preferred embodiments the sequence identity is related to SEQ ID NO: 1. Sequence identities are usually calculated over the whole length sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 17, SEQ ID NO: 19, SEQ ID NO: 21, SEQ ID NO: 23. Of course such a HSPC117 molecule variant maintains the RNA ligase activity as mentioned above as can be easily determined by standard assays as known in the art, e.g. in WO 2012/028606 A1, or as shown in the example section herein. In particular of importance is that the HSPC117 molecule maintains catalytically important residues, such as cysteine 122 of SEQ ID NO: 1. Variants of the inventive HSPC117 molecules are e.g. described in US 2007/0204352 A1 (especially SEQ ID NOs: 15, 16, 69, 70, 71, 72, 73, 74, 75, 76, 77, 78 thereof), incorporated herein by reference as SEQ ID NOs: 12 to 23, and can be used for the inventive purposes.

Preferred Archease proteins are set forth as in any one of SEQ ID NOs: 24, 25, 26, 27, 28, 29, 30, 31, 32, 33, 34, 35, 36, 37, 38, 39, 40, 41, 42, 43, or 44. SEQ ID NOs: 24 to 43 are provided in an alignment in FIG. 5 with corresponding amino acids aligned to each other. SEQ ID NO: 44 is a further expression variant with 12 additional N-terminal amino acids of the Homo sapiens Archease of SEQ ID NO: 28. The Homo sapiens Archease is encoded by the mRNA sequence of SEQ ID NO: 45 (NCBI database accession number NM_178547). The mRNA can be targeted by siRNA molecules for inhibition.

Most Archease enzymes share the catalytic residues corresponding to D39 and/or K144 of SEQ ID NO: 28. Preferably the Archease comprises the sequence portion (E or D or V)-(I or V or P)-K-(A or S)-(V or I or P or M or A or L). Amino acid alternatives given in brackets; The K in said sequence portion corresponds to K144 of SEQ ID NO: 28. Alternatively or in addition, the Archease may comprise the sequence portion (D or E or P)-(H or T or I)-(T or P or M)-A-D-(I or V or A or L). Amino acid alternatives given in brackets; The D in said sequence portion corresponds to D39 of SEQ ID NO: 28. Such sequence portions are present in the sequences given in FIG. 5 for SEQ ID NO: 24 to 43, which are preferred forms of such sequence portions.

In preferred embodiments the inventive Archease is of an animal or archaea, in particular of a mammal, such as a primate, including human, or rodent, in particular mouse or rat.

The inventive Archease may be further modified by one or more amino acid substitution or deletion. Furthermore, the inventive Archease may be expressed as part of a fusion protein and may comprise further additional amino acids or polypeptide sequences. In particular preferred, the inventive Archease has a sequence identity of at least 45%, 50%, 55%, 60%, 65%, 70%, 75%, 80%, 85%, 90% or at least 95% to any one of SEQ ID NOs: 24, 25, 26, 27, 28, 29, 30, 31, 32, 33, 34, 35, 36, 37, 38, 39, 40, 41, 42, 43, or 44. In preferred embodiments the sequence identity is related to SEQ ID NO: 28. Sequence identities are usually calculated over the whole length sequences of SEQ ID NOs: 24, 25, 26, 27, 28, 29, 30, 31, 32, 33, 34, 35, 36, 37, 38, 39, 40, 41, 42, 43, or 44. Of course such an Archease variant maintains the ligase enhancing activity as mentioned above as can be easily determined by standard ligase assays as known in the art, e.g. in WO 2012/028606 A1, or as shown in the example section herein.

In the case of amino acid substitution (of both the Archease or the ligase), in preferred embodiments at least 50%, at least 60%, at least 70%, at least 80%, at least 90% or at least 95% of the substitutions are conserved amino acid substitutions. Conserved substitutions are mutations within an amino acid group. Amino acids are usually grouped according to their polarity, charge and/or size. The following groups are noteworthy: basic amino acids: arginine, histidine, lysine; acidic amino acids: aspartic acid, glutamic acid; polar amino acids: asparagine, glutamine; small amino acids: alanine, serine, threonine, methionine, glycine; aromatic amino acids: phenylalanine, tryptophan, tyrosine, histidine; hydrophobic amino acids: leucine, isoleucine, valine. Cysteine is a special case, as it may usually be conservatively substituted with serine and any other polar uncharged sidechain and vice versa. Glycine may be used as substituent for any amino acid.

Glycin can be substituted usually by a small sidechain such as by alanine, serine, threonine. Proline may be usually substituted, or used as substituent for glycin.

In a further aspect, the present invention relates to the method of ligating at least two polynucleotide molecules—as e.g. described above—using an Archease and a ligase as described above. Herein, the expressions "use . . . as ligase" and "method of ligating polynucleotide molecules" are used interchangeably.

In preferred embodiments the inventive use or method may comprise contacting at least two polynucleotide molecules with the ligase and the Archease in a cell. The invention also relates to the use of recombinant ligase and/or Archease. Recombinant ligase and Archease (including any homologs or orthologs as mentioned above) can be readily obtained by expression of genetic constructs comprising one or more ligase or Archease DNA sequences operable linked to regulatory DNA sequences (which may be heterologous regulatory sequences), such as promoters or enhancers, in host cells. Example host cells are bacterial, archaea, fungal (including yeast), plant or animal (including insect or mammalian) cells. In such constructs, the design of which is described in common laboratory manuals and is routine to a skilled practitioner, the regulatory sequences may be operably linked to a polynucleotide encoding the ligase or an active variant thereof having ligase activity and the Archease or an active variant thereof having ligase enhancing activity. Especially for but not limiting to in vitro purposes, the Archease and/or ligase may be provided in isolated and/or purified form.

The inventive Archease (and the ligase) may be used in vivo such as in a cell, e.g. artificially provided therein or recombinantly expressed in the cell. Two polynucleotide molecules may be ligated in said cell according to an embodiment of the present invention. The cell may be any cell as described above, preferably a non-human cell or an isolated human cell.

In a further embodiment the polynucleotide molecules may be contacted with a ligase and the Archease in vitro or in situ such as e.g. including outside a cell or in a cell free solution. With the inventive Archease and ligase it is possible to ligate polynucleotide molecules in an isolated fashion, ex vivo.

According to the present invention the Archease protein may be provided per se. Alternatively, Archease proteins may be used or provided as a component of a kit.

Thus, in a further aspect the invention relates to a kit that contains an Archease. The kit may further comprise a ligase reaction buffer comprising buffer components and one or more metal ions selected from $Mg^{2+}$, $Mn^{2+}$, $Ni^{2+}$ or mixtures thereof. In preferred embodiments the metal ions are included in an amount for use in a final concentration range of ca 0.1-20 mM, preferably 1-10 mM, in particular preferred 2-5 mM.

Besides the above-mentioned metal ions, the buffer of the kit may contain the usual buffer components that are well known in the art. Such buffers may e.g. include phosphate, Hepes, Tris-HCl components. Preferably the buffer is in the range of physiological pH values of e.g. pH 6 to pH 9, preferably pH 7-8, especially preferred about pH 7.4. The buffer may comprise tonic substances or salts ranging from about 10-200 mM KCl or NaCl. Furthermore, the buffer may contain non-ionic tonicity substances such as glycerol.

In the form of a test kit, the kit may further comprise a polynucleotide, especially a RNA molecule, that is a substrate of ligase enhanced by the Archease, especially a polynucleotide with a 2',3' cyclic phosphate. The kit may also comprise GTP, which is used by the Archease in guanylation reactions. This polynucleotide or the GTP may e.g. further comprise a label such as a radioactive label or fluorescent label to detect the polynucleotide molecule before or after the ligase reaction or to detect GTP binding to the Archease or to detect transfer of a G residue to a ligase.

The kit preferably comprises a ligase, especially preferred as described above, e.g. a RNA ligase such as HSPC117. Such a kit is useful for all types of reactions and to monitor polynucleotide processing or hybridisation. The inventive Archease or kit may be especially used for ligation or splicing studies or for obtaining Archease inhibitors, especially by the methods described below. The Archease may be immobilized for ease of phase separation and/or comprise a label. Said label may be used to immobilize the Archease. Example labels include a His-tag or a FLAG-label.

The present invention in a further aspect relates to a transgenic cell comprising an exogenously expressed Archease protein. The cell may be a cell line or comprised in an animal model, in particular a non-human animal model. A cell line may be also a human cell line that stably expresses Archease proteins.

Stable expression of the exogenously expressed Archease protein is achieved by inserting an Archease DNA, under the control of a promoter, preferably an inducible promoter, into the cell. In certain embodiments this DNA can be inserted in the genome of the cell, which can be achieved by conventional methods such as commercially available systems like the tetracycline-inducible system such as the t-REx system (invitrogen). Such cells are useful in combination with RNA that can be ligated, especially RNA with 2',3' cyclic phosphate or 5'-OH to ligate the RNA molecules.

The cell or cell line may further express an exogenously expressed ligase enzyme, e.g. as described above, preferably with an inducible promoter.

The present invention further relates to methods of reducing ligase activity, in particular RNA ligase activity, e.g. RNA>p ligase activity, in a cell comprising inhibiting a Archease molecule in a cell, preferably by knock-out or RNAi. RNA>p ligase activity, as mentioned above, relates to RNA ligase reactions using 2',3'-cyclic phosphate terminated RNA as substrate. Such a method can be used to reduce tRNA production or processing in said cell. Further or alternatively, such a method can be used to reduce Unfolded Protein Response (UPR) in a cell. A reduction of Archease can be achieved by administering a ligand to Archease that binds, segregates or generally inactivates Archease in said cell or by inhibiting Archease expression. Such a binding inhibitor is e.g. an Archease antibody, which is e.g. commercially available. An "Archease-antibody" includes any functional equivalents and derivatives thereof, including antibody fragments such as Fab, $F(ab)_2$, Fv, or single chain antibodies (scAb) that binds Archease. In preferred embodiments the inhibition is achieved by reducing expression of an Archease, preferably an endogenous Archease, in said cell. A suitable inhibitor to reduce Archease expression is an Archease siRNA molecule to induce RNAi.

Preferred methods of inhibiting Archease expression are knock-out or RNAi. For a knock-out, a genomic Archease is modified to prevent or reduce expression, transcription or translation of a functional Archease. Such modifications may include large stretch deletion of e.g. up to 200 or more nucleotides or selective modifications (deletions or substitutions) in the catalytic centre. E.g. a modification in the catalytic D39 and/or K144 according to the human Archease sequence of SEQ ID NO:28 is sufficient to prevent expression of a functional molecule. Of course the skilled man in the art can readily select alternative modifications, which are within the routine ability of a molecular cell biologist.

A further preferred method is RNAi (RNA interference). For antagonizing cellular Archease expression preferably siRNA molecules are administered to reduce the expression and function. RNA interference is a mechanism to suppress gene expression in a sequence-specific manner. RNA interference is a highly effective methodology for suppression of specific gene function in eukaryotic cells. When applied to cells and organisms, RNAi entails the degradation of target mRNA upon transfection of short interfering RNA (siRNA) oligos or short-hairpin RNA (shRNA) encoding vectors. Various methods of RNAi have been described and are generally known for altering gene expression in plant cells, *drosophila* and human melanoma cells as is described for example in US 2002/0162126 and US 2002/0173478. The siRNA for use in the methods and compositions of the invention are selected to target Archease. In this manner they are targeted to various RNAs or portions thereof corresponding to the Archease gene or mRNA (SEQ ID NO: 45). It is understood by one of skill in the art that the siRNA as herein described may also include altered siRNA that is a hybrid DNA/RNA construct or any equivalent thereof, double-stranded RNA, microRNA (miRNA), as well as siRNA forms such as siRNA duplications, small hairpin RNA (shRNA) in viral and non-viral vectors and siRNA or shRNA in carriers. Example siRNA molecules are provided as SEQ ID NO: 47 and 48 herein and are further commercially available.

In a further embodiment the invention relates to an Archease knock-out cell or cell with reduced or inhibited endogenous Archease expression.

In preferred embodiments said cell further has a knock-out of a ligase, e.g. RNA ligase like HSPC117, or reduced or inhibited expression of said ligase. Ligase inhibition can be performed similarly as described above for Archease, e.g. by knock-outs, inhibitor administration like anti-ligase antibodies or siRNA. siRNAs may target the ligase gene or mRNA, e.g. the mRNA of HSPC117 as set forth in SEQ ID NO: 46 or any homolog or ortholog variant thereof as expressed in said cell.

Such cell lines can be further used in polynucleotide ligation or splicing studies, i.e. to study the function of polynucleotide ligation. Further, the cell lines can be used to study UPR responses. In a transgenic cell wherein Archease is under control of an inducible promoter this allows specific on/off studies of the ligase enhancement and UPR responses and is a useful tool to control the ligase activity, be it only for splicing studies, for UPR studies or as a cellular biochemical engineering tool. Therefore, in a preferred embodiment, the invention relates to an Archease knock-out cell that does not express endogenous Archease but is in addition exogenously transfected with an Archease polynucleotide under control of an inducible promoter. In preferred embodiments the cell is a mammal cell, especially preferred a cell of a primate, in particular of a human or of a rodent such as a mouse cell. These cells, including cells with increased or decreased Archease expression as described above, can be used for ligation, splicing or UPR studies, in particular to identify inhibitors or enhancers of UPR that act on Archease.

Said cell may be in a non-human model animal, which may similarly be used to study Archease, ligase action, splicing and especially UPR in said animal. The animal may conditionally express Archease by using a suitable conditional promoter as known in the art. Thus the invention also relates to such model animals.

The inventive method of reducing RNA ligase activity in a cell comprising inhibiting an Archease in the cell, e.g. by knock-out or RNAi, preferably reduces the expression of Archease, preferably an endogenous Archease, in said cell. This method can be used to reduce the Unfolded Protein Response (UPR) in said cell.

The method may further comprise inducing stress in said cell, whereby unfolded proteins accumulate in said cell. Stress—be it by temperature increase, increased metabolism (such as in cancer cells) or by chemicals—can cause an increased production of proteins that are not properly folded. The UPR is activated in response to an accumulation of unfolded or misfolded proteins in the lumen of the endoplasmic reticulum. The UPR has two primary aims: initially to restore normal function of the cell by halting protein translation and activate the signaling pathways that lead to increasing the production of molecular chaperones involved in protein folding. If these objectives are not achieved within a certain time lapse or the disruption is prolonged, the UPR aims towards apoptosis. Thus the inventive Archease inhibition can be used to induce apoptosis in a cell. The inventive method or uses of Archease also include the prevention (or reducing the risk) of apoptosis in a cell due to unfolded protein accumulation, said method comprising increasing Archease protein amounts or expression levels in said cell, whereby an unfolded protein response in said cell is increased.

One of the primary functions of the ER is to exert quality control on the proteins it makes: Only properly folded proteins are packaged into ER exit vesicles and allowed to move onward to be displayed on the cell surface. For this purpose, the lumen of the endoplasmic reticulum (ER) provides an oxidative compartment wherein proteins destined for secretion or insertion into cellular membranes are co-translationally modified with sugar moieties and folded. Stresses that compromise the ER environment impair maturation resulting in the accumulation of misfolded proteins and activation of a stress response termed the unfolded protein response (UPR). Environmental stresses that reduce carbon source availability (glucose), and oxygen, which occurs under pathogenic conditions such as cancer and viral infection, also have a direct impact on secretory homeostasis and thereby trigger the UPR. During UPR, inhibition of protein synthesis serves to lower the overall rate of protein traffic into the ER, but the fact that this process is counterbalanced by an increased synthesis of ER chaperones highlights the specificity of the UPR.

Prolonged activity of the UPR, an indication that ER stress cannot be mitigated and homeostasis cannot be reestablished, correlates with cell death. This suggests that the commitment to apoptosis in this context may have evolved to protect the organism from rogue cells that lack the capacity to ascertain the fidelity of their signaling components. A life-or-death decision, based on an assessment of whether ER stress can be mitigated in a timely fashion, explains the UPR's central role in numerous human diseases. Examples include protein-misfolding diseases such as retinitis pigmentosa, an inherited form of blindness in which the retina degenerates by apoptotic cell death when a misfolded mutant rhodopsin is produced during retinal development. Another example is type II diabetes, in which pancreatic beta cells are compromised by excessive demand for insulin production. Certain types of cancer, especially those that arise in secretory tissues, such as multiple myeloma, use the cytoprotective role of the UPR to sustain their rapid growth.

In a further aspect the present invention relates to the treatment of diseases with abnormal tRNA processing or diseases dependent on (increased) tRNA processing. This treatment is tied to the ability of Archease to strongly modify the activity of RNA ligases like HSPC117. Moreover, the present invention relates to the treatment of diseases with causing a deficiency in UPR or diseases causing increased UPR or disorders associated with the UPR. The inventive treatment may not necessarily relate to a treatment in a curative sense but may also be a reduction of disease symptoms. The inventive treatment may also be a prophylactic treatment to reduce the risk of disease occurrence or symptom occurrences.

"Prevention" as used here shall not be construed as an absolute preventive effect but as a relative term, that is used to express the reduction of the risk of disease or disease symptom development. Treatments for prevention are prophylactic treatments.

In preferred embodiments the inventive treatment targeting Archease is combined with a treatment targeting an RNA ligase, like HSPC117. In preferred embodiments, Archease inhibition or inhibitors are combined with RNA ligase, e.g HSPC117, inhibition or inhibitors. In further embodiments, Archease enzyme activators are combined with RNA ligase, e.g HSPC117, activators. Such activators are e.g. the enzymes themselves or polynucleotides, e.g. vectors, encoding said enzymes.

In particular embodiments the invention provides the use of an Archease as an polynucleotide ligase enhancer or a method of inhibiting an Archease, with the proviso that methods for treatment of the human or animal body by therapy are excluded, or the use of an Archease or Archease inhibitor for use as medicament. An Archease inhibitor is any molecule that reduces Archease activity or expression as described above, preferably an Archease antibody or Archease siRNA.

It was found that Archease is required for the splicing of the Xbp1 mRNA. Archease thus has potential as a therapeutic target, for instance in the form of inhibitors to impair splicing (the case of multiple myeloma) or by enhancing Archease expression when UPR needs to be boosted. It is worth to note that, hitting the UPR pathway downstream of the endonuclease IRE1, more precisely at the ligation step, should not affect IRE1's mRNA decay function. Potent inhibitors of IRE1 have been identified as salicylaldehyde analogs (U.S. Pat. No. 7,858,666 and US 2009/0291857 A1).

In diabetes, the ultimate cell fate decision of life or death is dependent on the nature and severity of ER stress to which the β-cell is exposed. Thus, there are two types of ER stress conditions: resolvable and unresolvable. When ER stress can be resolved, the UPR promotes β-cell survival, whereas under unresolvable ER stress conditions, the UPR activates death effectors, leading to β-cell apoptosis. When β-cells are exposed to conditions that induce mild ER stress (e.g. physiological exposure to glucose fluctuations after a meal), the ER can facilitate stress mitigation and restore protein homeostasis, thus 'priming' cells for future ER stress insult and promoting cell survival. This situation also benefits from a more efficient UPR, which could be achieved by overexpressing a tRNA ligase (e.g. HSPC117) and/or Archease. Thus the present invention also provides a method of treating diabetes or preventing the risk of diabetes progression comprising administering an Archease agonist, e.g. an Archease enzyme or Archease encoding polynucleotide such as a suitable vector, to said patient. Preferably the Archease agonist is administered in combination with a HSPC117 agonist, e.g. HSPC117 or a HSPC117 encoding polynucleotide such as a HSPC117 encoding vector.

XBP1 has also been identified as a cellular transcription factor that binds to an enhancer in the promoter of the T cell leukemia virus type 1 promoter. Thus the invention also provides the treatment of T cell leukemia virus infections with an Archease inhibitor that reduced expression of XBP1 as shown herein. The generation of XBP1s during plasma cell differentiation also seems to be the cue for Kaposi's sarcoma-associated herpesvirus and Epstein Barr virus reactivation from latency. Thus the invention also relates to the treatment or prevention of these diseases with an Archease inhibitor.

A further disease condition which benefits from Archease activity is Alzheimer's disease. It is therapeutically beneficial to activate the UPR in such a way where neuronal cells survive the apoptotic effects due to unfolded aggregates of [beta]-amyloid protein. Thus the invention further includes the treatment of Alzheimer's disease with an Archease agonist as described above.

Diseases such as cancer, inflammation, and viral infection may be therapeutically modulated by inhibition of the UPR. In these types of conditions, cellular survival due to corruption of the UPR is impacted. Protein folding in the ER is negatively impacted by such conditions in the tumor microenvironment as hypoxia, glucose starvation, amino acid deprivation, acidosis and mutant malfolded and oncogenic proteins. Additionally chemo-, bio-, and radiotherapy can lead to protein folding stress. It is possible to induce apoptosis in these conditions by inhibiting the anti-apoptotic effects of the UPR. Myeloma derived from neoplastic antibody secreting plasma cells provides an example of a condition in which this approach can be applied.

Enveloped viruses must use and corrupt the UPR to ensure production of progeny from infected cells. Viruses often produce vast quantities of viral membrane glycoproteins which are folded and modified in the ER. Therefore, activation of the UPR by the virus for this purpose as a survival mechanism is common. It is therefore logical that inhibition of the UPR during viral infection can impact the outcome of the disease in a beneficial way.

Only specialized secretory cells and diseased cells activate the UPR for their own benefit. Most cells are not under such protein folding stress and therefore would not be impacted by a UPR inhibitor. Thus, "disorders associated with the UPR" as used herein means conditions for which pathogenesis can be advantageously impacted by inhibition of the UPR. In various embodiments of the invention such inhibition of the UPR is accomplished through inhibition of Archease.

In some embodiments, the Archease inhibitors are useful to treat or ameliorate a symptom of a B cell autoimmune disease, certain cancers, and infections of enveloped viruses that use the endoplasmic reticulum as a viral factory for expressing viral surface and spike proteins for budding and infection. Archease inhibitors can be used as single agents or in combination therapies.

B-cell autoimmune diseases which can be treated include, but are not limited to, Addison's disease, antiphospholipid syndrome, aplastic anemia, autoimmune hemolytic anemias, autoimmune hepatitis, autoimmune hypophysitis, autoimmune lymphoproliferative disorders, autoimmune myocarditis, Churg-Strauss syndrome, epidermolysis bullosa acquisita, giant cell arteritis, Goodpasture's syndrome, Graves' disease, Guillain-Barré syndrome. Hashimoto's thyroiditis, idiopathic thrombocytopenic purpura, IgA nephropathy, myasthenia gravis, pemphigus foliaceous, pemphigus vulgaris, polyarteritis nodosa, polymyositis/dermatomyositis, rheumatoid arthritis, scleroderma, Sjögren's syndrome, systemic lupus erythematosus, Takayasu's arteritis, and Wegener's granulomatosis.

Cancers which can be treated include solid tumors, such as tumors of the breast, bone, prostate, lung, adrenal gland (e.g., adrenocortical tumors), bile duct, bladder, bronchus, nervous tissue (including neuronal and glial tumors), gall bladder, stomach, salivary gland, esophagus, small intestine, cervix, colon, rectum, liver, ovary, pancreas, pituitary adenomas, and secretory adenomas. Methods of the invention are particularly useful for treating drug- or radiation-resistant solid tumors.

Cancers of the blood (e.g., lymphomas and leukemias) also can be treated including, but not limited to, multiple myeloma, Hodgkin's lymphoma, non-Hodgkin's lymphomas (e.g., cutaneous T cell lymphomas such as Sezary syndrome and Mycosis fungoides, diffuse large cell lymphoma, HTLV-1 associated T cell lymphoma, nodal peripheral T cell lymphoma, extranodal peripheral T cell lymphoma, central nervous system lymphoma, and AIDS-related lymphoma). Leukemias include acute and chronic types of both lymphocytic and myelogenous leukemia (e.g., acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia). Monoclonal gammopathy of undetermined significance (MGUS), the precursor of myeloma, also can be treated.

Viral infections which can be treated include infections of enveloped viruses which utilize the unfolded protein response pathway when they replicate and form infectious progeny (e.g., measles, pox viruses, Ebola, etc.). Infections also include those of Epstein Barr virus (EBV), cytomegalovirus (CMV), Flaviviruses (e.g., Japanese Encephalitis Virus and West Nile Virus), and Hepatitis C virus (HCV).

Archease inhibition may have therapeutic effect in several diseases. Such diseases include proliferative diseases, in particular cancer. By reducing tRNA processing the proliferative activity can be greatly decreased resulting in reduced cell growth. Therefore the present invention provides a method of reducing tumor cell growth comprising administering an Archease inhibitor to said cell. It is known that tumor cells have abnormally high rates of Polymerase (Pol) III transcription (Marshall & White, 2008). Since Pol III synthesizes tRNAs, targeting the tRNA ligase will turn (high) tRNA production rate-limiting in cancer cells. The importance of tRNA splicing components for proliferation is e.g. disclosed in the WO2004/087884 A2 (incorporated herein by reference).

In a further aspect the present invention provides the treatment of a disease or infection dependent on host polymerases, such as hepatitis delta virus infection comprising administering an Archease inhibitor to said cell. The human hepatitis delta virus is the only animal virus known to replicate its RNA genome using a host polymerase. Host factors involved in the replication of the virus are elusive. A ligase-host factor in circularizing the viral genome during replication is implicated (Reid & Lazinski, 2000). In a combined proteomic-RNAi screen identified more than 100 proteins associated to the hepatitis delta antigens. A portion of the identified proteins has roles in RNA metabolism, and two of those are the ligase HSPC117 and also its complex partner DDX1. Combined this suggests that Archease is a decisive target for treating a hepatitis delta virus infection.

Furthermore the present invention relates to a method of treating a disease in a subject associated with dysfunctional tRNA splicing, in particular being deficient in a tRNA ligation by RNA>p ligase, preferably pontocerebellar hypoplasia, comprising administering an Archease molecule to said subject. A link has been established between the tRNA splicing pathway and Pontocerebellar hypoplasia. This disease belongs to a group of degenerative autosomal recessive disorders with prenatal onset, atrophy or hypoplasia of the cerebellum and other motor impairments. Mechanistically these diseases are associated with aberrant removal of introns and ligation of exons during tRNA splicing. Therefore administration of a functional Archease can restore normal splicing and intron removal and treat the disease, while it is also well known, but not understood at a molecular level, that tRNA metabolism has a special impact on brain function.

Cells respond to oxidative stress by secreting Angiogenin, a factor that displays ribonuclease activity besides its known role in angiogenesis. Angiogenin cleaves mature tRNAs at the anticodon loop, thereby generating tRNA fragments known as tiRNAs, for tRNA-derived stress-induced RNAs. tiRNA accumulation impairs protein synthesis and is therefore detrimental to cell health and function. Inactivating the human tRNA ligase HSPC117 leads to an increase in tiRNAs in cultured cells. Increased HSPC117 reverts Angiogenin cleavage and reduces tiRNA levels. HSPC117 therefore may have a distinct role in re-ligating Angiogenin-cleaved tRNA. This angiogenin reaction cannot be reverted upon inhibition of HSPC117 molecule. In turn HSPC117 activity is enhanced by Archease as shown herein. In the absence of Archease, HSPC117 has only a low residual activity. Thus, the present invention also relates to a method of modulating tiRNA amounts in a cell, such as by increasing or decreasing Archease activity in a cell.

Various types of physiological stress induce the unfolded protein response including, but not limited to, hypoxia, nutrient starvation, acidosis, and genetic damage resulting in mutant or over-expressed misfolded proteins (oncogenic stress). One or more of these conditions are manifest in cancer cells, which may in part be mediated by the microenviroment of the tumor. It is likely that the cytoprotective arm of the unfolded protein response (UPR) plays an anti-apototic role in tumor survival. In addition, bio- and chemotherapeutic drugs and radiation treatments may further impact the protein folding and degradation cycle in the ER thereby inducing the UPR as a protective resistance mechanism. Patients succumb to cancer because either the tumor is resistant to conventional therapies or returns in a resistant form after an initial response to treatment and, therefore, new treatments and treatment combinations are needed.

Angiogenesis inhibitors block tumor growth by inhibiting new blood vessel formation, a process that would enhance the stress effects of the tumor microenvironment. A promising approach to further reduce tumor burden would be to administer anti-angiogenesis agents in combination with Archease inhibitors.

Interference with UPR may sensitize cancer cells to various chemotherapeutics that elevate the cellular stress and thus, Archease inhibitors may become important therapies in conjunction with current and future standard of care in cancer.

In some embodiments an Archease inhibitor is administered in combination with a cancer therapeutic agent, for example radiation therapy or a cancer therapeutic agent (e.g., a chemotherapeutic agent or a biotherapeutic agent). The cancer therapeutic agent can be administered separately or together with the Archease inhibitor. The cancer therapeutic agent can be administered at essentially the same time as the Archease inhibitor or can be administered either before or after the Archease inhibitor.

In a further aspect, the present invention provides a pharmaceutical composition comprising an Archease expressing nucleic acid, preferably in form of an expression vector, or an Archease inhibitor, preferably an antibody or siRNA or variant thereof as described above. Such a composition can be a ready to use composition, e.g. for the treatment of any disease described above. Pharmaceutical compositions or formulations for therapeutic or prophylactic use may comprise a pharmaceutically acceptable diluent, carrier, solubilizer, emulsifier and/or preservative. The invention also provides for pharmaceutical compositions comprising a therapeutically effective amount of an Archease inhibitor or expression nucleic acid. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascorbic acid or sodium metabisulfite. Selection of a particular composition will depend upon a number of factors, including the condition being treated, the route of administration and the pharmacokinetic parameters desired. Nucleic acids and siRNA formulations are preferably administered in liposome formulations. Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art. Preferably intracellular administration is facilitated by use of suitable vehicles like liposomes or microsomes.

The invention further provides a method of obtaining an Archease inhibitor, comprising contacting Archease with a candidate inhibitor determining the activity of a RNA ligase in contact with said Archease, wherein an inhibitor is obtained when said activity of said ligase is reduced in comparison to Archease that has not been treated with said inhibitor. Such a ligase is e.g. HSPC117. Tests to determine the ligase activity are known in the art, as e.g. described in WO 2012/028606 A1 or as described herein, and involve the ligation of two RNA molecules under suitable conditions as described herein. A preferred test is shown in example 12. In general, the Archease activity test monitors the activity of an Archease-dependent RNA ligase, such as RtcB/HSPC117, in the presence of Archease and its substrates with and without the inhibitor. Apart from the presence or absence of the inhibitor the conditions of the assay should be the same. The ligation test can also be a splicing test together with a splicing endonuclease. Said contacting step and/or the ligase activity determination can be in vitro (e.g. of isolated enzymes), in a cell or cell line or in a model non-human animal, e.g. as described above. The inhibitor can be used in the above described methods of treatment, especially in the pharmaceutical formulations as mentioned above. Inhibitors are e.g. antibodies, siRNAs, small organic molecules but also inactive forms of Archease, like the mutant forms with mutations in amino acids corresponding to D39 and/or K144 of SEQ ID NO: 28 (e.g. corresponding to D39A and K144A mutations), which render said mutated Archease inactive and inhibit wild-type Archease, which would otherwise be active. Preferred inhibitors are non-hydrolysable GTP analogues, such as GMPCPP. Non-hydrolysable GTP analogues may act as competitive inhibitors for the guanylation of RtcB proteins. Preferably the inhibitor is tested according to the test method described above. Such an inhibitor or any inhibitor described herein can be used in any one of the inventive uses, methods or kits requiring an Archease inhibitor.

Archease and the ligase may also be used in combination during contacting with the candidate inhibitor. Thus, the invention also provides the inventive method of obtaining an inhibitor comprising contacting Archease with a candidate inhibitor, wherein the Archease is in combination with a RNA ligase, such as HSPC117, and determining the activity of the RNA ligase, wherein an inhibitor is obtained when said activity of said ligase is reduced in comparison to an Archease-ligase combination that has not been treated with said inhibitor. In such a combination the Archease and the ligase may co present coincidentally in a test container, cell or model animal as described above.

As shown herein, Archease acts on ligases like HSPC117 by promoting the formation of an HSPC117-guanylate adduct, probably by releasing the GMP associated after an initial round of catalysis. Thus the inventive method of obtaining an Archease inhibitor can also be adapted by determining loss of guanylation activity of the Archease, e.g. by determining a transfer of a G residue to the ligase.

In said methods, the substrate of the reaction, e.g. GTP or polynucleotides, may be labeled for determining the activity. Example labels include radioactive labels, fluorescent, or chemical. The Archease and/or the ligase may be immobilized to allow easy separation from the test solutions.

The present invention is further illustrated by the following figures and examples, without being limited to these specific embodiments of the present invention.

FIGURES

The patent or application file contains at least one drawing executed in color. Copies of this patent or patent application publication with color drawing(s) will be provided by the Office upon request and payment of the necessary fee.

FIG. 1: The human tRNA ligase apparently catalyses a limited number of substrate turnovers. A) Affinity purified, FLAG-tagged HSPC117 associates with the proteins DDX1, FAM98B, ASW and CGI-99. B) Affinity purified FLAG-tagged HSPC117 processes tRNA exon halves into mature tRNAs and circularizes the linear intron released by the tRNA endonuclease. C) Varying amounts of affinity purified tRNA ligase complex were incubated with the isolated linear intron and the formation of ligated species was monitored by gel electrophoresis followed by phosphorimaging. The signals corresponding to concatemerized intron were quantified and plotted as fraction of the total signal detectable in the respective lane.

FIG. 2: HSPC117 and Archease share their taxonomic coverage. RtcB/HSPC117 proteins are widely distributed in bacteria, archaea and vertebrates but not in plants and fungi. The taxonomic coverage of Archease proteins correlates with the occurrence of RtcB/HSPC117.

FIG. 3: Archease boosts RNA ligation by the human tRNA ligase complex. A) Time-course ligation assay with affinity-purified tRNA ligase complex and pre-cleaved tRNA substrates in absence or presence of recombinant Archease. B) Time course ligation assay with affinity purified tRNA ligase complex and isolated linear introns (2.5 µM) in absence or presence of recombinant Archease (8.5 µM) expressed in *E. coli*. The signals corresponding to the concatemerized intron were quantified and plotted as fraction of the total signal detectable in the respective lane.

FIG. 4: Archease neither exhibits RNA ligase activity nor co-purifies with the human RNA ligase complex. A) Coomassie Blue stained preparations of FLAG-tagged Archease and HSPC117 affinity purified at 150 mM NaCl. B) RNA ligase activity assay of FLAG-HSPC117 and FLAG-Archease using pre-cleaved tRNA substrates. Extracts of HEK 293 cells were used as a negative control. * Indicates unspecific products.

Figure 5:
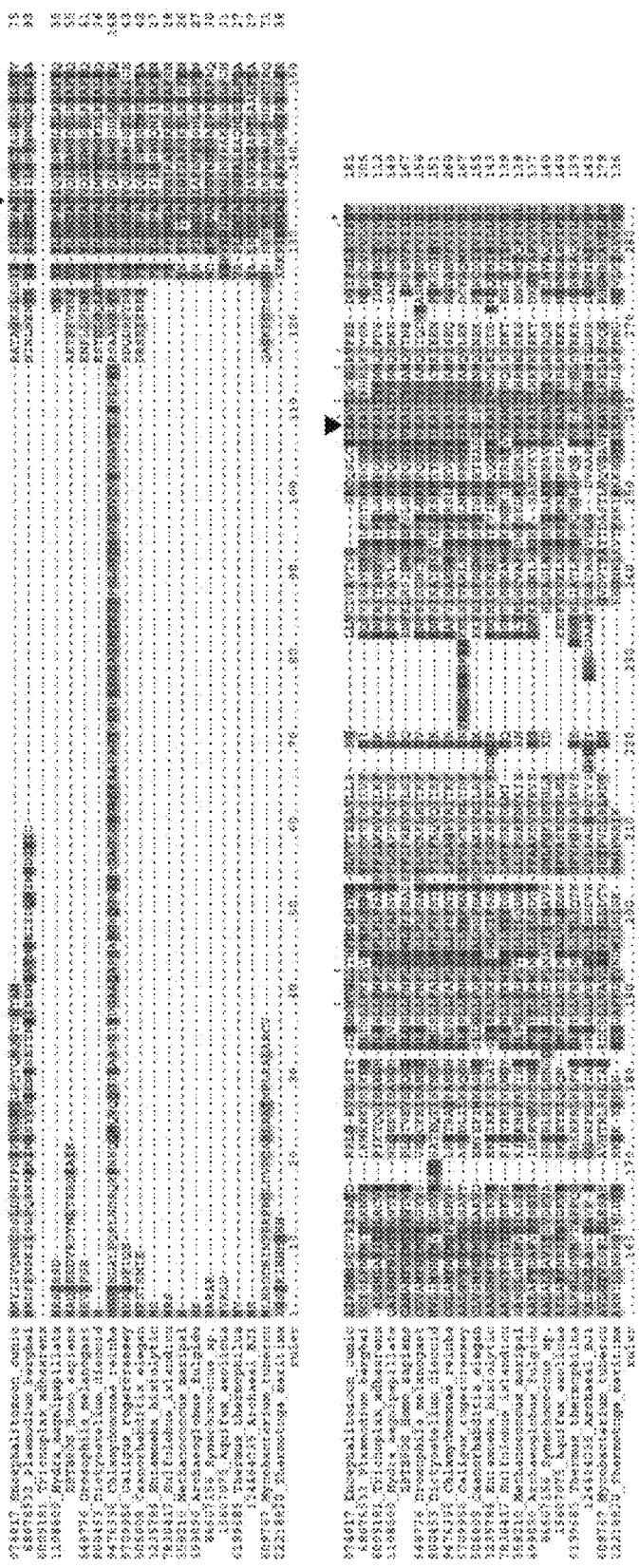

FIG. 5: Alignment of various Archease protein sequences. From top to bottom SEQ ID NO: 24 to 43. Highly conserved amino acids (D39 and K144, numbered according to the human protein sequence, SEQ ID NO: 28) mutagenized in this study are highlighted by black triangles.

FIG. 6: The point mutations D39A and K144A abolish the function of Archease in RNA ligation. A) Time-course of ligation activity of FLAG-HSPC117 complexes upon addition of recombinant wild-type or mutant Archease (15 µM). B) SDS-PAGE analysis of purified recombinant wild-type and mutant Archease.

Figure 7:
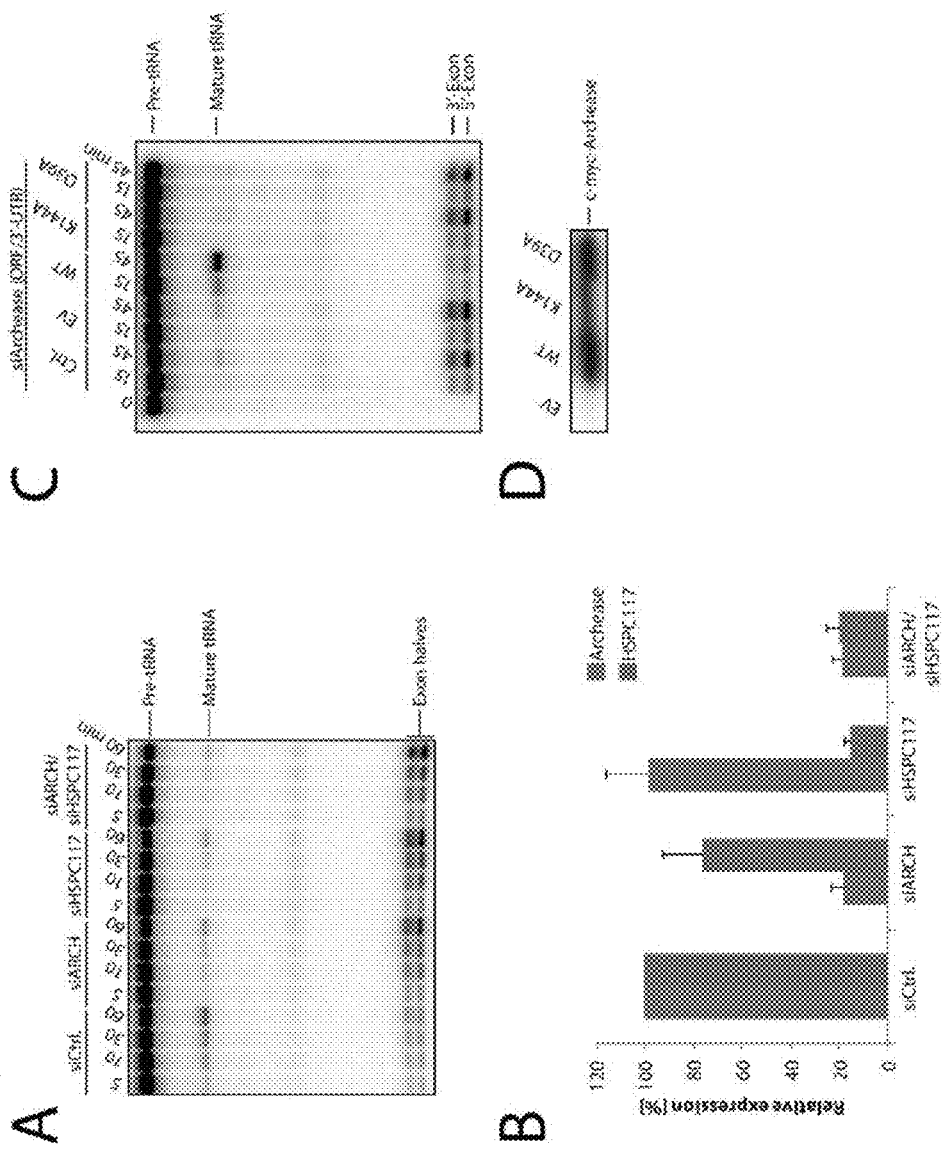

FIG. 7: HSPC117 and Archease both contribute to the maturation of pre-tRNA transcripts in processing assays. A) HeLa cell extracts depleted of Archease and/or HSPC117 by RNA interference show impaired formation of mature tRNA in pre-tRNA splicing assays. Both proteins appear to contribute equally to tRNA ligase activity in these extracts. B) Quantification of the reduction of mRNA levels of Archease and HSPC117 upon transfection of siRNAs by real time PCR. Comparable depletion efficiencies were attained for both transcripts. Depletion of either factor does not lead to a substantial reduction of the other. C) The defect in tRNA maturation observed in extracts depleted of Archease by RNAi can be restored by over-expressing wild-type, but not mutant versions of the protein. D) Western Blots showing levels of over-expressed wild-type and mutant Archease. Ctrl. indicates a control plasmid, EV an empty vector.

FIG. 8: The human tRNA ligase HSPC117 and Archease are both required for non-conventional splicing of Xbp1 mRNA during the Unfolded Protein Response (UPR). A) Experimental outline for in vitro splicing assay. B) An internally labeled fragment of Xbp1 mRNA was pre-cleaved with recombinant Ire1 endonuclease and supplemented with buffer or HeLa whole-cell extract (wce) for the indicated time points to allow ligation of exon halves. Formation of splice product is specific to the presence of both Ire1 and cell extract. Lanes marked "unspliced" and "spliced" contain control transcripts to mark the size of the splice product. C) HSPC117 and Archease both contribute to non-conventional splicing. 3' end labeled Xbp1 was pre-cleaved with Ire1 and supplemented with whole-cell extract from HeLa cells treated with siRNAs as indicated above the lanes. Cell extracts were harvested 72 hrs post transfection. D) Ligase activity for non-conventional splicing resides in HSPC117 but not in Archease. In vitro splicing assay using 3'end labeled Xbp1 carried out using whole cell extract (input) or FLAG-IP from HEK293 cells stably expressing FLAG-HSPC117, FLAG-Archease or FLAG-DDX1. Ligation activity is only found in IPs of integral members of the tRNA ligase complex. E) Non-conventional splicing activity is stimulated by addition of Archease. Splicing assay using 3' end labeled Xbp1 carried out as above with addition of buffer or recombinant protein as indicated above the lanes. D39A and K144A represent Archease mutagenized at highly conserved amino acid positions rendering the protein inactive. Bovine Serum Albumine (BSA) was included as control.

FIG. 9: Time course for 5' end and 3' end labelled Xbp1: In vitro splicing assay produces identical splice product irrespective of the position of the radioactive label.

FIG. 10: In vitro ligation activity is proportional to amount of cell extract added.

Figure 11:
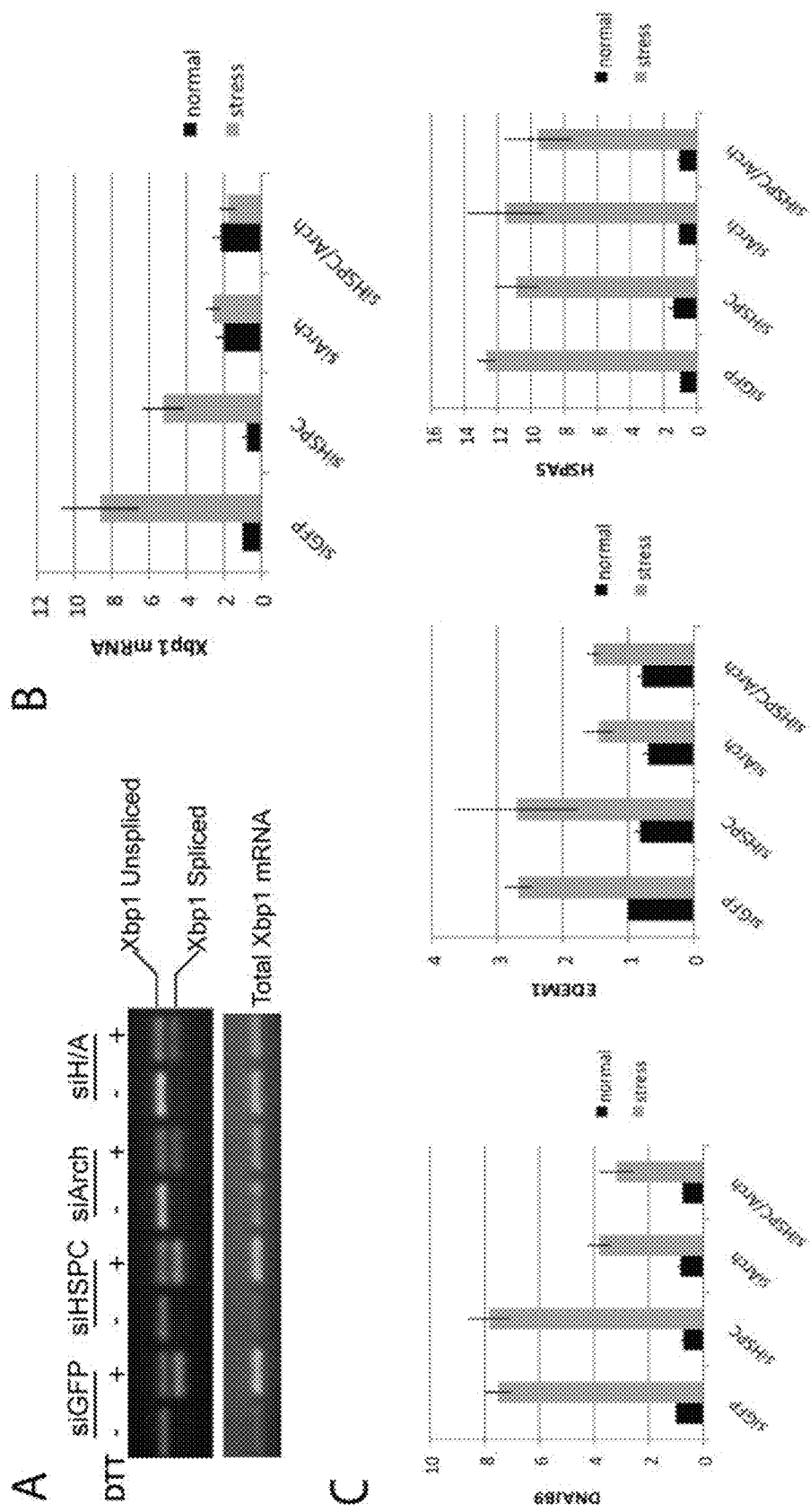

FIG. 11: Depletion of HSPC117 and Archease using siRNAs reduces non-conventional splicing of endogenous Xbp1 mRNA in HeLa cells.
A. RT-PCR for Xbp1 spliced forms. Total RNA was isolated from siRNA-treated cells 120 hrs post-transfection. Stress induced by treating cells with 2 mM DTT for 4 hrs.
B. Q-PCR for total Xbp1 mRNA levels following siRNA-mediated KD and stress induction.
C. Upregulation of Xbp1 target genes is impaired upon depletion of HSPC11 and Archease. Q-PCR for DNAJB9, EDEM1 and HSPA5 carried out using same cDNA as above. Error bars represent standard deviation; all experiments were carried out in triplicates.

Figure 12:
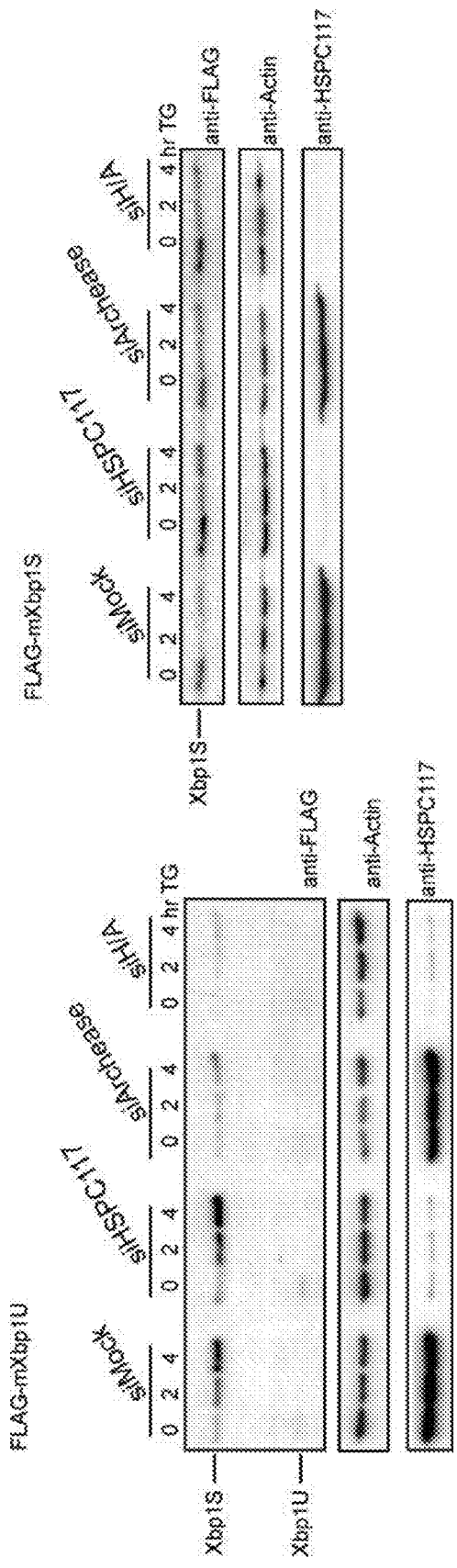

FIG. 12: Depletion of HSPC117 and Archease ablates Xbp1S accumulation upon stress induction.
HeLa cells stably expressing FLAG-mXbp1U (WT) or FLAG-mXbp1s (constitutively spliced) were transfected with siRNA for 72 hrs prior to stress-induction with 0.3 uM thapsigargin (TG). Cells were lysed in RIPA buffer (Thermo-Scientific) and analysed by Western blotting.

Figure 13:
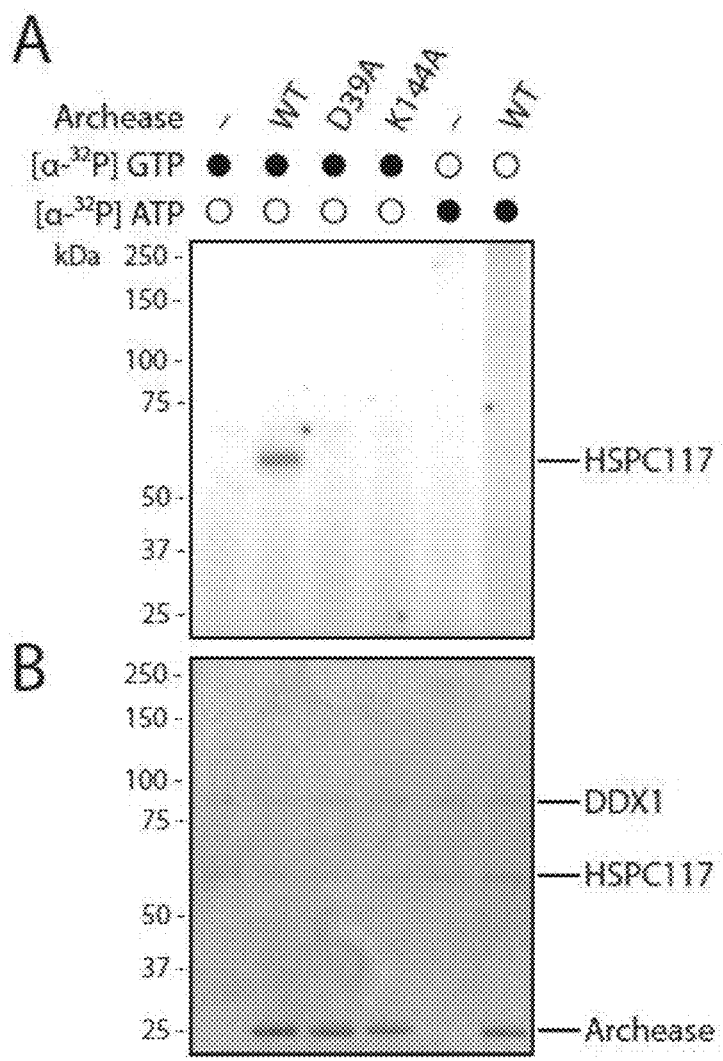

FIG. 13: Guanylation of HSPC117 within the human tRNA ligase complex by Archease. A. Affinity purified FLAG-HSPC117 was incubated with wild-type or mutant versions of Archease or buffer as a control in the presence of [α-32P] GTP or [α-32P]ATP, full circles indicate inclusion, empty circles indicate omission from reaction mixtures. Reaction mixtures were resolved by SDS PAGE and radiolabeled protein species visualized by phosphorimaging. B. Equal loading was confirmed by Coomassie staining.

Figure 14:
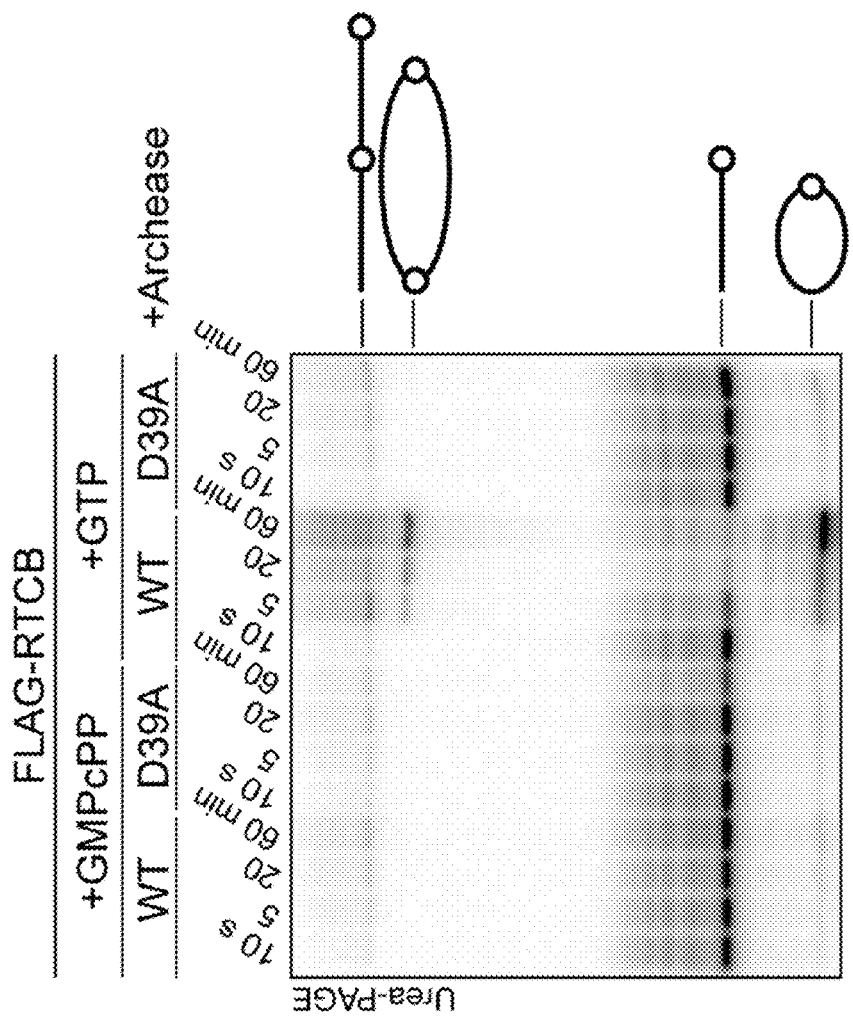

FIG. 14: Assay to monitor inhibition of RNA ligase activity. The figure shows the ligation activity of FLAG-RTCB, the catalytic subunit of the human tRNA ligase, in the presence of wildtype or mutant (D39A) Archease and GTP or the non-hydrolyzable analog GMPcPP. The linear substrate (second from bottom to top) is converted into a circular product (bottom) or a concatemer (top), which is further circularized (third from bottom to top). Ligation only took place with wild-type Archease and GTP. The addition of non-hydrolysable GMPCPP inhibits the reaction.

Figure 15:
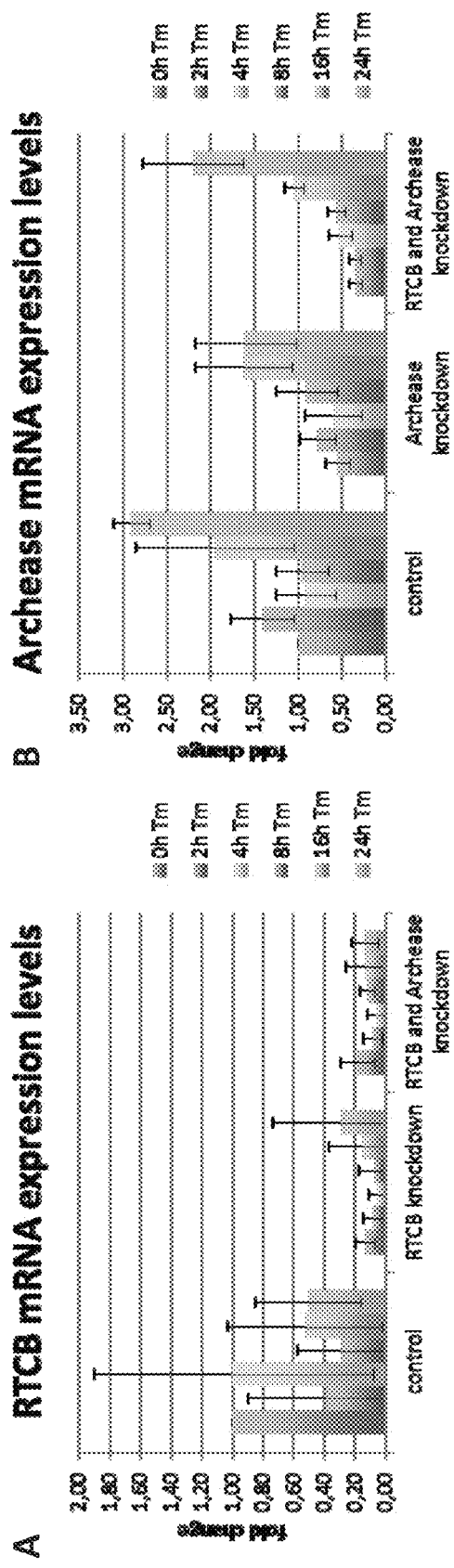

FIG. 15: Knockdown of RTCB and Archease in HeLa cells. The figure shows RTCB (A) and Archease (B) mRNA expression levels upon stable knockdown in HeLa cells by means of short hairpin RNAs (shRNAs). Both in control and knockdown cells, mRNA expression levels vary upon induction of the UPR with tunicamycin (Tm). However, decreased mRNA expression levels are observed throughout the entire experimental period.

Figure 16:
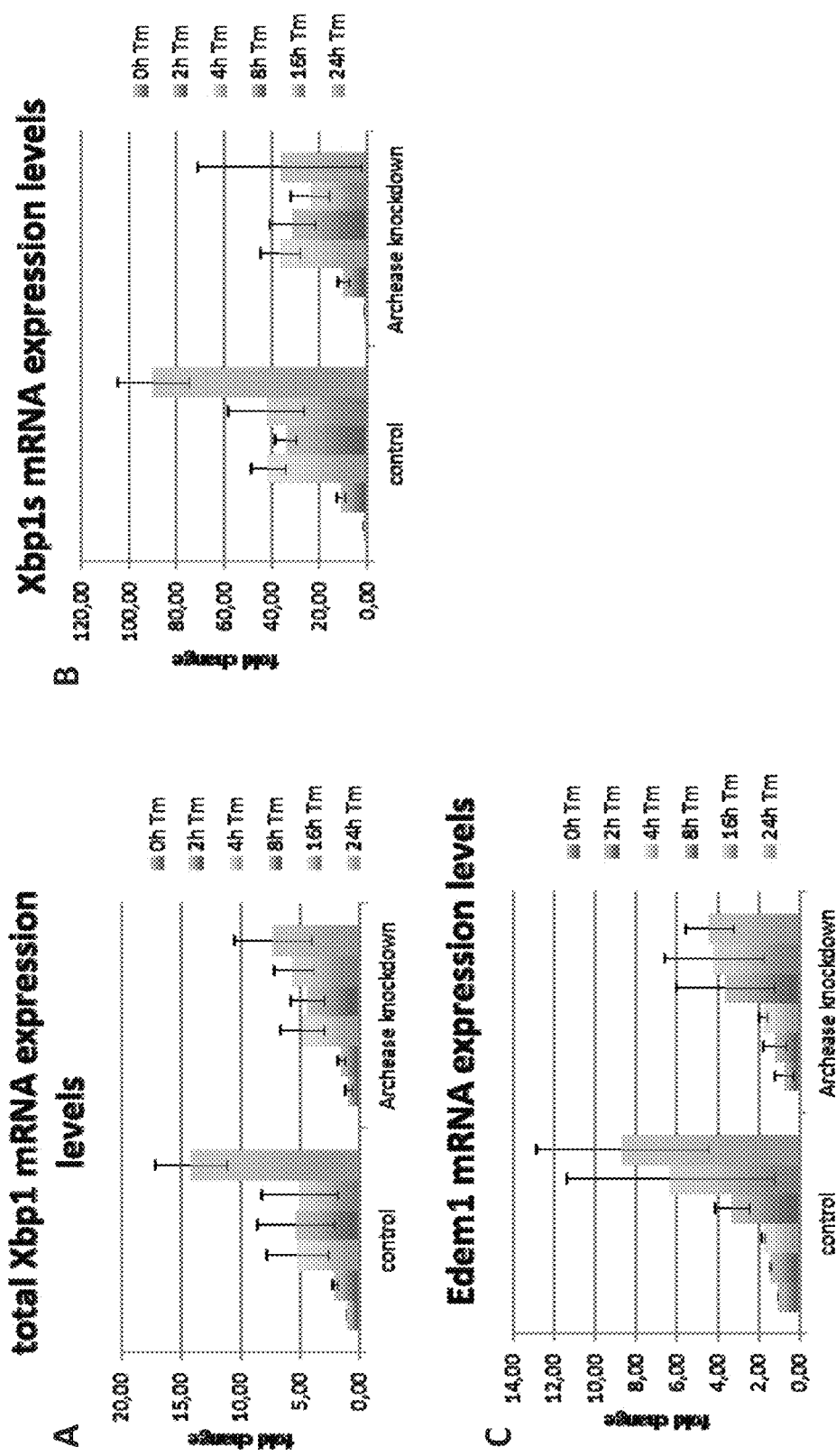

FIG. 16: Reduced XBP1 splicing activity and EDEM1 induction after knockdown of Archease in HeLa cells. The figure shows expression levels of total Xbp1 mRNA (unspliced and spliced, A); spliced Xbp1 mRNA (Xbp1s, B) and Edem1 (C) as revealed by qPCR. Compared to control cells, knockdown of Archease leads to a decrease in mRNA Xbp1 splicing as seen by reduced levels of Xbp1s mRNA. This impacts on the expression levels of both total Xbp1 and Edem1 mRNAs.

FIG. 17: Knockdown of RTCB and Archease in H929 cells. The figure shows decreased mRNA expression levels of RTCB (A) and Archease (B) upon stable knockdown in H929 cells by means of shRNAs.

EXAMPLES

Example 1

Reduced Activity of HSPC117 Complex without Archease

It was found that the HSPC117 complex (FIG. 1A) exhibits RNA ligase activity (FIG. 1B) which, in a time course analysis, does not seem to progress over time after an initial burst of activity (FIG. 1C). This result suggests a lack of turnover in the enzymatic reaction and that additional factors are required to attain full activity.

Example 2

Archease is Required for Efficient RNA Ligation by the Human RNA Ligase Complex In Vitro Addition of Archaease influences ligase activity of affinity purified human tRNA ligase complexes. As shown in FIGS. 3A and B, addition of recombinant Archease boosts ligation activity to a great extent (including circularization of the intron).

Example 3

Archease Neither Exhibits RNA Ligase Activity Nor Co-Purifies with the Human RNA Ligase Complex Stable cell lines expressing a FLAG-tagged version of Archease and HSPC117 were generated to perform immunoprecipitations. Fluted FLAG-Archease was assayed for tRNA ligation in parallel with FLAG-HSPC117, which contains the entire tRNA ligase complex. As shown in FIG. 4A, affinity-purified FLAG-tagged Archease neither associated with components of the tRNA ligase complex, nor did the tRNA ligase complex co-purify with Archease. RNA ligase activity was only detectable in reactions containing affinity-purified RNA ligase complex but not FLAG-tagged Archease (FIG. 4B).

Example 4

The Point Mutations D39a and K144A Abolish the Function of Archease in RNA Ligation To study the function of Archease the available NMR structure from the euryarchaeote *Methanothermobacter thermautotrophicus* (Yee et al., 2002) (36% identical to human protein) was used and aspartic acid (D) 39 and lysine (K) 144, both extremely conserved residues, were replaced by alanines (D39A; K144A) (FIG. 5). Wild-type and mutant versions of Archease were over-expressed in HeLa cells and tRNA ligase activity was measured. As seen in FIG. 6A, addition of recombinant wild-type Archease led to an increase in RNA ligase activity while neither of the mutant versions of Archease stimulated the low levels of ligation achieved in its absence. FIG. 6B confirms equal concentrations of recombinant proteins added to the reactions.

Example 5

Archease is Required for Efficient In Vitro Splicing of Pre-tRNA Substrates in Human Cell Extracts It was also tested whether depletion of Archease would impair tRNA splicing activity in cell extracts. HeLa extracts depleted of Archease by RNAi were incubated with an internally labeled pre-tRNA substrate and the appearance of mature tRNA was monitored (FIG. 7A). To silence HSPC117 a commercially available mixture of siRNA duplexes was used (Dharmacon Cat. No. L-017647-00-0005). To silence Archease a single siRNA duplex of the sequence 5'-UGA CAU UUA AGA CAC CAA A[dT][dT]-3' (sense strand; SEQ ID NO: 47) and 5'-UUU GGU GUC UUA AAU GUC A[dT][dT]-3' (antisense strand; SEQ ID NO: 48) was used. The obtained results were confirmed using a commercially available mixture of siRNA duplexes (Dharmacon Cat. No. L-017915-01-0005).

For the splicing assay RNA was prepared by T7-transcription from PCR product containing spliced and unspliced form of human Xbp1. Substrates were labelled internally using a-GTP and at the 3'end using ligation to pCp. Substrate was pre-cleaved with recombinant Ire1 for 5 mins in tRNA ligation buffer with subsequent addition of protein extract of FLAG-IP eluate to total volume of 5 µl. Samples were treated with proteinase K and phenol-chloroform extracted prior to loading on 10% PAGE gel.

Similar to targeting the tRNA ligase HSPC117 (Popow et al., 2011), depletion of Archease severely impaired tRNA ligation. Transfection of siRNAs targeting Archease efficiently depleted its mRNA (FIG. 7B). In addition, it was confirmed that lack of ligation following the depletion of Archease could not be attributed to destabilization of HSPC117. Ruling out off-target effects, it was possible to restore tRNA maturation in extracts depleted of Archease by simultaneous expression of the wild-type protein but not the point mutants D39A and K144A (FIGS. 7C and D).

Example 6

Archease is Required for Efficient In Vitro Splicing of Xbp1 mRNA During the Unfolded Protein Response Perturbation of normal ER function causes mis- or unfolded proteins to accumulate leading to activation of the unfolded protein response (UPR). One of three UPR pathway inducers in mammals, the ER transmembrane protein Ire1, cleaves the Xbp1 mRNA specifically to remove a 26 nt intron (FIG. 8A). In vitro splicing assays carried out with a cleaved Xbp1 RNA minimal substrate and HeLa cell extracts depleted of HSPC117 and/or Archease revealed that both proteins are required for efficient ligation of the exons generated by recombinant Ire1 (FIGS. 8B and C). Loss of HSPC117, the catalytic subunit of the mammalian tRNA ligase complex, caused strongly reduced exon-exon ligation. Interestingly, depletion of the newly identified tRNA ligase-activating factor Archease resulted in a comparable loss of ligation activity (FIG. 8C). None of the additional four components of the tRNA ligase complex were required for ligation in agreement with previous findings (WO 2012/28606). As for cleaved pre-tRNA substrates, only affinity purified HSPC117 and DDX1 but not Archease exhibited RNA ligase activity towards cleaved Xbp1 RNA minimal substrates (FIG. 8D). The reduced ligation activity seen in Archease-depleted extracts raised the question whether Archease is an RNA ligase or rather acts to stimulate the ligation activity of other ligases. To address this question stable cell lines expressing FLAG-tagged versions of HSPC117, Archease, and DDX1 (a DEAD-box helicase component of the human tRNA ligase complex) were generated and the Xbp1 ligation assay using FLAG-IPs was performed. As shown in FIG. 8D ligation activity in FLAG-HSPC117 and FLAG-DDX1 IPs were observed while no ligation was detected for FLAG-Archease IP.

Addition of recombinant wild-type Archease but not its mutagenized versions strongly stimulated ligation of Xbp1 RNA minimal substrates by affinity purified human tRNA ligase complex (FIG. 8E). To further address the stimulatory activity of Archease both HSPC117 and Archease were depleted by RNAi and then an Archease rescue-construct containing either WT or MUT Archease was introduced. Although Archease harbours no ligase activity in itself as seen in IP experiments the over-expression of WT Archease is sufficient to partly rescue the in vitro ligation activity in KD extracts showing that its stimulatory activity is strong enough to boost activity of a small amount of HSPC117 remaining.

These experiments also show that over-expression of mutant Archease by itself is sufficient to impair in vitro ligation activity despite partial depletion of the catalytic subunit of the tRNA ligase complex.

Interestingly, when Xbp1 mRNA was pre-cleaved with Ire1 prior to addition of cell extract a single fragment appeared resulting from the ligation of the two Xbp1 exon halves. A similar fragment was observed in splicing assays using either 5'- or 3'-endlabelled Xbp1 RNA (FIG. 9), arguing against a contaminating cleavage event. Splicing activity was seen to be proportional to the amount of extract added (FIG. 10).

Example 7

Depletion of HSPC117 and Archease Impairs Non-Conventional Splicing and Prevents Activation of Xbp1 Downstream Targets in Cell Culture To expand the findings from the in vitro ligation assay in a more physiological setting HSPC117 and Archease were depleted by siRNA transfection in HeLa cells and stress was induced by treating the cells with 1 mM DTT or 0.3 uM thapsigargin for 4 hrs. The accumulation of spliced Xbp1 was monitored by RT-PCR using primers flanking the non-conventional splice site in Xbp1. Surprisingly depletion of HSPC117 alone caused only limited change in Xbp1 splicing upon stress induction, while depletion of Archease impaired splicing significantly (FIG. 11A); both proteins were depleted to comparable levels. Q-PCR for total Xbp1 levels in siRNA-treated cells corroborated the RT-PCR results (FIG. 11B). In control samples the extended stress induction led to elevated levels of Xbp1 mRNA since the Xbp1S protein feeds back on its own promoter, leading to strong transcription of Xbp1 mRNA during the stress response. Depletion of HSPC117 resulted in about 50% reduction in transcript activation while the depletion of Archease abolishes the enhanced production of Xbp1 mRNA altogether (FIG. 11B). These results argue that the stimulatory activity elicited by Archease is sufficient to maintain ligation activity in the presence of reduced amounts of HSPC117.

The accumulation of Xbp1S protein activates transcription of genes that ameliorate ER stress. The lack of UPR ligase function would therefore be expected to impair upregulation of these downstream targets upon stress induction. To measure this Q-PCR for the Xbp1-specific factors EDEM1 and DNAJB9 as well as for the general stress responder HSPA5 (BiP) was performed. The activation of EDEM1 and DNAJB9 was abolished in cells depleted of Archease using siRNAs, while HSPC117 depletion had a minor effect (FIG. 11C). The activation of HSPA5 was only mildly affected by the depletion of both Archease and HSPC117 confirming the specific disruption of the Ire1 signaling pathway upon depletion of non-conventional RNA splicing. The upregulation of down-stream targets mirrors the accumulation of spliced Xbp1 seen in FIG. 11A arguing that impaired Xbp1 mRNA splicing translates directly into loss of Xbp1s protein (FIG. 12 left panel); presumably the mild reduction in Xbp1 splicing seen in HSPC117-depleted cells still leaves enough protein to initiate the activation of down-stream genes. This shows that UPR-activated target genes depend on a functional tRNA ligase machinery for their upregulation upon stress.

Example 8

Depletion of HSPC117 and Archease Impairs Accumulation of Xbp1S

To confirm the RT- and Q-PCR results described above Western blots to detect direct deficiency in Xbp1 protein accumulation upon stress induction in siRNA-treated HeLa cells were performed. Stable cell lines expressing FLAG-tagged mouse Xbp1 were generated. Expression of an Xbp1 mRNA with the non-conventional intron removed (constitutive expression of Xbp1S) was used as a control. Expression level was only 2-3 fold above endogenous Xbp1 as seen by RT-PCR and stress induction led to comparable splicing pattern for endogenous hXbp1 and transgenic FLAG-mXbp1. Stable cell lines were treated with siRNAs for 72 hrs, lysed and analysed by Western blotting (FIG. 12). Similar to results from RT-PCRs depleting HSPC117 had no effect on Xbp1S protein accumulation while depletion of Archease caused a strong drop in protein level compared to the control transfection. Depletion of both proteins showed synergistic effect resulting in an almost complete loss of Xbp1S upon stress induction.

Despite years of intense study the identity of the ligation process in non-conventional Xbp1 splicing has eluded discovery in mammalian cells. While HSPC117 is the likely candidate for this splicing activity, it has been shown herein with certainty that ligation is dependent on Archease for stimulation of ligase activity. It is possible that a few ligase complexes (possibly associated with the ER membrane) may suffice to splice Xbp1 upon induction of stress response as long as Archease is present to stimulate enzymatic rate. This fits with observations from RT-PCR and Q-PCR assays where initially cells were harvested after very short stress exposure to spot kinetic differences in initial splicing. When strategy was changed and stress induction was run for several hours before sample harvesting a differential accumulation of spliced product was detected. Presumably the enhanced number of Xbp1 transcripts requiring splicing caused by the initial pool of Xbp1S makes it harder for the limited amount of HSPC117 in siRNA-treated cells to keep up ligating the available substrates and thereby makes it possible to see a significant difference in amount of spliced Xbp1 mRNA.

Steady-state levels of unspliced Xbp1 mRNA are upregulated in the absence of stress upon a) Archease depletion by RNAi, b) through over-expression of dominant-negative mutant Archease, or c) most strongly seen when both are combined. This phenomenon could be caused by enhanced transcription (through an unknown feedback mechanism) or by stabilisation of the unspliced Xbp1 mRNA (due to altered subcellular localisation).

Example 9

Archease is Required for Guanylation of HSPC117

Since HSPC117 alone does not undergo guanylation in vitro it was tested whether Archease supports RNA ligation by HSPC117 by mediating its guanylation. Affinity purified FLAG-HSPC117 was incubated with wild-type or mutant and inactive variants (D39A; K144A) of Archease or buffer as a control in the presence of [α-32P]GTP or [α-32P]ATP. Reaction mixtures were resolved by SDS PAGE and radiolabeled protein species visualized by phosphorimaging or by Coomassie staining (FIGS. 13 A and B). Guanylation of FLAG-HSPC117 was only detectable in the presence of wild-type but not of mutant versions of Archease.

Example 10

Medical Applications of Inhibitors of Archease and the Human tRNA Ligase Complex The UPR, and especially the Ire1/Xbp1 branch, is found to be involved in an increasing number of diseases; most strikingly over-expression of Xbp1S in a mouse model was found to predispose animals to the development of multiple myeloma. Several compounds have been designed to impair the activity of Ire1 thereby ablating the over-activation of the pathway which contributes to disease progression; however, since Ire1 also has additional functions in the UPR independent on Xbp1 splicing targeting the ligase or Archease rather than the endonuclease would allow for enhanced specificity in disrupting over-activated Xbp1 signalling.

The implication of Archease and HSPC117 in the ligation of tRNA and mRNA substrates allows interfering with these splicing pathways in order to abolish negative effects associated with increased splicing activity.

Prolonged activity of the UPR, an indication that ER stress cannot be mitigated and homeostasis cannot be reestablished, correlates with cell death, suggesting that the commitment to apoptosis may have evolved to protect the organism from rogue cells that lack the capacity to ascertain the fidelity of their signaling components (Walter and Ron, 2011). A life-or-death decision, based on an assessment of whether ER stress can be mitigated in a timely fashion, nicely explains the UPR's central role in numerous human diseases. When homeostasis fails, the UPR can serve as an apoptotic executor that kills cells that would be beneficial, or as a cytoprotector that safeguards rogue cells to the detriment of the organism. Examples in the first category include retinitis pigmentosa, an inherited form of blindness in which the retina degenerates by apoptotic cell death when a misfolded mutant rhodopsin is produced during retinal development. Another such example is type II diabetes, in which pancreatic beta cells are compromised by excessive demand for insulin production. The second category is exemplified by enveloped virus infections that can exploit the UPR to increase the capacity of the ER to assist in viral replication. Similarly, certain types of cancer—especially those that arise in secretory tissues, such as multiple myeloma (see below)—use the cytoprotective role of the UPR to sustain their rapid growth. Impairing the endonuclease activity of IRE1 compromises the physiological cleavage of several RNA molecules during UPR. Inhibiting the ligase activity of HSPC117 and Archease facilitates this effect. Special targets are diseases where the spliced form of the Xbp1 protein is over-represented, such as multiple myeloma (Carrasco et al., 2007; Papandreou et al., 2011).

Example 11

Archease and UPR in Diabetes

In diabetes, the ultimate cell fate decision of life or death is dependent on the nature and severity of ER stress to which the β-cell is exposed. Thus, there are two types of ER stress conditions: resolvable and unresolvable. When ER stress can be resolved, the UPR promotes β-cell survival, whereas under unresolvable ER stress conditions, the UPR activates death effectors, leading to β-cell apoptosis. When β-cells are exposed to conditions that induce mild ER stress (e.g. physiological exposure to glucose fluctuations after a meal), the ER can facilitate stress mitigation and restore protein homeostasis, thus 'priming' cells for future ER stress insult and promoting cell survival. It has been shown that IRE1α and PERK are the primary transducers for regulating insulin production under these conditions, thus promoting activation of UPR prosurvival pathways. Unresolvable ER stress conditions occur when the UPR response is insufficient to restore ER homeostasis, leading to the induction of proapoptotic pathways. This can be attributed to several factors, including genetic mutations, chronic exposure to high glucose, and dysregulation of the UPR itself. This situation also benefits from a more efficient UPR, which could be achieved by overexpressing a tRNA ligase (e.g. HSPC117) and/or Archease. In fact, Fonseca et al. propose that discovering methods that could reduce ER stress to a tolerable state and/or modulating the UPR to preferentially activate survival over death pathways could lead to novel and efficient therapeutic treatments for diabetes.

Example 12

Assay to Monitor Archease Function and Inhibition of RNA Ligase Activity and Inhibitor Assay The RNA ligation activity of FLAG-RTCB, the catalytic subunit of the human tRNA ligase, was determined in the presence of wildtype or mutant (D39A) Archease with the addition of GTP or non-hydrolysable GMPcPP (5'-guanylyl-methylenebisphosphonate). Ligation only takes place with wild-type Archease and in the presence of GTP. GMPcPP strongly inhibits the ligation reaction. The reaction was carried out with FLAG-RTCB purified from HEK293 cells and hexahistidine tagged wild-type or mutant Archease. Furthermore, GTP or GMPcPP were used at 0.5 mM concentration. A linear intron derived from a radioactively labelled pre-tRNA that was transcribed with T7 polymerase and cleaved with recombinant tRNA endonuclease from *Methanocaldococcus jannaschii* served as substrate. Cleavage products were resolved on preparative denaturing polyacrylamide gels and the linear intron was eluted overnight and recovered by precipitation. With reference to FIG. 14, FLAG-RTCB and wild-type Archease in the presence of GTP are able to convert the linear substrate (second from bottom to top) into a circular product (bottom) or a concatemer (top), which is further circularized (third from bottom to top). This type of assay can be used to validate candidate inhibitors of the Archease or even the ligase or to screen compound libraries in order to find inhibitory molecules.

Example 13

Knockdown of RTCB (HSPC117) and Archease in Therapeutic Models

The expression of RTCB and Archease was reduced in HeLa and H929 cells by means of short hairpin RNAs (shRNAs) following an already established method that uses flanking sequences derived from microRNA-30 (Fellmann et al., Mol. Cell. 41, 733, 2011). Using a retroviral MSCV-based system knockdown constructs were stably expressed in the desired cell line which led to decreased expression levels of RTCB and/or Archease as seen in FIGS. 15-17. Furthermore, this decrease could be maintained when cells were treated with tunicamycin over a time period of 24 h. For this experiment, cells were plated at equal densities and treated with 1 ug/ml of tunicamycin (Tm). Hereafter, RNA was extracted using Trizol and cDNA was synthesized by means of the Maxima First Strand cDNA Synthesis Kit. QPCR was performed in duplicates and beta-actin was used for normalization. Expression levels were normalized to control cells expressing similar shRNA constructs targeting *Renilla* luciferase.

FIG. 15 illustrates the knockdown of RTCB and Archease in HeLa cells. RTCB and Archease mRNA expression levels were reduced upon stable knockdown in HeLa cells by means of shRNAs. Both in control and knockdown cells, mRNA expression levels vary upon induction of the UPR with tunicamycin. However, decreased mRNA expression levels are observed throughout the entire experimental period.

It has been shown that replication of the hepatitis delta virus (HDV) depends on the presence of components of the human RNA ligase, namely RTCB/HSPC117 and DDX1 (Cao et al., RNA. 2009 November; 15 (11):1971-9). Interfering with the tRNA ligase in human cells—by impairing ligase and/or Archease's activity—has a strong effect on the cycle of the virus. Viruses also depend on a functional XBP1 branch of the unfolded protein response, or UPR (Hassan et al., J Biol Chem. 2012 Feb. 10; 287(7):4679-89). Thus by impairing Archease activity, virus infected cells become susceptible to apoptosis or lead to impaired viral development and thus is a therapeutic approach for treating viral infections.

Regarding cancer, it has been reported that multiple myeloma cells heavily rely on a chronically activated UPR in order to generate high levels of the transcription factor XBP1s through unconventional, cytoplasmic splicing—cleavage and ligation—of Xbp1 mRNA. Cleavage is executed by the endonuclease IRE1. The tRNA ligase and Archease together constitute the ligase required for XBP1 mRNA splicing.

Compounds interfering with the endonuclease activity of IRE1 have been developed (Papandreou et al., Blood. 2011 Jan. 27; 117 (4):1311-4.) but showed only limited anti-myeloma activity. The emergence of the tRNA ligase and in particular Archease as factors required for this splicing process provides a new target for the treatment of multiple myeloma.

In FIGS. 16A and 16B it is shown that using HeLa cells partially depleted of Archease by means of shRNAs, levels of spliced Xbp1 (Xbp1s mRNA) could be reduced in comparison with control cells after induction of the UPR with tunicamycin. Furthermore, reduced levels of total Xbp1 mRNA (unspliced and spliced) were observed as the transcription factor XBP1s induces its own expression as well as of EDEM1 mRNA (FIG. 16C), which is a down-stream target specifically transcribed by the action of XPB1s. Importantly, the Archease inhibition system described above can decrease the expression of RTCB and Archease in H929 multiple myeloma cell lines (FIG. 17). These cells should become impaired in Xbp1 mRNA splicing rendering them sensitive to chemotherapeutic agents, e.g. bortezomib.

REFERENCES

Cao et al., RNA. 15 (11):1971-9, 2009.
Carrasco et al. Cancer cell 11, 349-360, 2007.
Fellmann et al., Mol. Cell 41, 733, 2011.
Fonseca et al., Trends Endocrinol Metab 22(7): 266-274, 2011
Hassan et al., J Biol Chem. 10; 287(7):4679-89, 2012.
Papandreou et al., Blood 117, 1311-1314, 2011.
Popow et al. Science (New York, N.Y.) 331, 760-764, 2011.
Popow et al., Cell Mol Life Sci. DOI: 10.1007/s00018-012-0944-2, 2012.
Walter, P., and Ron, D., Science (New York, N.Y. 334, 1081-1086, 2011.
Yee et al., Proceedings of the National Academy of Sciences of the United States of America 99, 1825-1830, 2002.

The invention claimed is:

1. A method for enhancing the ligase activity of a RNA ligase enzyme, wherein the RNA ligase enzyme is a HSPC117, comprising:
   A) providing an Archease protein, and
   B) contacting the RNA ligase enzyme with the Archease protein, wherein the Archease protein guanylates the RNA ligase enzyme with a GTP, and
   C) transferring a first RNA end of an RNA molecule to a second RNA end of an RNA molecule catalyzed by the RNA ligase enzyme,
wherein one or more selected from the Archease, the RNA ligase, the GTP, the RNA molecule having the first RNA end and the RNA molecule having the second RNA end has a label.

2. The method of claim 1, wherein the Archease protein is set forth as in any one of SEQ ID NOs: 24, 25, 26, 27, 28, 29, 30, 31, 32, 33, 34, 35, 36, 37, 38, 39, 40, 41, 42, 43, or 44.

3. The method of claim 1, wherein the HSPC117 molecule is set forth as in any one of SEQ ID NOs: 1, 2, 3, 4, 5, 6, 7, 8, 9, 10, 11, 13, 15, 17, 19, 21, or 23.

4. The method of claim 1 wherein said RNA molecules are mRNA or tRNA molecules.

5. The method of claim 1, wherein the contacting is during or prior to RNA splicing.

6. A method for treating a disease associated with dysfunctional tRNA splicing or dysfunctional UPR in a subject,
   comprising administering a therapeutically effective amount of an Archease molecule to the subject,
   wherein the subject has the disease associated with dysfunctional tRNA splicing or dysfunctional UPR,
   wherein the Archease molecule enhances the ligase activity of an RNA ligase in the subject.

7. The method of claim 6, further comprising administering a therapeutically effective amount of the RNA ligase to the subject.

8. The method of claim 6, wherein the disease is type-II diabetes.

9. The method of claim 6, wherein the RNA ligase is HSPC117.

10. The method of claim 9, wherein HSPC117 is any one of SEQ ID NOs: 1, 2, 3, 4, 5, 6, 7, 8, 9, 10, 11, 13, 15, 17, 19, 21, or 23.

11. The method of claim 6, wherein the archease molecule is archease protein.

12. The method of claim 11, wherein the archease protein is any one of SEQ ID NOs: 24, 25, 26, 27, 28, 29, 30, 31, 32, 33, 34, 35, 36, 37, 38, 39, 40, 41, 42, 43, or 44.

13. The method of claim 6, wherein the archease molecule is a nucleic acid coding for archease protein.

14. The method of claim 1, wherein the label, for any of the Archease and the RNA ligase, is selected from a His tag or a FLAG tag, and/or wherein the label, for any of the GTP, the RNA molecule having the first RNA end and the RNA molecule having the second RNA end is selected from a radioactive label and a fluorescent label.

* * * * *

SEQUENCE LISTING

```
<160> NUMBER OF SEQ ID NOS: 48

<210> SEQ ID NO 1
<211> LENGTH: 505
<212> TYPE: PRT
<213> ORGANISM: Homo sapiens

<400> SEQUENCE: 1

Met Ser Arg Ser Tyr Asn Asp Glu Leu Gln Phe Leu Glu Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
```

165                 170                 175
Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
            195                 200                 205

Ala Arg Ala Lys Lys Arg Gly Leu Pro Gln Leu Gly Thr Leu Gly Ala
        210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
    290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Phe Asp Leu His Val Ile Tyr Asp Val Ser
            340                 345                 350

His Asn Ile Ala Lys Val Glu Gln His Val Val Asp Gly Lys Glu Arg
        355                 360                 365

Thr Leu Leu Val His Arg Lys Gly Ser Thr Arg Ala Phe Pro Pro His
370                 375                 380

His Pro Leu Ile Ala Val Asp Tyr Gln Leu Thr Gly Gln Pro Val Leu
                385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Met Gly Ile Ala Ile Arg Val Ala Ser Pro
    450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
            500                 505

<210> SEQ ID NO 2
<211> LENGTH: 505
<212> TYPE: PRT
<213> ORGANISM: Mus musculus

<400> SEQUENCE: 2

Met Ser Arg Asn Tyr Asn Asp Glu Leu Gln Phe Leu Asp Lys Ile Asn
1               5                   10                  15

Lys Asn Cys Trp Arg Ile Lys Lys Gly Phe Val Pro Asn Met Gln Val
            20                  25                  30

-continued

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Pro Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
    290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Leu Asp Leu His Val Ile Tyr Asp Val Ser
            340                 345                 350

His Asn Ile Ala Lys Val Glu Gln His Val Val Asp Gly Lys Glu Arg
        355                 360                 365

Thr Leu Leu Val His Arg Lys Gly Ser Thr Arg Ala Phe Pro Pro His
    370                 375                 380

His Pro Leu Ile Ala Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Met Gly Ile Ala Ile Arg Val Ala Ser Pro

```
              450                 455                 460
Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                    485                 490                 495

Leu Arg Pro Ile Ala Val Ile Lys Gly
                500                 505

<210> SEQ ID NO 3
<211> LENGTH: 505
<212> TYPE: PRT
<213> ORGANISM: Xenopus leavis

<400> SEQUENCE: 3

Met Ser Arg Ser Tyr Asn Asp Glu Leu Gln Tyr Leu Asp Lys Ile His
1               5                   10                  15

Asn Asn Cys Trp Arg Ile Arg Lys Gly Phe Val Pro Asn Met Gln Val
                20                  25                  30

Glu Gly Val Phe Tyr Val Asn Asp Pro Leu Glu Lys Leu Met Phe Glu
            35                  40                  45

Glu Leu Arg Asn Ala Ser Arg Gly Gly Ala Ala Gly Gly Phe Leu Pro
        50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Glu Asn Pro Asp Ala Val Val Ser
                100                 105                 110

Pro Gly Gly Val Gly Phe Asp Ile Asn Cys Gly Val Arg Leu Leu Arg
            115                 120                 125

Thr Asn Leu Asp Glu Ser Asp Val Gln Pro Val Lys Glu Gln Leu Ala
        130                 135                 140

Gln Ser Met Phe Asp His Ile Pro Val Gly Val Gly Ser Lys Gly Val
145                 150                 155                 160

Ile Pro Met Gly Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Ser Lys Val Ser
        195                 200                 205

Ser Lys Ala Lys Lys Arg Gly Leu Pro Gln Leu Gly Thr Leu Gly Ala
            210                 215                 220

Gly Asn His Tyr Ala Glu Val Gln Val Val Asp Glu Ile Tyr Asp Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Thr Val
        275                 280                 285

Asn Asp Arg Gln Leu Ala Cys Ala Arg Ile Ser Ser Asp Glu Gly Gln
            290                 295                 300

Asp Tyr Leu Lys Gly Met Ala Ala Gly Asn Tyr Ala Trp Val Asn
305                 310                 315                 320
```

```
Arg Ser Ser Met Thr Phe Leu Thr Arg Gln Ala Phe Ser Lys Val Phe
                325                 330                 335

Asn Thr Pro Pro Asp Leu Asp Met His Val Ile Tyr Asp Val Ser
            340                 345                 350

His Asn Ile Ala Lys Val Glu Gln His Val Val Glu Gly Lys Glu Met
            355                 360                 365

Thr Leu Leu Val His Arg Lys Gly Ala Thr Arg Ala Phe Pro Pro His
    370                 375                 380

His Pro Leu Ile Pro Val Asp Tyr Gln Leu Thr Gly Gln Pro Val Leu
385                 390                 395                 400

Ile Gly Gly Thr Met Gly Thr Cys Ser Tyr Val Leu Thr Gly Thr Asp
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Leu Gly Ile Ala Ile Arg Val Ala Ser Pro
    450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
                500                 505

<210> SEQ ID NO 4
<211> LENGTH: 508
<212> TYPE: PRT
<213> ORGANISM: Strongylocentrotus purpuratus

<400> SEQUENCE: 4

Met Ala Ala Thr Val Arg Glu Tyr Lys Glu Leu Lys Tyr Leu Asn
1               5                   10                  15

Lys Leu Ser Asp Asn Cys Trp Gln Ile Lys Lys Gly Phe Val Asp Asn
                20                  25                  30

Met Lys Val Glu Gly Arg Phe Tyr Val Asp Ser Lys Leu Glu Lys Leu
            35                  40                  45

Met Phe Glu Glu Leu Gln Gln Ala Cys Arg Ser Lys Gly Val Gly Gly
    50                  55                  60

Phe Leu Pro Ala Val Lys Gln Ile Ala Asn Val Ala Ala Leu Pro Gly
65                  70                  75                  80

Ile Thr Gly Tyr Ser Ile Gly Leu Pro Asp Ile His Ser Gly Tyr Gly
                85                  90                  95

Phe Ala Ile Gly Asn Met Ala Ala Phe Asp Met Ser Asn Pro Glu Ala
                100                 105                 110

Val Val Ser Pro Gly Gly Val Gly Phe Asp Ile Asn Cys Gly Val Arg
            115                 120                 125

Leu Leu Arg Thr Asn Leu Thr Glu Lys Asp Val Lys Pro Val Lys Glu
    130                 135                 140

Gln Leu Ala Gln Ser Leu Phe Asp His Ile Pro Val Gly Val Gly Ser
145                 150                 155                 160

Lys Gly Val Ile Pro Met Gly Ala Lys Glu Leu Glu Glu Ala Leu Glu
                165                 170                 175

Met Gly Met Asp Trp Ser Leu Arg Glu Gly Tyr Ala Trp Ala Glu Asp
            180                 185                 190
```

```
Lys Glu His Cys Glu Glu Tyr Gly Arg Met Leu Gln Ala Asp Pro Asn
            195                 200                 205

Lys Val Ser Ala Arg Ala Lys Lys Arg Gly Leu Pro Gln Leu Gly Thr
        210                 215                 220

Leu Gly Ala Gly Asn His Tyr Ala Glu Ile Gln Val Asp Glu Ile
225                 230                 235                 240

Tyr Asn Asp His Ala Ala Lys Lys Met Gly Ile Asp Arg Lys Gly Gln
                245                 250                 255

Val Cys Leu Met Ile His Ser Gly Ser Arg Gly Leu Gly His Gln Val
            260                 265                 270

Ala Thr Asp Ala Leu Val Gln Met Glu Lys Ala Met Lys Arg Asp Lys
        275                 280                 285

Ile Glu Val Asn Asp Arg Gln Leu Ala Cys Ala Arg Ile His Ser Gln
    290                 295                 300

Glu Gly Gln Asp Tyr Leu Lys Ala Met Ala Ala Ala Asn Tyr Ala
305                 310                 315                 320

Trp Val Asn Arg Ser Ser Met Thr Phe Leu Thr Arg Gln Ala Phe Ala
                325                 330                 335

Lys Gln Phe Asp Thr Thr Pro Asp Asp Leu Asp Met His Val Ile Tyr
            340                 345                 350

Asp Val Ser His Asn Ile Ala Lys Val Glu Glu His Met Val Asp Gly
        355                 360                 365

Val Gln Lys Thr Leu Leu Val His Arg Lys Gly Ser Thr Arg Ala Phe
    370                 375                 380

Pro Pro His His Pro Leu Ile Pro Val Asp Tyr Gln Met Thr Gly Gln
385                 390                 395                 400

Pro Val Leu Ile Gly Gly Thr Met Gly Thr Cys Ser Tyr Val Leu Thr
                405                 410                 415

Gly Thr Glu Ser Gly Met Ala Thr Thr Tyr Gly Thr Thr Cys His Gly
            420                 425                 430

Ala Gly Arg Ala Trp Ser Arg Ala Lys Ser Arg Arg Asn Leu Asp Tyr
        435                 440                 445

Gln Thr Val Leu Lys Asn Leu His Glu Leu Gly Ile Ser Ile Arg Val
    450                 455                 460

Ala Ser Pro Lys Leu Val Met Glu Glu Ala Pro Glu Ser Tyr Lys Asp
465                 470                 475                 480

Val Thr Ser Val Val Asn Thr Cys His Asp Val Gly Ile Ser Lys Lys
                485                 490                 495

Val Leu Lys Leu Arg Pro Ile Ala Val Ile Lys Gly
            500                 505

<210> SEQ ID NO 5
<211> LENGTH: 506
<212> TYPE: PRT
<213> ORGANISM: Drosophila melanogaster

<400> SEQUENCE: 5

Met Val Val Arg Pro Tyr Asn Asp Glu Leu Arg Tyr Leu Glu Lys Val
1               5                   10                  15

Ser Asp His Cys Trp Arg Ile Lys Lys Gly Phe Gln Pro Asn Met Asn
                20                  25                  30

Val Glu Gly Cys Phe Tyr Val Asn Ser Arg Leu Glu Arg Leu Met Leu
            35                  40                  45

Glu Glu Leu Lys Asn Ser Cys Arg Pro Gly Ala Val Gly Gly Phe Leu
```

```
                50                  55                  60
Pro Gly Val Lys Gln Ile Ala Asn Val Ala Ala Leu Pro Gly Ile Val
 65                  70                  75                  80

Gly Arg Ser Ile Gly Leu Pro Asp Ile His Ser Gly Tyr Gly Phe Ala
                 85                  90                  95

Ile Gly Asn Met Ala Ala Phe Asp Met Asn Asp Pro Leu Ser Val Val
            100                 105                 110

Ser Pro Gly Gly Val Gly Phe Asp Ile Asn Cys Gly Val Arg Leu Leu
            115                 120                 125

Arg Thr Asn Leu Tyr Glu Lys Asp Val Gln Pro Val Lys Glu Gln Leu
        130                 135                 140

Ala Gln Ser Leu Phe Asp His Ile Pro Val Gly Val Gly Ser Lys Gly
145                 150                 155                 160

Ile Ile Pro Met Asn Ala Arg Asp Leu Glu Glu Ala Leu Glu Met Gly
                165                 170                 175

Met Asp Trp Ser Leu Arg Glu Gly Tyr Val Trp Ala Glu Asp Lys Glu
            180                 185                 190

His Cys Glu Glu Tyr Gly Arg Met Leu Asn Ala Asp Pro Ala Lys Val
        195                 200                 205

Ser Met Arg Ala Lys Lys Arg Gly Leu Pro Gln Leu Gly Thr Leu Gly
210                 215                 220

Ala Gly Asn His Tyr Ala Glu Ile Gln Val Val Asp Glu Ile Tyr Asp
225                 230                 235                 240

Lys Trp Ser Ala Ser Lys Met Gly Ile Glu Glu Lys Gly Gln Val Val
                245                 250                 255

Val Met Ile His Ser Gly Ser Arg Gly Phe Gly His Gln Val Ala Thr
            260                 265                 270

Asp Ala Leu Val Gln Met Glu Lys Ala Met Lys Arg Asp Lys Ile Glu
        275                 280                 285

Thr Asn Asp Arg Gln Leu Ala Cys Ala Arg Ile Asn Ser Val Glu Gly
290                 295                 300

Gln Asp Tyr Leu Lys Ala Met Ala Ala Ala Asn Phe Ala Trp Val
305                 310                 315                 320

Asn Arg Ser Ser Met Thr Phe Leu Thr Arg Gln Ala Phe Ala Lys Met
                325                 330                 335

Phe Asn Thr Thr Pro Asp Asp Leu Asp Met His Val Ile Tyr Asp Val
            340                 345                 350

Ser His Asn Ile Ala Lys Val Glu Asn His Met Val Asp Gly Lys Glu
        355                 360                 365

Arg Lys Leu Leu Val His Arg Lys Gly Ser Thr Arg Ala Phe Pro Pro
370                 375                 380

His His Pro Leu Ile Pro Val Asp Tyr Gln Leu Thr Gly Gln Pro Val
385                 390                 395                 400

Leu Val Gly Gly Thr Met Gly Thr Cys Ser Tyr Val Leu Thr Gly Thr
                405                 410                 415

Glu Gln Gly Met Gln Glu Thr Phe Gly Ser Thr Cys His Gly Ala Gly
            420                 425                 430

Arg Ala Leu Ser Arg Ala Lys Ser Arg Arg Asn Leu Asp Tyr Lys Asp
        435                 440                 445

Val Leu Asp Lys Leu Asp Gln Leu Gly Ile Ala Ile Arg Val Ala Ser
450                 455                 460

Pro Lys Leu Val Met Glu Glu Ala Pro Glu Ser Tyr Lys Asp Val Thr
465                 470                 475                 480
```

```
Asp Val Val Asp Thr Cys His Ala Ala Gly Ile Ser Lys Lys Cys Ile
            485                 490                 495

Lys Met Arg Pro Ile Ala Val Ile Lys Gly
        500                 505

<210> SEQ ID NO 6
<211> LENGTH: 505
<212> TYPE: PRT
<213> ORGANISM: Caenorhabditis elegans

<400> SEQUENCE: 6

Met Pro Arg Thr Phe Glu Glu Cys Asp Phe Ile Asp Arg Leu Thr
1               5                   10                  15

Asp Thr Lys Phe Arg Ile Lys Lys Gly Phe Val Pro Asn Met Asn Val
                20                  25                  30

Glu Gly Arg Phe Tyr Val Asn Asn Ser Leu Glu Gln Leu Met Phe Asp
            35                  40                  45

Glu Leu Lys Phe Ser Cys Asp Gly Gln Gly Ile Gly Gly Phe Leu Pro
    50                  55                  60

Ala Val Arg Gln Ile Ala Asn Val Ala Ser Leu Pro Gly Ile Val Gly
65              70                  75                  80

His Ser Ile Gly Leu Pro Asp Ile His Ser Gly Tyr Gly Phe Ser Ile
                85                  90                  95

Gly Asn Ile Ala Ala Phe Asp Val Gly Asn Pro Glu Ser Val Ile Ser
            100                 105                 110

Pro Gly Gly Val Gly Phe Asp Ile Asn Cys Gly Val Arg Leu Leu Arg
        115                 120                 125

Thr Asn Leu Phe Glu Glu Asn Val Lys Pro Leu Lys Glu Gln Leu Thr
130                 135                 140

Gln Ser Leu Phe Asp His Ile Pro Val Gly Val Gly Ser Arg Gly Ala
145                 150                 155                 160

Ile Pro Met Leu Ala Ser Asp Leu Val Glu Cys Leu Glu Met Gly Met
                165                 170                 175

Asp Trp Thr Leu Arg Glu Gly Tyr Ser Trp Ala Glu Asp Lys Glu His
            180                 185                 190

Cys Glu Glu Tyr Gly Arg Met Leu Gln Ala Asp Ala Ser Lys Val Ser
    195                 200                 205

Leu Arg Ala Lys Lys Arg Gly Leu Pro Gln Leu Gly Thr Leu Gly Ala
210                 215                 220

Gly Asn His Tyr Ala Glu Val Gln Val Val Asp Glu Ile Tyr Asp Lys
225                 230                 235                 240

His Ala Ala Ser Thr Met Gly Ile Asp Glu Glu Gly Gln Val Val Val
                245                 250                 255

Met Leu His Cys Gly Ser Arg Gly Leu Gly His Gln Val Ala Thr Asp
            260                 265                 270

Ser Leu Val Glu Met Glu Lys Ala Met Ala Arg Asp Gly Ile Val Val
    275                 280                 285

Asn Asp Lys Gln Leu Ala Cys Ala Arg Ile Asn Ser Val Glu Gly Lys
290                 295                 300

Asn Tyr Phe Ser Gly Met Ala Ala Ala Ala Asn Phe Ala Trp Val Asn
305                 310                 315                 320

Arg Ser Cys Ile Thr Phe Cys Val Arg Asn Ala Phe Gln Lys Thr Phe
                325                 330                 335

Gly Met Ser Ala Asp Asp Met Asp Met Gln Val Ile Tyr Asp Val Ser
```

```
                    340                 345                 350
His Asn Val Ala Lys Met Glu Glu His Met Val Asp Gly Arg Pro Arg
                355                 360                 365

Gln Leu Cys Val His Arg Lys Gly Ala Thr Arg Ala Phe Pro Ala His
        370                 375                 380

His Pro Leu Ile Pro Val Asp Tyr Gln Leu Ile Gly Gln Pro Val Leu
385                 390                 395                 400

Ile Gly Gly Ser Met Gly Thr Cys Ser Tyr Val Leu Thr Gly Thr Glu
                405                 410                 415

Gln Gly Leu Val Glu Thr Phe Gly Thr Thr Cys His Gly Ala Gly Arg
        420                 425                 430

Ala Leu Ser Arg Ala Lys Ser Arg Arg Thr Ile Thr Trp Asp Ser Val
        435                 440                 445

Ile Asp Asp Leu Lys Lys Lys Glu Ile Ser Ile Arg Ile Ala Ser Pro
        450                 455                 460

Lys Leu Ile Met Glu Glu Ala Pro Glu Ser Tyr Lys Asn Val Thr Asp
465                 470                 475                 480

Val Val Asp Thr Cys Asp Ala Ala Gly Ile Ser Lys Lys Ala Val Lys
                485                 490                 495

Leu Arg Pro Ile Ala Val Ile Lys Gly
            500                 505

<210> SEQ ID NO 7
<211> LENGTH: 476
<212> TYPE: PRT
<213> ORGANISM: Chlamydomonas reinhardtii

<400> SEQUENCE: 7

Met His Val Pro Gly Thr Phe Tyr Val Asn Asp Ala Leu Lys Gly Leu
1               5                   10                  15

Leu Phe Glu Glu Leu Gln Gln Ala Val Val Arg Gly Asp His Gly Gly
                20                  25                  30

Phe Leu Pro Ala Val Lys Gln Leu Ala Asn Val Ala Ala Leu Pro Gly
            35                  40                  45

Ile Val Lys Arg Ser Ile Ala Leu Pro Asp Val His Ser Gly Tyr Gly
        50                  55                  60

Phe Ala Ile Gly Asn Val Ala Ala Phe Asp Met Asp Asn Pro Glu Ala
65                  70                  75                  80

Val Val Ser Pro Gly Gly Val Gly Phe Asp Ile Asn Cys Gly Val Arg
                85                  90                  95

Leu Leu Arg Thr Asn Leu Thr Glu Ala Glu Val Gly Pro Val Arg Glu
                100                 105                 110

Gln Leu Ala Gln Ala Leu Phe Asp His Ile Pro Val Gly Val Gly Ser
            115                 120                 125

Gln Gly Ile Ile Pro Thr Thr Ala Lys Asp Met Glu Ser Ala Leu Glu
        130                 135                 140

Leu Gly Met Asp Trp Ser Leu Arg Glu Gly Tyr Ala Trp Ala Glu Asp
145                 150                 155                 160

Lys Glu His Cys Glu Glu Tyr Gly Arg Met Leu Asn Ala Asp Pro Arg
                165                 170                 175

Tyr Val Ser Ser Arg Ala Lys Lys Arg Gly Leu Pro Gln Met Gly Thr
            180                 185                 190

Leu Gly Ala Gly Asn His Tyr Ala Glu Val Gln Val Val Asp Glu Val
        195                 200                 205
```

```
Tyr Asp Ala Val Ala Ala Arg Arg Met Gly Ile Asp Thr Pro Gly Gln
            210                 215                 220

Val Val Val Met Ile His Ser Gly Ser Arg Gly Leu Gly His Gln Val
225                 230                 235                 240

Ala Thr Asp Ala Leu Val Ala Met Glu Arg Ala Met Ala Arg Asp Gly
                245                 250                 255

Ile Ile Thr Asn Asp Arg Gln Leu Ala Cys Ala Arg Ile Asn Ser Glu
                260                 265                 270

Glu Gly Gln Ala Tyr Leu Lys Ala Met Ser Cys Ala Ala Asn Tyr Ala
                275                 280                 285

Trp Val Asn Arg Ser Ser Met Thr Phe Leu Ala Arg Gln Ala Phe Ala
290                 295                 300

Lys Ile Phe Lys Ser Thr Pro Asp Asp Leu Asp Met His Val Val Tyr
305                 310                 315                 320

Asp Val Ser His Asn Ile Ala Lys Val Glu Gln His Cys Val Asp Gly
                325                 330                 335

Gln His Arg Arg Leu Leu Val His Arg Lys Gly Ser Thr Arg Ala Phe
                340                 345                 350

Pro Pro His His Pro Leu Ile Pro Ala Asp Tyr Gln Leu Ile Gly Gln
                355                 360                 365

Pro Val Leu Val Gly Gly Thr Met Gly Thr Ser Ser Tyr Val Leu Thr
370                 375                 380

Gly Thr Glu Gln Gly Phe Thr Glu Thr Phe Gly Ser Thr Cys His Gly
385                 390                 395                 400

Ala Gly Arg Ala Arg Ser Arg Asn Asn Ser Arg Asn Lys Leu Asp Tyr
                405                 410                 415

Gln Asp Val Leu Asp Asn Leu Lys Ala Lys Gly Ile Ala Ile Arg Val
                420                 425                 430

Ala Ser Pro Lys Leu Val Met Glu Glu Ala Pro Glu Ser Tyr Lys Asp
                435                 440                 445

Val Ser Glu Val Val Asp Thr Cys His Gln Ala Gly Ile Ser Lys Lys
                450                 455                 460

Ala Val Lys Leu Arg Pro Ile Ala Val Ile Lys Gly
465                 470                 475

<210> SEQ ID NO 8
<211> LENGTH: 480
<212> TYPE: PRT
<213> ORGANISM: Methanocaldococcus jannaschii

<400> SEQUENCE: 8

Met Lys Asp Val Leu Lys Arg Val Ser Asp Val Val Trp Glu Leu Pro
1               5                   10                  15

Lys Asp Tyr Lys Asp Cys Met Arg Val Pro Gly Arg Ile Tyr Leu Asn
                20                  25                  30

Glu Ile Leu Leu Asp Glu Leu Glu Pro Glu Val Leu Glu Gln Ile Ala
            35                  40                  45

Asn Val Ala Cys Leu Pro Gly Ile Tyr Lys Tyr Ser Ile Ala Met Pro
        50                  55                  60

Asp Val His Tyr Gly Tyr Gly Phe Ala Ile Gly Gly Val Ala Ala Phe
65              70                  75                  80

Asp Gln Arg Glu Gly Val Ile Ser Pro Gly Gly Val Gly Phe Asp Ile
                85                  90                  95

Asn Cys Gly Val Arg Leu Ile Arg Thr Asn Leu Thr Lys Glu Glu Val
                100                 105                 110
```

Gln Ser Lys Ile Lys Glu Leu Ile Lys Thr Leu Phe Lys Asn Val Pro
            115                 120                 125

Ser Gly Leu Gly Ser Lys Gly Ile Leu Lys Phe Ser Lys Ser Val Met
            130                 135                 140

Asp Asp Val Leu Glu Glu Gly Val Arg Trp Ala Val Lys Glu Gly Tyr
145                 150                 155                 160

Gly Trp Lys Glu Asp Leu Glu Phe Ile Glu Glu His Gly Cys Leu Lys
                165                 170                 175

Asp Ala Asp Ala Ser Tyr Val Ser Asp Lys Ala Lys Glu Arg Gly Arg
            180                 185                 190

Val Gln Leu Gly Ser Leu Gly Ser Gly Asn His Phe Leu Glu Val Gln
            195                 200                 205

Tyr Val Glu Lys Val Phe Asp Glu Glu Ala Ala Glu Ile Tyr Gly Ile
            210                 215                 220

Glu Glu Asn Gln Val Val Leu Val His Thr Gly Ser Arg Gly Leu
225                 230                 235                 240

Gly His Gln Ile Cys Thr Asp Tyr Leu Arg Ile Met Glu Lys Ala Ala
                245                 250                 255

Lys Asn Tyr Gly Ile Lys Leu Pro Asp Arg Gln Leu Ala Cys Ala Pro
            260                 265                 270

Phe Glu Ser Glu Glu Gly Gln Ser Tyr Phe Lys Ala Met Cys Cys Gly
            275                 280                 285

Ala Asn Tyr Ala Trp Ala Asn Arg Gln Met Ile Thr His Trp Val Arg
            290                 295                 300

Glu Ser Phe Glu Glu Val Phe Lys Ile His Ala Glu Asp Leu Glu Met
305                 310                 315                 320

Asn Ile Val Tyr Asp Val Ala His Asn Ile Ala Lys Lys Glu Glu His
                325                 330                 335

Ile Ile Asp Gly Arg Lys Val Lys Val Ile His Arg Lys Gly Ala
            340                 345                 350

Thr Arg Ala Phe Pro Pro Lys His Glu Ala Ile Pro Lys Glu Tyr Trp
            355                 360                 365

Ser Val Gly Gln Pro Val Ile Ile Pro Gly Asp Met Gly Thr Ala Ser
            370                 375                 380

Tyr Leu Met Arg Gly Thr Glu Ile Ala Met Lys Glu Thr Phe Gly Ser
385                 390                 395                 400

Thr Ala His Gly Ala Gly Arg Lys Leu Ser Arg Ala Lys Ala Leu Lys
                405                 410                 415

Leu Trp Lys Gly Lys Glu Ile Gln Arg Arg Leu Ala Glu Met Gly Ile
            420                 425                 430

Val Ala Met Ser Asp Ser Lys Ala Val Met Ala Glu Glu Ala Pro Glu
            435                 440                 445

Ala Tyr Lys Ser Val Asp Leu Val Ala Asp Thr Cys His Lys Ala Gly
            450                 455                 460

Ile Ser Leu Lys Val Ala Arg Met Arg Pro Leu Gly Val Ile Lys Gly
465                 470                 475                 480

<210> SEQ ID NO 9
<211> LENGTH: 481
<212> TYPE: PRT
<213> ORGANISM: Pyrococcus horikoshii

<400> SEQUENCE: 9

Met Val Val Pro Leu Lys Arg Ile Asp Lys Ile Arg Trp Glu Ile Pro

-continued

```
1               5                   10                  15
Lys Phe Asp Lys Arg Met Arg Val Pro Gly Arg Val Tyr Ala Asp Glu
                20                  25                  30
Val Leu Leu Glu Lys Met Lys Asn Asp Arg Thr Leu Glu Gln Ala Thr
                35                  40                  45
Asn Val Ala Met Leu Pro Gly Ile Tyr Lys Tyr Ser Ile Val Met Pro
                50                  55                  60
Asp Gly His Gln Gly Tyr Gly Phe Pro Ile Gly Gly Val Ala Ala Phe
65                  70                  75                  80
Asp Val Lys Glu Gly Val Ile Ser Pro Gly Gly Ile Gly Tyr Asp Ile
                85                  90                  95
Asn Cys Gly Val Arg Leu Ile Arg Thr Asn Leu Thr Glu Lys Glu Val
                100                 105                 110
Arg Pro Arg Ile Lys Gln Leu Val Asp Thr Leu Phe Lys Asn Val Pro
                115                 120                 125
Ser Gly Val Gly Ser Gln Gly Arg Ile Lys Leu His Trp Thr Gln Ile
                130                 135                 140
Asp Asp Val Leu Val Asp Gly Ala Lys Trp Ala Val Asp Asn Gly Tyr
145                 150                 155                 160
Gly Trp Glu Arg Asp Leu Glu Arg Leu Glu Gly Gly Arg Met Glu
                165                 170                 175
Gly Ala Asp Pro Glu Ala Val Ser Gln Arg Ala Lys Gln Arg Gly Ala
                180                 185                 190
Pro Gln Leu Gly Ser Leu Gly Ser Gly Asn His Phe Leu Glu Val Gln
                195                 200                 205
Val Val Asp Lys Ile Phe Asp Pro Glu Val Ala Lys Ala Tyr Gly Leu
                210                 215                 220
Phe Glu Gly Gln Val Val Met Val His Thr Gly Ser Arg Gly Leu
225                 230                 235                 240
Gly His Gln Val Ala Ser Asp Tyr Leu Arg Ile Met Glu Arg Ala Ile
                245                 250                 255
Arg Lys Tyr Arg Ile Pro Trp Pro Asp Arg Glu Leu Val Ser Val Pro
                260                 265                 270
Phe Gln Ser Glu Glu Gly Gln Arg Tyr Phe Ser Ala Met Lys Ala Ala
                275                 280                 285
Ala Asn Phe Ala Trp Ala Asn Arg Gln Met Ile Thr His Trp Val Arg
                290                 295                 300
Glu Ser Phe Gln Glu Val Phe Lys Gln Asp Pro Glu Gly Asp Leu Gly
305                 310                 315                 320
Met Asp Ile Val Tyr Asp Val Ala His Asn Ile Gly Lys Val Glu Glu
                325                 330                 335
His Glu Val Asp Gly Lys Arg Val Lys Val Ile Val His Arg Lys Gly
                340                 345                 350
Ala Thr Arg Ala Phe Pro Pro Gly His Glu Ala Val Pro Arg Leu Tyr
                355                 360                 365
Arg Asp Val Gly Gln Pro Val Leu Ile Pro Gly Ser Met Gly Thr Ala
                370                 375                 380
Ser Tyr Ile Leu Ala Gly Thr Glu Gly Ala Met Lys Glu Thr Phe Gly
385                 390                 395                 400
Ser Thr Cys His Gly Ala Gly Arg Val Leu Ser Arg Lys Ala Ala Thr
                405                 410                 415
Arg Gln Tyr Arg Gly Asp Arg Ile Arg Gln Glu Leu Leu Asn Arg Gly
                420                 425                 430
```

Ile Tyr Val Arg Ala Ala Ser Met Arg Val Ala Glu Glu Ala Pro
        435                 440                 445

Gly Ala Tyr Lys Asn Val Asp Asn Val Val Lys Val Val Ser Glu Ala
465         450                 455                 460

Gly Ile Ala Lys Leu Val Ala Arg Met Arg Pro Ile Gly Val Ala Lys
465                 470                 475                 480

Gly

<210> SEQ ID NO 10
<211> LENGTH: 476
<212> TYPE: PRT
<213> ORGANISM: Thermus thermophilus

<400> SEQUENCE: 10

Met Phe Phe Glu Lys Ile Ala Pro Tyr Thr Tyr Arg Ile Pro Arg Gln
1               5                   10                  15

Gly Lys Met Arg Val Asp Ala Val Phe Phe Ala Ser Lys Glu Ile Leu
            20                  25                  30

Lys Asp Leu Glu Ala Glu Asn Tyr Ala Ser Leu Gln Gln Leu Met Asn
        35                  40                  45

Val Ala Thr Leu Pro Gly Ile Val Glu Pro Ala Leu Ala Met Pro Asp
    50                  55                  60

Ile His Trp Gly Tyr Gly Phe Pro Ile Gly Gly Val Ala Ala Phe Asp
65                  70                  75                  80

Pro Glu Glu Gly Gly Val Val Ser Pro Gly Gly Val Gly Phe Asp Ile
                85                  90                  95

Asn Cys Gly Val Arg Leu Leu Ala Ser His Leu Thr Leu Glu Asp Leu
            100                 105                 110

Leu Pro Arg Gln Lys Glu Leu Ala Asp Ala Leu Tyr Arg Leu Val Pro
        115                 120                 125

Ser Gly Val Gly Ser Glu Arg Arg Asp Val Arg Phe Ser Lys Arg Glu
    130                 135                 140

Leu Lys Glu Ile Leu Lys Glu Gly Ala Gly Trp Leu Val Lys Arg Gly
145                 150                 155                 160

Tyr Gly Tyr Pro Glu Asp Val Arg Phe Ile Glu Ser Gln Gly Arg Leu
                165                 170                 175

Pro Trp Ala Asn Pro Asp Lys Val Ser Glu Arg Ala Phe Glu Arg Gly
            180                 185                 190

Ala Pro Gln Ile Gly Thr Leu Gly Ser Gly Asn His Phe Leu Glu Val
        195                 200                 205

Gln Tyr Val Asp Glu Val Tyr Asp Glu Glu Ala Ala Leu Ala Phe Gly
    210                 215                 220

Leu Phe Lys Gly Gln Val Thr Val Leu Ile His Thr Gly Ser Arg Gly
225                 230                 235                 240

Leu Gly His Gln Val Cys Gln Asp Tyr Val Glu Arg Phe Leu Lys Val
                245                 250                 255

Ala Pro Arg Tyr Gly Ile Glu Leu Val Asp Lys Gln Leu Ala Ala Ala
            260                 265                 270

Pro Ile Lys Ser Pro Glu Gly Gln Asp Tyr Leu Gln Ala Met Ala Ala
        275                 280                 285

Ala Ala Asn Phe Ala Phe Ala Asn Arg Gln Leu Ile Ala His Phe Val
    290                 295                 300

Arg Glu Ala Phe Glu Lys Val Gly Phe Thr Pro Arg Asp His Gly Leu
305                 310                 315                 320

```
Arg Val Leu Tyr Asp Leu Ala His Asn Asn Ala Lys Phe Glu Glu His
                325                 330                 335

Arg Gly Arg Arg Val Leu Val His Arg Lys Gly Ala Thr Arg Ala Phe
            340                 345                 350

Gly Pro Gly His Pro Glu Val Pro Glu Glu Tyr Arg Arg Val Gly Gln
        355                 360                 365

Pro Val Leu Val Pro Gly Asp Met Gly Arg Tyr Ser Tyr Val Leu Ala
    370                 375                 380

Gly Thr Glu Lys Ala Met Glu Val Ser Phe Gly Ser Ser Cys His Gly
385                 390                 395                 400

Ala Gly Arg Lys Met Ser Arg His Gln Ala Lys Lys Val Ala Arg Glu
                405                 410                 415

Arg Asn Leu Val Lys Glu Leu Ala Glu Arg Gly Ile Leu Val Arg Ala
            420                 425                 430

Ala Thr Arg Ala Thr Val Asp Glu Glu Met Pro Glu Ala Tyr Lys Asp
        435                 440                 445

Val Ser Leu Val Val Glu Ala Val Glu Gly Ala Gly Ile Gly Lys Lys
    450                 455                 460

Val Ala Arg Leu Arg Pro Leu Ile Val Val Lys Gly
465                 470                 475

<210> SEQ ID NO 11
<211> LENGTH: 408
<212> TYPE: PRT
<213> ORGANISM: Escherichia coli

<400> SEQUENCE: 11

Met Asn Tyr Glu Leu Leu Thr Thr Glu Asn Ala Pro Val Lys Met Trp
1               5                   10                  15

Thr Lys Gly Val Pro Val Glu Ala Asp Ala Arg Gln Gln Leu Ile Asn
                20                  25                  30

Thr Ala Lys Met Pro Phe Ile Phe Lys His Ile Ala Val Met Pro Asp
            35                  40                  45

Val His Leu Gly Lys Gly Ser Thr Ile Gly Ser Val Ile Pro Thr Lys
        50                  55                  60

Gly Ala Ile Ile Pro Ala Ala Val Gly Val Asp Ile Gly Cys Gly Met
65                  70                  75                  80

Asn Ala Leu Arg Thr Ala Leu Thr Ala Glu Asp Leu Pro Glu Asn Leu
                85                  90                  95

Ala Glu Leu Arg Gln Ala Ile Glu Thr Ala Val Pro His Gly Arg Thr
            100                 105                 110

Thr Gly Arg Cys Lys Arg Asp Lys Gly Ala Trp Glu Asn Pro Pro Val
        115                 120                 125

Asn Val Asp Ala Lys Trp Ala Glu Leu Glu Ala Gly Tyr Gln Trp Leu
    130                 135                 140

Thr Gln Lys Tyr Pro Arg Phe Leu Asn Thr Asn Asn Tyr Lys His Leu
145                 150                 155                 160

Gly Thr Leu Gly Thr Gly Asn His Phe Ile Glu Ile Cys Leu Asp Glu
                165                 170                 175

Ser Asp Gln Val Trp Ile Met Leu His Ser Gly Ser Arg Gly Ile Gly
            180                 185                 190

Asn Ala Ile Gly Thr Tyr Phe Ile Asp Leu Ala Gln Lys Glu Met Gln
        195                 200                 205

Glu Thr Leu Glu Thr Leu Pro Ser Arg Asp Leu Ala Tyr Phe Met Glu
```

```
        210                 215                 220
Gly Thr Glu Tyr Phe Asp Asp Tyr Leu Lys Ala Val Ala Trp Ala Gln
225                 230                 235                 240

Leu Phe Ala Ser Leu Asn Arg Asp Ala Met Met Glu Asn Val Val Thr
                245                 250                 255

Ala Leu Gln Ser Ile Thr Gln Lys Thr Val Arg Gln Pro Gln Thr Leu
                260                 265                 270

Ala Met Glu Glu Ile Asn Cys His His Asn Tyr Val Gln Lys Glu Gln
            275                 280                 285

His Phe Gly Glu Glu Ile Tyr Val Thr Arg Lys Gly Ala Val Ser Ala
            290                 295                 300

Arg Ala Gly Gln Tyr Gly Ile Ile Pro Gly Ser Met Gly Ala Lys Ser
305                 310                 315                 320

Phe Ile Val Arg Gly Leu Gly Asn Glu Glu Ser Phe Cys Ser Cys Ser
                325                 330                 335

His Gly Ala Gly Arg Val Met Ser Arg Thr Lys Ala Lys Lys Leu Phe
            340                 345                 350

Ser Val Glu Asp Gln Ile Arg Ala Thr Ala His Val Glu Cys Arg Lys
            355                 360                 365

Asp Ala Glu Val Ile Asp Glu Ile Pro Met Ala Tyr Lys Asp Ile Asp
            370                 375                 380

Ala Val Met Ala Ala Gln Ser Asp Leu Val Glu Val Ile Tyr Thr Leu
385                 390                 395                 400

Arg Gln Val Val Cys Val Lys Gly
                405
```

<210> SEQ ID NO 12
<211> LENGTH: 1518
<212> TYPE: DNA
<213> ORGANISM: Homo sapiens

<400> SEQUENCE: 12

```
atgagtcgca gctataatga tgagctgcag ttcttggaga agatcaataa aaactgctgg      60
aggatcaaga agggcttcgt gcccaacatg caggttgaag tgttttctta tgtgaatgat     120
gctctggaga aattgatgtt tgaggaatta aggaatgcct gtcgaggtgg tgtgttggt      180
ggcttcctgc cagccatgaa acagattggc aatgtgcag cctgcctgg aattgttcat      240
cgatctattg gcttcctga tgtccattca ggatatgggt ttgctattgg gaacatggca     300
gcctttgata tgaatgaccc tgaagcagta gtatccccag gtggtgtcgg gtttgacatc    360
aactgtggtg tccgcttgct aagaaccaat ttagatgaaa gtgatgtcca gcctgtgaag    420
gagcaacttg cccaagctat gtttgaccac attcctgttg gggtggggtc aaaaggtgtc    480
atcccaatga atgccaaaga cttggaggag gccttggaga tggggtgga ctggtcctta    540
agagaagggt atgcctgggc tgaagacaag gagcactgcg aggagtacgg aaggatgctg    600
caggctgacc ccaataaagt ttctgcaagg gcgaagaaaa gaggccttcc tcagttgggg    660
accctgggag caggcaacca ttatgcagaa atccaggttg tggatgagat tttcaatgag    720
tatgctgcta aaaaaatggg catcgaccat aagggacagg tgtgtgtgat gatccacagt    780
ggaagcagag gcttgggcca ccaagtagcc acagatgcgc tggtagctat ggagaaggcc    840
atgaagagag acaagattat agtcaatgat cggcagttgg cttgtgctcg aatcgcttcc    900
ccagagggtc aagactatct gaagggaatg gcagctgctg gaactatgc ctgggtcaac    960
cgctcttcca tgaccttctt aaacccgtcag gctttcgcca aggtcttcaa cacaaccct    1020
```

```
gatgacttgg acctacatgt gatttatgat gtttctcaca acattgccaa agtggagcag    1080
catgtggtgg acggaaagga acggacactg ttagtacaca ggaagggatc cacccgcgct    1140
ttccctcctc accatcccct cattgctgtt gattaccaac tcactggaca gccagtgctc    1200
attggtggca ccatgggaac ctgtagttat gttcttactg gcactgaaca gggcatgact    1260
gagacctttg gaacaacctg tcatggagcg ggccgtgcat tgtcccgagc aaaatctcga    1320
cgtaatttag atttccagga tgtcttagac aaattggcag atatgggaat tgcgatccgt    1380
gttgcctcac ccaaactggt tatggaagag ctcctgagt cctataagaa tgtgacagat    1440
gtggtaaata cctgccatga tgctggaatc agcaagaaag ccattaaact gagaccaatt    1500
gctgtgatca aaggatag                                                 1518
```

<210> SEQ ID NO 13  
<211> LENGTH: 505  
<212> TYPE: PRT  
<213> ORGANISM: Homo sapiens

<400> SEQUENCE: 13

```
Met Ser Arg Ser Tyr Asn Asp Glu Leu Gln Phe Leu Glu Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Ala Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
```

```
                   275                 280                 285
Asn Asp Arg Gln Leu Ala Cys Ala Arg Ile Ala Ser Pro Glu Gly Gln
    290                 295                 300
Asp Tyr Leu Lys Gly Met Ala Ala Gly Asn Tyr Ala Trp Val Asn
305                 310                 315                 320
Arg Ser Ser Met Thr Phe Leu Thr Arg Gln Ala Phe Ala Lys Val Phe
                325                 330                 335
Asn Thr Thr Pro Asp Asp Leu Asp Leu His Val Ile Tyr Asp Val Ser
            340                 345                 350
His Asn Ile Ala Lys Val Glu Gln His Val Val Asp Gly Lys Glu Arg
        355                 360                 365
Thr Leu Leu Val His Arg Lys Gly Ser Thr Arg Ala Phe Pro Pro His
    370                 375                 380
His Pro Leu Ile Ala Val Asp Tyr Gln Leu Thr Gly Gln Pro Val Leu
385                 390                 395                 400
Ile Gly Gly Thr Met Gly Thr Cys Ser Tyr Val Leu Thr Gly Thr Glu
                405                 410                 415
Gln Gly Met Thr Glu Thr Phe Gly Thr Thr Cys His Gly Ala Gly Arg
            420                 425                 430
Ala Leu Ser Arg Ala Lys Ser Arg Arg Asn Leu Asp Phe Gln Asp Val
        435                 440                 445
Leu Asp Lys Leu Ala Asp Met Gly Ile Ala Ile Arg Val Ala Ser Pro
    450                 455                 460
Lys Leu Val Met Glu Glu Ala Pro Glu Ser Tyr Lys Asn Val Thr Asp
465                 470                 475                 480
Val Val Asn Thr Cys His Asp Ala Gly Ile Ser Lys Lys Ala Ile Lys
                485                 490                 495
Leu Arg Pro Ile Ala Val Ile Lys Gly
            500                 505

<210> SEQ ID NO 14
<211> LENGTH: 1521
<212> TYPE: DNA
<213> ORGANISM: Drosophila melanogaster

<400> SEQUENCE: 14
atggtggtgc gtccgtacaa cgatgagctc cggtacctgg agaaagtgag cgaccactgc      60
tggcgcatca agaagggctt ccagccaaat atgaatgtgg aggggtgttt ctatgtgaac     120
agccggctgg agcgcctgat gctggaggag ctgaagaact cctgtcgccc gggcgcagtg     180
ggtggcttcc tgcctggcgt caagcagata gccaatgtgg ccgcgttgcc gggcatcgtg     240
ggcaggtcca ttggactgcc cgacattcat tccggctacg gatttgccat cgggaacatg     300
gctgctttcg acatgaacga tccgctgtcc gttgtaagtc ccggcggcgt gggtttcgac     360
atcaactgtg gcgtgcgtct gctgcgcacg aatctgtacg agaaggatgt gcagccggtg     420
aaggagcaac tggcgcagtc cctgttcgat cacataccg tgggtgtggg ctccaagggc      480
atcataccca tgaatgcccg cgatctggag gaggccctcg aaatgggcat ggactggtcg     540
ctgcgcgagg gatacgtgtg gcggaggac aaggagcatt gcgaggagta cggccgcatg      600
ctgaacgccg atcccgccaa ggtgagcatg cgggccaaga gcgagggct gccccagctg      660
ggcactctgg gtgcgggcaa tcactacgcc gagatccagg tggtggacga aatctacgac     720
aagtggagcg cctccaagat gggcatcgag gagaagggcc aggtggtggt gatgattcac     780
tcgggcagtc gtggcttcgg ccaccaggtc gctaccgacg ccctggtcca gatggagaag     840
```

```
gccatgaagc gggacaagat cgagaccaat gaccggcagc tggcctgcgc caggatcaat    900
tcggtggagg acaggacta cttgaaggcc atggcggcgg ctgcgaactt tgcctgggtg    960
aatcgcagct ccatgacatt cctcacccgt caagcgtttg ccaagatgtt aacaccaca   1020
cccgatgatc tcgacatgca cgttatctat gactttcgc acaatattgc caaggtggag   1080
aaccacatgg tggacggcaa ggagcggaag ctgttggttc accggaaggg ctccacgcgc   1140
gccttcccgc cacaccatcc cctgatccca gtggactatc agcttaccgg cagccagtc   1200
ctcgtcggtg aaccatggg cacttgcagt acgtgctaa ctggaacgga cagggcatg    1260
caggagacgt tcggtagcac ttgccacgga gcgggtcgtg cactatctcg agccaaatcc   1320
cggcgcaatc tggactacaa ggatgtgctg acaagctgg accagttggg catcgccata   1380
cgcgtggcct cgcccaaact ggtcatggag gaggcacccg aatcttacaa ggacgtgacc   1440
gatgtggtcg acacctgtca cgcagctggc atcagcaaaa agtgcatcaa gatgcgccca   1500
attgcagtta tcaagggcta a                                            1521
```

<210> SEQ ID NO 15
<211> LENGTH: 506
<212> TYPE: PRT
<213> ORGANISM: Drosophila melanogaster

<400> SEQUENCE: 15

```
Met Val Val Arg Pro Tyr Asn Asp Glu Leu Arg Tyr Leu Glu Lys Val
1               5                   10                  15

Ser Asp His Cys Trp Arg Ile Lys Lys Gly Phe Gln Pro Asn Met Asn
            20                  25                  30

Val Glu Gly Cys Phe Tyr Val Asn Ser Arg Leu Glu Arg Leu Met Leu
        35                  40                  45

Glu Glu Leu Lys Asn Ser Cys Arg Pro Gly Ala Val Gly Gly Phe Leu
    50                  55                  60

Pro Gly Val Lys Gln Ile Ala Asn Val Ala Ala Leu Pro Gly Ile Val
65                  70                  75                  80

Gly Arg Ser Ile Gly Leu Pro Asp Ile His Ser Gly Tyr Gly Phe Ala
                85                  90                  95

Ile Gly Asn Met Ala Ala Phe Asp Met Asn Asp Pro Leu Ser Val Val
            100                 105                 110

Ser Pro Gly Gly Val Gly Phe Asp Ile Asn Cys Gly Val Arg Leu Leu
        115                 120                 125

Arg Thr Asn Leu Tyr Glu Lys Asp Val Gln Pro Val Lys Glu Gln Leu
    130                 135                 140

Ala Gln Ser Leu Phe Asp His Ile Pro Val Gly Val Gly Ser Lys Gly
145                 150                 155                 160

Ile Ile Pro Met Asn Ala Arg Asp Leu Glu Glu Ala Leu Glu Met Gly
                165                 170                 175

Met Asp Trp Ser Leu Arg Glu Gly Tyr Val Trp Ala Glu Asp Lys Glu
            180                 185                 190

His Cys Glu Glu Tyr Gly Arg Met Leu Asn Ala Asp Pro Ala Lys Val
        195                 200                 205

Ser Met Arg Ala Lys Lys Arg Gly Leu Pro Gln Leu Gly Thr Leu Gly
    210                 215                 220

Ala Gly Asn His Tyr Ala Glu Ile Gln Val Val Asp Glu Ile Tyr Asp
225                 230                 235                 240

Lys Trp Ser Ala Ser Lys Met Gly Ile Glu Glu Lys Gly Gln Val Val
```

```
                   245                 250                 255
     Val Met Ile His Ser Gly Ser Arg Gly Phe Gly His Gln Val Ala Thr
                 260                 265                 270

Asp Ala Leu Val Gln Met Glu Lys Ala Met Lys Arg Asp Lys Ile Glu
             275                 280                 285

Thr Asn Asp Arg Gln Leu Ala Cys Ala Arg Ile Asn Ser Val Glu Gly
         290                 295                 300

Gln Asp Tyr Leu Lys Ala Met Ala Ala Ala Asn Phe Ala Trp Val
     305                 310                 315                 320

Asn Arg Ser Ser Met Thr Phe Leu Thr Arg Gln Ala Phe Ala Lys Met
                     325                 330                 335

Phe Asn Thr Thr Pro Asp Asp Leu Asp Met His Val Ile Tyr Asp Val
                 340                 345                 350

Ser His Asn Ile Ala Lys Val Glu Asn His Met Val Asp Gly Lys Glu
             355                 360                 365

Arg Lys Leu Leu Val His Arg Lys Gly Ser Thr Arg Ala Phe Pro Pro
         370                 375                 380

His His Pro Leu Ile Pro Val Asp Tyr Gln Leu Thr Gly Gln Pro Val
     385                 390                 395                 400

Leu Val Gly Gly Thr Met Gly Thr Cys Ser Tyr Val Leu Thr Gly Thr
                     405                 410                 415

Glu Gln Gly Met Gln Glu Thr Phe Gly Ser Thr Cys His Gly Ala Gly
                 420                 425                 430

Arg Ala Leu Ser Arg Ala Lys Ser Arg Arg Asn Leu Asp Tyr Lys Asp
             435                 440                 445

Val Leu Asp Lys Leu Asp Gln Leu Gly Ile Ala Ile Arg Val Ala Ser
         450                 455                 460

Pro Lys Leu Val Met Glu Glu Ala Pro Glu Ser Tyr Lys Asp Val Thr
     465                 470                 475                 480

Asp Val Val Asp Thr Cys His Ala Ala Gly Ile Ser Lys Lys Cys Ile
                     485                 490                 495

Lys Met Arg Pro Ile Ala Val Ile Lys Gly
                 500                 505

<210> SEQ ID NO 16
<211> LENGTH: 1518
<212> TYPE: DNA
<213> ORGANISM: Danio rerio

<400> SEQUENCE: 16
atgagtcgct cttacaacga tgagctccag tatctggata aaatacacaa aaactgctgg      60
cggatcaaga agggtttcgt gccgaatatg ctggtggaag gagtgtttta tgtcaatgac     120
ccgctggaaa agctgatgtt cgaggagctg agaaacgcct gtcgcggagg agggtttgga     180
ggtttcttac ctgcgatgaa gcagattgga aatgtggccg ctctgccagg aatcgtgcac     240
cggtcgatcg gtttaccgga cgttcactca ggatacggat cgctatcgg gaacatggca     300 gcgttcgaca tggagaatcc ggacgcagtc gtctctccag gcggtgtggg tttcgatatt     360
aactgtggtg ttcgtctgct cgcacaaac ctggatgagg cgacgttca gccggtgaag     420 gagcagctgg cacagtctct cttcgaccac atccctgtcg agtcggctc caagggcgtc     480 attcctatgg gtgcaaagga cctggaggag gcgttggaga tgggtgtgga ctggtctctg     540
agggagggat atgcctgggc ggaggataaa gagcactgtg aggagtacgg acgcatgctg     600
caggccgacc caaacaaagt ctcctccaaa gccaagaaga gaggactgcc acagttggga     660
```

```
actctgggtg caggaaacca ctacgcagag attcaggtgg tggacgagat ctacaatgat      720
tacgccgcca agaagatggg catcgatcat aaagggcagg tgtgtgtgat gatccacagc      780
ggcagccgag gactcggaca tcaggtggcc accgacgctc tggtggcgat ggagaaggcc      840
atgaagcgcg accgcatcac agtaaacgac cggcagctag cgtgcgcgcg catcacgtca      900
gaagagggac aggattatct gaagggaatg gcggcagcag gaaactacgc ctgggtcaac      960
cgatcctcca tgaccttcct cacacgcacg gcgttctcca aagtgttcag caccacacca     1020
gatgatctgg acatgcacgt gatctacgac gtctcgcaca acatcgccaa agtggaggag     1080
cacatggtgg acgccggca gaaaacactg ctggtgcata ggaagggctc caccagagcg     1140
tttcctccac accatccact catacctgta gactatcagc tgaccggtca gccagtcctg     1200
attggaggaa ccatgggcac ctgcagttac gtgctcacag gcacagagca gggcatgaca     1260
gagacgttcg gcaccacatg tcacggcgct ggccgagctt atccagagc caaatccaga     1320 cgcaacctgg acttccagga tgttctggat aaactggcag acatgggcat cgctattaga     1380
gtggcgtcac cgaagctggt gatggaggag ctcccgagt cctacaagaa cgtgacagac     1440
gtggtgaaca catgccatga tgccggcatc agcaaaaaag ccatcaaact cagacccatc     1500
gctgtgatta aaggttaa                                                   1518
```

<210> SEQ ID NO 17
<211> LENGTH: 505
<212> TYPE: PRT
<213> ORGANISM: Danio rerio

<400> SEQUENCE: 17

```
Met Ser Arg Ser Tyr Asn Asp Glu Leu Gln Tyr Leu Asp Lys Ile His
1               5                   10                  15

Lys Asn Cys Trp Arg Ile Lys Lys Gly Phe Val Pro Asn Met Leu Val
            20                  25                  30

Glu Gly Val Phe Tyr Val Asn Asp Pro Leu Glu Lys Leu Met Phe Glu
        35                  40                  45

Glu Leu Arg Asn Ala Cys Arg Gly Gly Phe Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Glu Asn Pro Asp Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Gly Asp Val Gln Pro Val Lys Glu Gln Leu Ala
    130                 135                 140

Gln Ser Leu Phe Asp His Ile Pro Val Gly Val Gly Ser Lys Gly Val
145                 150                 155                 160

Ile Pro Met Gly Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Ser Lys Ala Lys Lys Arg Gly Leu Pro Gln Leu Gly Thr Leu Gly Ala
```

```
                210                 215                 220
Gly Asn His Tyr Ala Glu Ile Gln Val Val Asp Glu Ile Tyr Asn Asp
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Arg Ile Thr Val
        275                 280                 285

Asn Asp Arg Gln Leu Ala Cys Ala Arg Ile Thr Ser Glu Glu Gly Gln
290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ser Lys Val Phe
                325                 330                 335

Ser Thr Thr Pro Asp Asp Leu Asp Met His Val Ile Tyr Asp Val Ser
            340                 345                 350

His Asn Ile Ala Lys Val Glu Glu His Met Val Asp Gly Arg Gln Lys
        355                 360                 365

Thr Leu Leu Val His Arg Lys Gly Ser Thr Arg Ala Phe Pro Pro His
    370                 375                 380

His Pro Leu Ile Pro Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Met Gly Ile Ala Ile Arg Val Ala Ser Pro
    450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
            500                 505

<210> SEQ ID NO 18
<211> LENGTH: 1518
<212> TYPE: DNA
<213> ORGANISM: Bos sp.

<400> SEQUENCE: 18
atgagtcgca gttataatga tgagctgcag ttcttggaaa agatcagtaa gaactgctgg      60
agaatcaaga agggcttcgt gcccaacatg caggttgaag agttttccta tgtgaatgat     120
tctctggaaa aattaatgtt tgaagaatta ggaatgcctg tcgaggtggt ggtgttggt     180 ggcttcctgc cagccatgaa acaaattggc aatgtggccg ccctgcctgg gattgttcat     240
cgatccatcg gtcttcctga tgtccattca ggttatgggt ttgctattgg aaatatggca     300
gcctttgata tgaacgaccc tgaagcagtg tatccccag gtggtgttgg gtttgacatt     360
aactgtggtc tccgcttgct gagaaccaat ttagatgaaa gtgatgttca gcctgtgaaa     420
gagcaacttg cccaagctat gtttgaccac attcctgtgg gagtggggtc aaaaggtgtc     480
```

```
atcccaatga atgccaaaga cttggaggag gccttggaga tgggtgtgga ctggtccctg      540
agagaaggct atgcctgggc agaggacaag gagcactgtg aggagtatgg aaggatgctg      600
caagctgatc ccaataaagt ctcagccagg gctaaaaaaa gaggccttcc ccagttgggg      660
actctgggag caggcaacca ctatgcagaa atccaggttg tggatgagat ttcaacgag       720 tatgctgcta agaaaatggg cattgaccat aagggacagg tgtgtgtgat gatccacagt      780
ggaagcagag gcttgggcca ccaagttgcc acagatgcac ttgtagctat ggaaaaagcc      840
atgaagagag acaagattat agtcaatgac cgtcagttgg cttgtgctcg aattgcttcc      900
ccagagggtc aggactacct gaagggaatg gcagcggctg gaactatgc ctgggtcaac       960 cgctcttcca tgaccttctt aacccgtcag gcttttgcca aggtcttcaa cacaacccct     1020
gatgacttgg acctgcatgt gatctatgat gtttctcaca atattgccaa gtagaacag      1080 catgtggtgg acgggaagga gcggactctg ttagtacaca ggaaggggtc cacccgagcc     1140
ttccctcctc accatcccct cattgcggtt gattaccaac ttaccggaca accagtgctc     1200
attggtggca ccatgggaac ctgtagctat gttcttactg gtactgagca gggcatgact     1260
gaaacctttg gaacaacttg tcatggagcg ggccgtgcac tgtcccgagc aaagtcaaga     1320
cgtaatttag atttccagga tgtcctcgac aaattggcag acatgggaat tgcaatccgt     1380
gtcgcctcac ccaagctggt aatggaagag gcccctgagt cctataagaa cgtgacggat     1440
gtggtgaaca cctgccatga tgccggaatc agcaagaagg ccattaaact gaggccaatt     1500
gctgttatca aaggatag                                                   1518

<210> SEQ ID NO 19
<211> LENGTH: 505
<212> TYPE: PRT
<213> ORGANISM: Bos sp.

<400> SEQUENCE: 19

Met Ser Arg Ser Tyr Asn Asp Glu Leu Gln Phe Leu Glu Lys Ile Ser
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ser Leu Glu Lys Leu Met Phe Glu
        35                  40                  45

Glu Leu Arg Asn Ala Cys Arg Gly Gly Val Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
```

```
            180                 185                 190
Cys Glu Glu Tyr Gly Arg Met Leu Gln Ala Asp Pro Asn Lys Val Ser
            195                 200                 205
Ala Arg Ala Lys Lys Arg Gly Leu Pro Gln Leu Gly Thr Leu Gly Ala
            210                 215                 220
Gly Asn His Tyr Ala Glu Ile Gln Val Val Asp Glu Ile Phe Asn Glu
225                 230                 235                 240
Tyr Ala Ala Lys Lys Met Gly Ile Asp His Lys Gly Gln Val Cys Val
            245                 250                 255
Met Ile His Ser Gly Ser Arg Gly Leu Gly His Gln Val Ala Thr Asp
            260                 265                 270
Ala Leu Val Ala Met Glu Lys Ala Met Lys Arg Asp Lys Ile Ile Val
            275                 280                 285
Asn Asp Arg Gln Leu Ala Cys Ala Arg Ile Ala Ser Pro Glu Gly Gln
            290                 295                 300
Asp Tyr Leu Lys Gly Met Ala Ala Gly Asn Tyr Ala Trp Val Asn
305                 310                 315                 320
Arg Ser Ser Met Thr Phe Leu Thr Arg Gln Ala Phe Ala Lys Val Phe
            325                 330                 335
Asn Thr Thr Pro Asp Asp Leu Asp Leu His Val Ile Tyr Asp Val Ser
            340                 345                 350
His Asn Ile Ala Lys Val Glu Gln His Val Val Asp Gly Lys Glu Arg
            355                 360                 365
Thr Leu Leu Val His Arg Lys Gly Ser Thr Arg Ala Phe Pro Pro His
370                 375                 380
His Pro Leu Ile Ala Val Asp Tyr Gln Leu Thr Gly Gln Pro Val Leu
385                 390                 395                 400
Ile Gly Gly Thr Met Gly Thr Cys Ser Tyr Val Leu Thr Gly Thr Glu
            405                 410                 415
Gln Gly Met Thr Glu Thr Phe Gly Thr Thr Cys His Gly Ala Gly Arg
            420                 425                 430
Ala Leu Ser Arg Ala Lys Ser Arg Arg Asn Leu Asp Phe Gln Asp Val
            435                 440                 445
Leu Asp Lys Leu Ala Asp Met Gly Ile Ala Ile Arg Val Ala Ser Pro
            450                 455                 460
Lys Leu Val Met Glu Glu Ala Pro Glu Ser Tyr Lys Asn Val Thr Asp
465                 470                 475                 480
Val Val Asn Thr Cys His Asp Ala Gly Ile Ser Lys Lys Ala Ile Lys
            485                 490                 495
Leu Arg Pro Ile Ala Val Ile Lys Gly
            500                 505

<210> SEQ ID NO 20
<211> LENGTH: 1518
<212> TYPE: DNA
<213> ORGANISM: Mus sp.

<400> SEQUENCE: 20
atgagtcgta actacaacga tgagctacag ttcttggaca agatcaataa aaactgctgg      60
aggatcaaga agggctttgt gcccaacatg caggttgaag gagtgtttta tgtgaatgat     120
gctctggaaa aactaatgtt tgaggaatta ggaacgcctg tcgaggtggt tgtgttggt     180 ggctttctgc cagccatgaa gcagattggc aatgtgcag ccctgcctgg aatagttcat     240
cggtctatcg ggcttcctga tgtccattca ggctatgggt ttgccatagg gaacatggct     300
```

```
gcctttgata tgaatgaccc tgaggccgtt gtatcccag gtggtgtcgg atttgatatt      360
aactgtggtg tccgcttgct aagaaccaat ttagatgaga gcgatgtaca gcctgtgaag      420
gaacaacttg cccaagctat gtttgaccac atccctgttg gggtgggatc aaaaggtgtc      480
attccaatga atgccaaaga cttggaggag gcattggaga tggggtgga ctggtccctg       540 agggaaggct atgcctgggc tgaagacaag gagcactgtg aggagtatgg aaggatgctg      600
caagccgacc ccaataaggt ctcacccagg caaagaaaa ggggccttcc tcagttgggg       660
accctgggag caggcaacca ttatgcagaa atccaggttg tagatgagat tttcaatgag      720
tatgccgcca gaagatggg catcgaccat aagggacagg tgtgtgtgat gatccacagt       780
ggaagcagag gcttgggcca ccaagtagct acagatgcac tggtagctat ggaaaaggcc      840
atgaagagag acaagattat agtcaatgac cggcagttgg cttgtgctcg gattgcatcc      900
ccagagggac aagactatct aaagggaatg gctgcagctg gaaactacgc ctgggttaac     960
cgctcctcta tgaccttctt aacccgtcag gcttttgcca agtcttcaa cacaacccct     1020 gatgacctgg acctgcatgt gatctatgat gtgtcgcaca atatcgccaa gtggagcag    1080 cacgtggtgg atgggaagga acggacgctg ctggtgcaca ggaagggatc cacccgtgct   1140
ttcccgcctc accacccct cattgctgtg gattatcaac tcacaggaca accagtgctt    1200
attggtggca ccatgggac ctgtagttac gttctgactg gcactgaaca aggcatgact    1260
gagacctttg aacaacctg tcatggagcg ggccgtgctt tgtccagagc aaaatcacgt    1320
cgtaacttag atttccaaga tgtcttagac aaactggcag acatgggaat tgcaatccgg    1380
gttgcttccc ccaagctggt tatggaagag gcaccagagt cctataagaa tgtgacagac    1440
gtcgtgaaca cctgccatga tgctgggatc agcaagaagg ccattaaact gagaccaatt    1500
gctgttatta aagggtag                                                   1518
```

<210> SEQ ID NO 21
<211> LENGTH: 505
<212> TYPE: PRT
<213> ORGANISM: Mus sp.

<400> SEQUENCE: 21

```
Met Ser Arg Asn Tyr Asn Asp Glu Leu Gln Phe Leu Asp Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
```

```
                145                 150                 155                 160
        Ile Pro Met Asn Ala Lys Asp Leu Glu Glu Ala Leu Glu Met Gly Val
                        165                 170                 175
        Asp Trp Ser Leu Arg Glu Gly Tyr Ala Trp Ala Glu Asp Lys Glu His
                        180                 185                 190
        Cys Glu Glu Tyr Gly Arg Met Leu Gln Ala Asp Pro Asn Lys Val Ser
                        195                 200                 205
        Pro Arg Ala Lys Lys Arg Gly Leu Pro Gln Leu Gly Thr Leu Gly Ala
        210                 215                 220
        Gly Asn His Tyr Ala Glu Ile Gln Val Val Asp Glu Ile Phe Asn Glu
        225                 230                 235                 240
        Tyr Ala Ala Lys Lys Met Gly Ile Asp His Lys Gly Gln Val Cys Val
                        245                 250                 255
        Met Ile His Ser Gly Ser Arg Gly Leu Gly His Gln Val Ala Thr Asp
                        260                 265                 270
        Ala Leu Val Ala Met Glu Lys Ala Met Lys Arg Asp Lys Ile Ile Val
                        275                 280                 285
        Asn Asp Arg Gln Leu Ala Cys Ala Arg Ile Ala Ser Pro Glu Gly Gln
        290                 295                 300
        Asp Tyr Leu Lys Gly Met Ala Ala Ala Gly Asn Tyr Ala Trp Val Asn
        305                 310                 315                 320
        Arg Ser Ser Met Thr Phe Leu Thr Arg Gln Ala Phe Ala Lys Val Phe
                        325                 330                 335
        Asn Thr Thr Pro Asp Asp Leu Asp Leu His Val Ile Tyr Asp Val Ser
                        340                 345                 350
        His Asn Ile Ala Lys Val Glu Gln His Val Val Asp Gly Lys Glu Arg
                        355                 360                 365
        Thr Leu Leu Val His Arg Lys Gly Ser Thr Arg Ala Phe Pro Pro His
                        370                 375                 380
        His Pro Leu Ile Ala Val Asp Tyr Gln Leu Thr Gly Gln Pro Val Leu
        385                 390                 395                 400
        Ile Gly Gly Thr Met Gly Thr Cys Ser Tyr Val Leu Thr Gly Thr Glu
                        405                 410                 415
        Gln Gly Met Thr Glu Thr Phe Gly Thr Thr Cys His Gly Ala Gly Arg
                        420                 425                 430
        Ala Leu Ser Arg Ala Lys Ser Arg Arg Asn Leu Asp Phe Gln Asp Val
                        435                 440                 445
        Leu Asp Lys Leu Ala Asp Met Gly Ile Ala Ile Arg Val Ala Ser Pro
        450                 455                 460
        Lys Leu Val Met Glu Glu Ala Pro Glu Ser Tyr Lys Asn Val Thr Asp
        465                 470                 475                 480
        Val Val Asn Thr Cys His Asp Ala Gly Ile Ser Lys Lys Ala Ile Lys
                        485                 490                 495
        Leu Arg Pro Ile Ala Val Ile Lys Gly
                        500                 505

<210> SEQ ID NO 22
<211> LENGTH: 1518
<212> TYPE: DNA
<213> ORGANISM: Rattus sp.

<400> SEQUENCE: 22
atgagtcgta actacaacga tgagctacag ttcttggaca agatcaataa gaactgctgg      60
aggatcaaga agggctttgt gcccaacatg caggttgaag gggtgtttta tgtgaatgac     120
```

-continued

```
gctctggaaa agctcatgtt tgaggagtta cggaatgcct gtcgaggtgg tggtgttggt      180
ggcttcctgc cagccatgaa gcagattggc aatgtggcag ccctgcctgg aatagttcat      240
cggtctattg ggcttcctga tgtccactca ggctacgggt ttgccatagg aacatggct       300
gcctttgata tgaatgaccc tgaggcagtt gtatccccag gtggtgtcgg atttgatatt      360
aactgtggtg tccgcttgct aaggaccaat ttagatgaga gcgatgtaca gcctgtgaag      420
gaacaacttg cccaagctat gtttgaccac atccctgtcg gggtgggatc gaaaggtgtc      480
attccaatga atgccaaaga cttggaggag cattggaga tgggtgtgga ctggtcccta      540
agagaaggct atgcctgggc tgaggacaag gagcactgtg aggagtatgg aaggatgctc      600
caagccgacc ccaataaggt ctcacccaga gcaagaaaaa ggggccttcc tcagttgggg      660
accctgggag caggcaacca ttatgcagag atccaggttg tagatgagat ttcaacgag       720
tatgctgcca agaagatggg catcgaccat aagggacagg tgtgcgtgat gatccacagc      780
gggagcagag gcttgggcca tcaagtagct acagacgcac tggtagctat ggagaaagcc      840
atgaagagag acaagattat agtcaatgac cggcagctgg cgtgtgctcg gattgcatcc      900
ccagagggac aagactatct aaagggaatg gctgccgctg gaaactgtgc ctgggttaac      960
cgctcgtcta tgaccttctt aacccgtcag gcttttgcca aagtcttcaa cacaaccct      1020
gacgacctgg acctgcatgt gatttatgat gtttctcaca acatcgccaa agtggagcag     1080
cacgtggtag acggaaagga gcggacgctg ttggtgcaca ggaaagggtc cacccgcgct     1140
ttccctcctc accatcccct cattgctgtt gattaccagc tcactggaca accagtgctt     1200
atcggtggca ccatggggac ctgtagttat gttctgactg gcactgaaca aggcatgact     1260
gagacctttg gaacaacctg tcatggagcg ggccgtgctt tgtccagagc aaaatcacgt     1320
cgtaatttag atttccaaga tgtcttagac aagctggcag acatgggaat cgccatccgg     1380
gttgcgtccc ccaagctggt tatggaagag gctccagaat catataagaa tgtgacagac     1440
gtcgtgaaca cttgccatga tgctgggatc agcaagaagg ccattaaact gagaccaatt     1500
gctgttatta aaggatag                                                   1518
```

<210> SEQ ID NO 23
<211> LENGTH: 505
<212> TYPE: PRT
<213> ORGANISM: Rattus sp.

<400> SEQUENCE: 23

```
Met Ser Arg Asn Tyr Asn Asp Glu Leu Gln Phe Leu Asp Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
```

```
                  115                 120                 125
Thr Asn Leu Asp Glu Ser Asp Val Gln Pro Val Lys Glu Gln Leu Ala
    130                 135                 140
Gln Ala Met Phe Asp His Ile Pro Val Gly Val Gly Ser Lys Gly Val
145                 150                 155                 160
Ile Pro Met Asn Ala Lys Asp Leu Glu Glu Ala Leu Glu Met Gly Val
                165                 170                 175
Asp Trp Ser Leu Arg Glu Gly Tyr Ala Trp Ala Glu Asp Lys Glu His
                180                 185                 190
Cys Glu Glu Tyr Gly Arg Met Leu Gln Ala Asp Pro Asn Lys Val Ser
            195                 200                 205
Pro Arg Ala Lys Lys Arg Gly Leu Pro Gln Leu Gly Thr Leu Gly Ala
    210                 215                 220
Gly Asn His Tyr Ala Glu Ile Gln Val Val Asp Glu Ile Phe Asn Glu
225                 230                 235                 240
Tyr Ala Ala Lys Lys Met Gly Ile Asp His Lys Gly Gln Val Cys Val
                245                 250                 255
Met Ile His Ser Gly Ser Arg Gly Leu Gly His Gln Val Ala Thr Asp
            260                 265                 270
Ala Leu Val Ala Met Glu Lys Ala Met Lys Arg Asp Lys Ile Ile Val
    275                 280                 285
Asn Asp Arg Gln Leu Ala Cys Ala Arg Ile Ala Ser Pro Glu Gly Gln
290                 295                 300
Asp Tyr Leu Lys Gly Met Ala Ala Gly Asn Cys Ala Trp Val Asn
305                 310                 315                 320
Arg Ser Ser Met Thr Phe Leu Thr Arg Gln Ala Phe Ala Lys Val Phe
                325                 330                 335
Asn Thr Thr Pro Asp Asp Leu Asp Leu His Val Ile Tyr Asp Val Ser
            340                 345                 350
His Asn Ile Ala Lys Val Glu Gln His Val Val Asp Gly Lys Glu Arg
    355                 360                 365
Thr Leu Leu Val His Arg Lys Gly Ser Thr Arg Ala Phe Pro Pro His
370                 375                 380
His Pro Leu Ile Ala Val Asp Tyr Gln Leu Thr Gly Gln Pro Val Leu
385                 390                 395                 400
Ile Gly Gly Thr Met Gly Thr Cys Ser Tyr Val Leu Thr Gly Thr Glu
                405                 410                 415
Gln Gly Met Thr Glu Thr Phe Gly Thr Thr Cys His Gly Ala Gly Arg
            420                 425                 430
Ala Leu Ser Arg Ala Lys Ser Arg Arg Asn Leu Asp Phe Gln Asp Val
    435                 440                 445
Leu Asp Lys Leu Ala Asp Met Gly Ile Ala Ile Arg Val Ala Ser Pro
450                 455                 460
Lys Leu Val Met Glu Glu Ala Pro Glu Ser Tyr Lys Asn Val Thr Asp
465                 470                 475                 480
Val Val Asn Thr Cys His Asp Ala Gly Ile Ser Lys Lys Ala Ile Lys
                485                 490                 495
Leu Arg Pro Ile Ala Val Ile Lys Gly
            500                 505

<210> SEQ ID NO 24
<211> LENGTH: 181
<212> TYPE: PRT
<213> ORGANISM: Encephalitozoon cuniculi
```

<400> SEQUENCE: 24

Met Met Tyr Ile Ser Val Gln Arg His Cys Ser Ser Leu Asp Pro His
1               5                   10                  15

Phe Phe Ser Thr Phe Arg Val Gly His Thr Asp Pro Gln Tyr Gln Met
            20                  25                  30

Gln Gly Thr Ser His Thr Ala Met Arg Ala Thr Ala Gly Lys Ser Leu
        35                  40                  45

Glu Ser Ile Glu Phe Leu Asp His Pro Ala Asp Ile Gln Met His Cys
    50                  55                  60

Thr Ala Ser Ser Leu Pro Glu Leu Tyr Glu Val Ala Ile Lys Gly Met
65                  70                  75                  80

Met Ser Cys Ser Val Arg Ile Ser Ala Thr Asp Arg Arg Leu Gly Arg
                85                  90                  95

Val Glu Leu Ser Glu Thr Ser Asp Glu Met Asn Met Val Gly Leu Leu
            100                 105                 110

Thr His Phe Met Asp Leu Met Tyr Gly Glu Gly Leu Val Val Thr Glu
        115                 120                 125

Ala Ala Val Leu Leu Arg Asn Gly Leu Leu Val Cys Asp Tyr Ala Val
    130                 135                 140

Thr Ser Gly Ser Arg Cys Gln Ser Leu Cys Glu Ile Lys Ala Val Thr
145                 150                 155                 160

Leu Cys Gly Leu Arg Val Phe Glu Glu Asp Gly Ile Phe His Leu Tyr
                165                 170                 175

Cys Ile Phe Asp Val
            180

<210> SEQ ID NO 25
<211> LENGTH: 205
<212> TYPE: PRT
<213> ORGANISM: Plasmodium berghei

<400> SEQUENCE: 25

Met Arg Asp Phe Pro Asn Ser Lys Ile Ile Ser Leu Pro Gln Arg Asn
1               5                   10                  15

Arg Arg Arg Ile Asn Arg Ser Tyr Val His Glu Asn Glu Ser Glu
            20                  25                  30

Tyr Thr Asn Glu Ile Glu Glu Asn Glu Ala Thr Asn Asp Glu Ile Ile
        35                  40                  45

Asp Gln Asn Ile Met Asn Asp Ile Glu Ile Cys Asn Ile Asn Leu Asn
    50                  55                  60

Lys Asn Tyr Lys Tyr Glu Tyr Leu Asp His Thr Ala Asp Ile Ile Leu
65                  70                  75                  80

His Ser Tyr Gly Asn Asn Leu Lys Glu Ala Phe Glu Ala Val Cys Ile
                85                  90                  95

Ser Leu Phe Asn Tyr Met Cys Asp Leu Lys Asn Val Glu Leu Lys Met
            100                 105                 110

Lys Arg Lys Val Ser Ile Lys Gly Asp Asp Leu Asp Asp Leu Leu Phe
        115                 120                 125

Lys Phe Leu Val Glu Phe His Phe Leu Tyr Gly Asn Glu Tyr Phe Ile
    130                 135                 140

Cys Lys Thr Ile Asp Ile Ile Val Phe Asp Ile Glu Gln Phe Tyr Ile
145                 150                 155                 160

Glu Ala Tyr Gly Tyr Gly Glu Leu Phe Ser Thr Asp Lys His Glu Cys
                165                 170                 175

```
Gly Thr Glu Ile Lys Ala Ile Thr Lys His Glu Leu Lys Ile Val Ser
            180                 185                 190

Asn Asn Asp Ser Cys Asp Val Phe Val Leu Val Asp Ile
        195                 200                 205
```

<210> SEQ ID NO 26
<211> LENGTH: 112
<212> TYPE: PRT
<213> ORGANISM: Trichoplax adhaerens

<400> SEQUENCE: 26

```
Ala Leu Gly Met Leu Ala Tyr Ile Thr Asp Leu Arg Cys Val Glu Pro
1               5                   10                  15

Ile Lys Thr Gln Gln Ile Glu Ala Glu Gly His Asp Leu Glu Ser Leu
            20                  25                  30

Leu Tyr His Phe Leu Asp Glu Phe Leu Phe Leu Ser Ala Glu Pro
        35                  40                  45

Phe Phe Ile Ala Lys Asn Val Lys Ile Leu Lys Phe Asp Lys Glu Asn
50                  55                  60

Phe Arg Ile Thr Ala Glu Gly Val Gly Glu Ile Phe Asp Leu Ser Arg
65                  70                  75                  80

His Pro Gln Gly Thr Glu Val Lys Ala Ile Thr Tyr Ser Asn Met Gln
                85                  90                  95

Ile Phe Asp Ser Ile Asn Lys His Glu Cys Tyr Val Ile Val Asp Ile
            100                 105                 110
```

<210> SEQ ID NO 27
<211> LENGTH: 148
<212> TYPE: PRT
<213> ORGANISM: Hydra magnipapillata

<400> SEQUENCE: 27

```
Met Glu Ser Asp Ser Ser Asp Asn Tyr Gly Tyr Glu Tyr Leu Asp His
1               5                   10                  15

Pro Ala Asp Ile Gln Ile His Ser Trp Gly Leu Thr Leu Lys Gln Ala
            20                  25                  30

Phe Glu Gln Gln Ala Ile Gly Met Phe Gly Ile Met Thr Asp Leu Asn
        35                  40                  45

Thr Ile Glu Asn Leu Gln Glu Glu Val Ile Glu Ala Glu Gly His Asp
    50                  55                  60

Leu Val Ser Leu Leu Tyr Lys Phe Leu Asp Glu Cys Leu Phe Ala Phe
65                  70                  75                  80

Ser Val Glu Pro Phe Leu Cys Ala Phe Asp Val Asn Ile Thr Glu Phe
                85                  90                  95

Asp Glu Glu Asn Phe Val Ile Lys Ala Val Leu Lys Gly Glu Thr Phe
            100                 105                 110

Asp Leu Ser Lys His Pro Gln Gly Thr Glu Val Lys Ala Ile Thr Phe
        115                 120                 125

Ser Asn Met Gln Ile Asn Lys Glu Ser Ala His Trp Glu Cys Tyr Val
    130                 135                 140

Ile Phe Asp Ile
145
```

<210> SEQ ID NO 28
<211> LENGTH: 167
<212> TYPE: PRT
<213> ORGANISM: Homo sapiens

<400> SEQUENCE: 28

Met Ala Gln Glu Glu Asp Val Arg Asp Tyr Asn Leu Thr Glu Glu
1               5                   10                  15

Gln Lys Ala Ile Lys Ala Lys Tyr Pro Pro Val Asn Arg Lys Tyr Glu
                20                  25                  30

Tyr Leu Asp His Thr Ala Asp Val Gln Leu His Ala Trp Gly Asp Thr
            35                  40                  45

Leu Glu Glu Ala Phe Glu Gln Cys Ala Met Ala Phe Gly Tyr Met
    50                  55                  60

Thr Asp Thr Gly Thr Val Glu Pro Leu Gln Thr Val Glu Val Glu Thr
65                  70                  75                  80

Gln Gly Asp Asp Leu Gln Ser Leu Leu Phe His Phe Leu Asp Glu Trp
                85                  90                  95

Leu Tyr Lys Phe Ser Ala Asp Glu Phe Phe Ile Pro Arg Glu Val Lys
                100                 105                 110

Val Leu Ser Ile Asp Gln Arg Asn Phe Lys Leu Arg Ser Ile Gly Trp
            115                 120                 125

Gly Glu Glu Phe Ser Leu Ser Lys His Pro Gln Gly Thr Glu Val Lys
130                 135                 140

Ala Ile Thr Tyr Ser Ala Met Gln Val Tyr Asn Glu Glu Asn Pro Glu
145                 150                 155                 160

Val Phe Val Ile Ile Asp Ile
                165

<210> SEQ ID NO 29
<211> LENGTH: 156
<212> TYPE: PRT
<213> ORGANISM: Drosophila melanogaster

<400> SEQUENCE: 29

Met Glu Val Glu Phe Ser Arg Glu Asn Phe Leu Leu Pro Glu Met Lys
1               5                   10                  15

Tyr Glu Tyr Leu Asp His Thr Ala Asp Val Gln Ile His Gly Trp Gly
                20                  25                  30

Ser Ser Leu Lys Glu Ala Phe Glu Gln Cys Gly Val Ala Met Phe Gly
            35                  40                  45

Tyr Met Thr Glu Leu Asp Tyr Val Ser Val Glu Gln Cys Phe Glu Ile
    50                  55                  60

Glu Ala His Gly Asp Asp Leu Glu Ser Leu Leu Phe His Phe Leu Asp
65                  70                  75                  80

Glu Leu Leu Phe Leu Phe Ser Ala Glu Pro Tyr Leu Val Cys Lys Lys
                85                  90                  95

Leu Glu Ile Thr Lys Phe Asp Val Glu Asn Phe Glu Ile Ser Cys His
            100                 105                 110

Cys Tyr Gly Glu Pro Phe Glu Leu Gly Lys His Pro Gln Gly Thr Glu
        115                 120                 125

Val Lys Ala Ile Thr Tyr Ser Ala Met Gln Ile Ile Gln Asp Val Glu
130                 135                 140

Ala Ser Asn Tyr Glu Val Phe Val Ile Ile Asp Ile
145                 150                 155

<210> SEQ ID NO 30
<211> LENGTH: 151
<212> TYPE: PRT
<213> ORGANISM: Dictyostelium discoideum

<400> SEQUENCE: 30

```
Met Glu Ser Tyr Gly Leu Gly Gln Leu Lys Asn Phe Glu Tyr Leu Asp
1               5                   10                  15

His Thr Ala Asp Ile Met Phe His Thr Trp Gly Lys Asp Leu Lys Glu
            20                  25                  30

Ala Leu Glu Gln Met Val Leu Ile Met Asn Asn Tyr Met Val Glu Leu
        35                  40                  45

Asp Ser Val Glu Leu Asp Asp Ser Ala Thr Glu Gln Thr Ile Ser Val
    50                  55                  60

Asn Gly His Asp Met Asp Ser Leu Leu Phe Ala Leu Leu Asp Glu Phe
65                  70                  75                  80

Leu Phe Val Phe Ser Thr Glu Phe Ile Ile Phe Lys Gln Val Gln Ile
                85                  90                  95

Ile Ser Phe Asp Arg Glu Asn Phe Ser Ile Lys Ala Ile Gly Lys Gly
            100                 105                 110

Val Glu Leu Asp Lys Ser Lys His Thr Thr Gly Thr Glu Ile Lys Ala
        115                 120                 125

Ile Thr Tyr Ser Cys Met Lys Ile Glu Glu Asn Pro Asp Lys Ser Asp
    130                 135                 140

Ile His Val Ile Val Asp Ile
145                 150
```

<210> SEQ ID NO 31
<211> LENGTH: 260
<212> TYPE: PRT
<213> ORGANISM: Chlamydomonas reinhardtii

<400> SEQUENCE: 31

```
Met Gly Gly Glu Glu Asp Ala Leu Pro Gln Arg Leu Asn Ser Arg Gln
1               5                   10                  15

Arg Arg Arg Glu Gln Gln His Gln Val Gln Gln Gly Thr Glu Ala Ala
            20                  25                  30

Ser Gly Ile Glu Asp Gly Ala Ala Gln Ala Pro Ser Ala Ser Gly Arg
        35                  40                  45

Gln Gly Arg Glu Glu His Gly Ala Gly Leu Gly Glu Gly Arg Ser Lys
    50                  55                  60

Ala Ala Pro Ala Gly Thr Pro Arg Arg Pro Glu Ser Arg Ser Ala Ser
65                  70                  75                  80

Arg Asp Thr Lys Ser Asp Pro Gly Leu Gly Lys Asp Ser Gly Val Ser
                85                  90                  95

Gly Val Cys Val Glu Val Gly Ala Val Thr Thr Leu Glu Pro Leu Pro
            100                 105                 110

Glu Tyr Arg Ser Ala Ala Val Gly Asp Tyr Lys Phe Glu Tyr Leu Asp
        115                 120                 125

His Thr Ala Asp Val Gln Leu His Ala Trp Gly Ser Asp Leu Gly Glu
    130                 135                 140

Ala Phe Glu Gln Cys Gly Leu Ala Met Phe Asn Tyr Met Ser Pro Leu
145                 150                 155                 160

Glu His Val Arg Leu Arg Glu Thr Arg Ala Tyr Arg Ala Glu Gly His
                165                 170                 175

Asp Leu Pro Ser Leu Leu Phe Ala Phe Leu Asp Glu Leu Leu Phe Glu
            180                 185                 190

Phe Asn Thr Glu Leu Phe Leu Ala Gly Arg Val Arg Ile Thr Lys Phe
        195                 200                 205
```

```
Asp Arg Glu Ala Phe Val Ile Glu Ala Glu Gly His Gly Glu Arg Phe
    210                 215                 220

Asp Arg Ser Leu His Glu Val Gly Thr Glu Ile Lys Ala Ile Thr Tyr
225                 230                 235                 240

Ser Ala Met Ser Ile Ser Glu Gln Glu Gly Asp Ala Gly Val Phe Val
                245                 250                 255

Ile Val Asp Ile
            260

<210> SEQ ID NO 32
<211> LENGTH: 167
<212> TYPE: PRT
<213> ORGANISM: Caligus rogercresseyi

<400> SEQUENCE: 32

Met Glu Arg Glu Asp Pro Thr Gln Glu Ser Asp Gln Asp Arg Pro Thr
1               5                   10                  15

Ser Gly Tyr Glu Tyr Leu Asp His Thr Ala Asp Val Gln Ile His Ala
            20                  25                  30

Trp Ser Ser Thr Leu Arg Glu Ala Ile Cys Glu Ala Ala Leu Gly Val
        35                  40                  45

Tyr Asn Tyr Met Thr Asp Leu Ser Ala Val Thr Ala Ser Glu Asp Leu
50                  55                  60

Ile Leu Lys Ala Gln Gly His Asp Leu Glu Ser Leu Leu Tyr Asn Phe
65                  70                  75                  80

Leu Asp Glu Cys Leu Tyr His Phe His Ala Glu Glu Tyr Phe Val Ala
                85                  90                  95

Cys Glu Val Glu Leu Ile Asp Phe Asp Arg Val Arg Ser Gln Gly Glu
            100                 105                 110

Glu Gly Lys Glu Glu Lys Glu Leu Ser Ile Thr Ala Arg Leu Arg Gly
        115                 120                 125

Glu Lys Phe Asp Leu Asn Lys His Ser Pro Gly Thr Glu Ile Lys Ala
    130                 135                 140

Ile Thr Tyr Ser Ala Met Gln Val Leu Glu Lys Asp Cys Phe Ala Gln
145                 150                 155                 160

Met Phe Val Ile Val Asp Ile
                165

<210> SEQ ID NO 33
<211> LENGTH: 155
<212> TYPE: PRT
<213> ORGANISM: Caenorhabditis elegans

<400> SEQUENCE: 33

Met Pro Ser Thr Ser Met Ile Glu Asp Arg Ser Glu Ile Glu Arg Arg
1               5                   10                  15

Arg Phe Glu Tyr Leu Asp His Pro Ala Asp Ile Gln Leu His Ser Trp
            20                  25                  30

Gly Ser Thr Met Glu Glu Ala Phe Glu Ala Cys Leu Val Ser Met Phe
        35                  40                  45

Gly Tyr Met Thr Asp Leu Ala Lys Val Asp Glu Met Tyr Glu Phe Tyr
50                  55                  60

Trp Lys Ala Ser Gly Asp Ser Leu Asp Gly Leu Leu Phe Gln Phe Leu
65                  70                  75                  80

Asp Glu Ala Leu Asn Ser Phe His Ala Glu Pro Cys Phe Val Ala Lys
                85                  90                  95
```

Arg Val Glu Ile Leu Arg Phe Asp Lys Lys Phe Glu Ile Glu Phe
            100                 105                 110

Arg Gly Trp Gly Glu Ser Phe Asp Thr Ser Lys His Glu Thr Glu Ala
        115                 120                 125

Asp Ile Lys Ser Pro Thr Tyr Ser Asn Met Gln Ile Asn Glu Lys Pro
        130                 135                 140

Glu Arg Cys Asp Ile Tyr Val Ile Val Asp Ile
145                 150                 155

<210> SEQ ID NO 34
<211> LENGTH: 143
<212> TYPE: PRT
<213> ORGANISM: Entamoeba histolytica

<400> SEQUENCE: 34

Met Ser Phe Glu Tyr Leu Asp His Pro Ala Asp Val Ile Leu His Ser
1               5                   10                  15

Trp Gly Gln Asn Ile Ile Glu Ala Phe Glu Asn Ala Ala Ala Gly Met
            20                  25                  30

Phe Asn Phe Met Ser Asp Leu Thr Lys Val Glu Glu Lys Glu Ile Lys
        35                  40                  45

Lys Ile Ser Ile Asp Ala Thr Ser Tyr Glu Glu Ala Leu Val Lys Phe
50                  55                  60

Leu Asp Ser Trp Leu Cys Ile Phe Ser Ser Glu Leu Phe Ile Gly Lys
65                  70                  75                  80

Ser Phe Lys Cys Glu Val Phe Asp Asp Asn Asp Glu Glu Asn Ile His
                85                  90                  95

Ile Glu Cys Lys Gly Ile Gly Glu Tyr Phe Val Ile Gly Lys His Gln
            100                 105                 110

Gln Gly Thr Glu Ile Lys Ala Ile Thr Trp His Asn Leu Glu Ile Tyr
        115                 120                 125

Asp Asp Glu Lys Asp Gln Thr His Ile His Ile Leu Leu Asp Ile
        130                 135                 140

<210> SEQ ID NO 35
<211> LENGTH: 139
<212> TYPE: PRT
<213> ORGANISM: Sulfolobus islandicus

<400> SEQUENCE: 35

Met Arg Ser Phe Glu Phe Phe Glu His Thr Ala Asp Val Gly Ile Arg
1               5                   10                  15

Ala Tyr Gly Lys Ser Leu Glu Glu Ala Phe Ser Asn Ala Ala Leu Gly
            20                  25                  30

Val Phe Glu Val Ile Thr Asp Thr Ser Lys Val Lys Pro Ile Glu Tyr
        35                  40                  45

Arg Glu Ile Tyr Leu Asn Gly Tyr Asp Leu Glu Asn Leu Leu Tyr Lys
50                  55                  60

Trp Ile Glu Glu Leu Leu Tyr Tyr Tyr Asp Ser Glu Leu Met Val Phe
65                  70                  75                  80

Ser Lys Phe Asp Leu Met Ile Asp Gln Asp Ser Met Thr Leu Glu Gly
                85                  90                  95

Lys Ala Trp Gly Glu Lys Phe Asn Gly Lys Ile His Glu Arg Arg Thr
            100                 105                 110

Val Val Lys Ala Met Thr Tyr His Gln Leu Ser Ile Glu Lys Thr Glu
        115                 120                 125

```
Asn Cys Tyr Val Ile Thr Phe Val Val Asp Ile
    130                 135

<210> SEQ ID NO 36
<211> LENGTH: 138
<212> TYPE: PRT
<213> ORGANISM: Methanococcus maripaludis

<400> SEQUENCE: 36

Met Tyr Asn Tyr Phe Glu Thr Thr Ala Asp Ile Gly Ile Ile Ala Phe
1               5                   10                  15

Gly Lys Thr Leu Glu Glu Ser Phe Glu Asn Ser Ala Arg Gly Leu Ser
            20                  25                  30

Asn Ile Met Val Asp Ile Lys Ser Ile Glu Lys Ile Glu Lys His Ser
        35                  40                  45

Phe Lys Val Ile Ser Glu Asp Leu Phe Gly Leu Leu Tyr Asp Phe Leu
    50                  55                  60

Thr Glu Leu Leu Ile Leu Gln Asp Ser Glu Leu Leu Ile Phe Ser Glu
65                  70                  75                  80

Phe Asn Val Lys Ile Glu Arg Asn Glu Cys Tyr Glu Leu Ser Cys Val
                85                  90                  95

Ala Phe Gly Asp Arg Tyr Ser Lys Asp Lys Tyr Glu Pro Lys Glu Glu
            100                 105                 110

Val Lys Ala Ile Thr Tyr His Arg Met Glu Ile Ser Lys Ser Glu Asn
        115                 120                 125

Cys Trp Lys Thr Gln Phe Ile Val Asp Leu
    130                 135

<210> SEQ ID NO 37
<211> LENGTH: 137
<212> TYPE: PRT
<213> ORGANISM: Archaeoglobus fulgidus

<400> SEQUENCE: 37

Met Lys Tyr Arg Phe Ile Asp His Thr Ala Asp Ile Ala Phe Glu Val
1               5                   10                  15

Tyr Gly Ser Asn Leu Arg Glu Leu Phe Glu Asn Ala Ala Leu Ala Phe
            20                  25                  30

Tyr Asp Ala Phe Val Asp Thr Ser Gly Ile Gly Ile Glu Arg Glu Val
        35                  40                  45

Gly Val Glu Cys Glu Gly Glu Asp Val Glu Ile Thr Leu Tyr Arg Trp
    50                  55                  60

Leu Asn Glu Leu Leu Tyr Leu Phe Asp Thr Glu Phe Phe Ala Ala Lys
65                  70                  75                  80

Asp Val Glu Val Glu Val Glu Glu Gly Asp Gly Val Lys Ala Ser Gly
                85                  90                  95

Lys Leu Arg Gly Gly Arg Phe Ser Ala Glu Met Val Leu Val Glu Pro
            100                 105                 110

Lys Ala Ile Thr Leu His Lys Phe Arg Val Glu Lys Thr Asp Lys Gly
        115                 120                 125

Tyr Val Ala Phe Val Val Val Asp Ile
    130                 135

<210> SEQ ID NO 38
<211> LENGTH: 140
<212> TYPE: PRT
<213> ORGANISM: Synechococcus sp.
```

<400> SEQUENCE: 38

Met Ala Arg Ala Arg Trp Asp His Phe Glu His Met Ala Asp Val Gly
1               5                   10                  15

Val Arg Gly Tyr Gly Ala Thr Pro Glu Glu Ala Phe Ala Gln Ala Ala
            20                  25                  30

Leu Ala Leu Thr Ala Val Ile Thr Ser Val Asp Glu Val Ala Pro Arg
        35                  40                  45

Glu Arg Leu Glu Ile Glu Leu Glu Asn Ser Gly Asp Leu Glu Leu Leu
    50                  55                  60

Leu Val Asp Phe Leu Asn Ala Val Ile Tyr Glu Met Ala Val Arg Gly
65                  70                  75                  80

Met Leu Phe Gly Lys Val Glu Val His Leu Ala Lys Asp His Leu Lys
                85                  90                  95

Ala Ser Leu Trp Gly Glu Arg Val Asp Arg Ala Lys His Arg Pro Ala
            100                 105                 110

Val Glu Val Lys Gly Ala Thr Tyr Thr Gln Leu Lys Val Ala Gln Glu
        115                 120                 125

Ser Glu Leu Trp Val Ala Gln Cys Val Val Asp Val
    130                 135                 140

<210> SEQ ID NO 39
<211> LENGTH: 140
<212> TYPE: PRT
<213> ORGANISM: Aquifex aeolicus

<400> SEQUENCE: 39

Met Val Lys Leu Asp Tyr Glu Pro Val Tyr Asp Ile Thr Ala Asp Ala
1               5                   10                  15

Gly Ile Arg Val Arg Ala Lys Thr Leu Glu Glu Leu Phe Cys His Ala
            20                  25                  30

Ile Leu Ala Thr Phe Asn Glu Ile Thr Asp Ile Asp Lys Val Glu Pro
        35                  40                  45

Lys Glu Glu Tyr Glu Ile Gln Ala Gln Asn Asp Met Pro Phe Leu Leu
    50                  55                  60

Ala Asp Ile Ile Asn Glu Ala Leu Val Leu His Glu Ser Lys His Phe
65                  70                  75                  80

Val Ala Ser Glu Cys Glu Val Leu Glu Leu Lys Glu Asp Phe Val Lys
                85                  90                  95

Val Lys Leu Lys Gly Glu Lys Phe Asp Pro Lys Arg His Pro Ser Lys
            100                 105                 110

Leu Val Ile Lys Ala Ala Thr Tyr His Arg Leu Arg Val Glu Lys Lys
        115                 120                 125

Asn Glu His Trp Glu Ala Glu Val Ile Phe Asp Ile
    130                 135                 140

<210> SEQ ID NO 40
<211> LENGTH: 139
<212> TYPE: PRT
<213> ORGANISM: Thermus thermophilus

<400> SEQUENCE: 40

Met Val Val Arg Pro Leu Asp His Thr Ala Asp Val Gly Phe Ala Leu
1               5                   10                  15

Glu Ala Gln Asn Leu Glu Glu Leu Phe Gln Ala Ala Leu Lys Gly Leu
            20                  25                  30

Leu Asp Val Met Phe Thr Ala Pro Pro Gln Gly Gly Arg Lys Arg Arg
            35                  40                  45

Arg Leu Arg Leu Phe Ala Glu Asp Leu Glu Thr Leu Leu Val Arg Phe
 50                  55                  60

Leu Asn Glu Leu Ile Tyr Leu Ile Gln Thr Lys Gly Phe Val Pro Gly
 65                  70                  75                  80

Arg Ala Arg Ile Arg Val Glu Glu Glu Gly Gly Tyr Arg Leu Ile
                 85                  90                  95

Ala Thr Leu Phe Gly Glu Pro Phe Gln Glu Gly Leu Gly Phe Gln Gly
                100                 105                 110

Glu Val Lys Ser Ala Thr Phe His Gly Leu Ser Val Arg Lys Glu Asp
            115                 120                 125

Asp Arg Trp Lys Ala Gln Val Ile Leu Asp Val
            130                 135

<210> SEQ ID NO 41
<211> LENGTH: 143
<212> TYPE: PRT
<213> ORGANISM: Archaeal BJ1

<400> SEQUENCE: 41

Met Ser Tyr Ala Leu Arg Asp His Thr Ala Asp Val Ala Val Glu Ala
 1               5                  10                  15

Thr Ala Pro Thr Leu Ala Ala Leu Phe Glu Ala Val Ala Asp Gly Leu
                20                  25                  30

Thr Ala Ala Ser Cys Glu Ala Val Pro Glu Gly Gly Asp Arg Phe Glu
            35                  40                  45

Leu Ser Val Thr Ala Glu Ser Arg Glu Ala Leu Leu Phe Asp Tyr Leu
 50                  55                  60

Asp Gln Leu Ile Tyr Glu Arg Asp Val Arg Leu Val Leu Pro Ala Asp
 65                  70                  75                  80

His Arg Cys Thr Val Ser Gly Pro Asp Asp Thr Glu Ser Gly Asp Asp
                 85                  90                  95

Ala Ala Trp Thr Val Glu Ala Thr Ala Arg Gly Val Pro Leu Gly Asp
                100                 105                 110

Val Ala Ala Arg Glu Ile Lys Ala Val Thr Tyr Ser Glu Met Thr Leu
            115                 120                 125

Asp Arg Arg Asp Asp Gly Trp Tyr Ala Tyr Val Val Phe Asp Val
            130                 135                 140

<210> SEQ ID NO 42
<211> LENGTH: 179
<212> TYPE: PRT
<213> ORGANISM: Mycobacterium tuberculosis

<400> SEQUENCE: 42

Met Leu His Arg Asp Asp His Ile Asn Pro Pro Arg Pro Arg Gly Leu
 1               5                  10                  15

Asp Val Pro Cys Ala Arg Leu Arg Ala Thr Asn Pro Leu Arg Ala Leu
                20                  25                  30

Ala Arg Cys Val Gln Ala Gly Lys Pro Gly Thr Ser Ser Gly His Arg
            35                  40                  45

Ser Val Pro His Thr Ala Asp Leu Arg Ile Glu Ala Trp Ala Pro Thr
 50                  55                  60

Arg Asp Gly Cys Ile Arg Gln Ala Val Leu Gly Thr Val Glu Ser Phe
 65                  70                  75                  80

```
Leu Asp Leu Glu Ser Ala His Ala Val His Thr Arg Leu Arg Arg Leu
                 85                  90                  95

Thr Ala Asp Arg Asp Asp Leu Leu Val Ala Val Leu Glu Glu Val
            100                 105                 110

Ile Tyr Leu Leu Asp Thr Val Gly Glu Thr Pro Val Asp Leu Arg Leu
            115                 120                 125

Arg Asp Val Asp Gly Gly Val Asp Val Thr Phe Ala Thr Thr Asp Ala
            130                 135                 140

Ser Thr Leu Val Gln Val Gly Ala Val Pro Lys Ala Val Ser Leu Asn
145                 150                 155                 160

Glu Leu Arg Phe Ser Gln Gly Arg His Gly Trp Arg Cys Ala Val Thr
                165                 170                 175

Leu Asp Val

<210> SEQ ID NO 43
<211> LENGTH: 136
<212> TYPE: PRT
<213> ORGANISM: Thermotoga maritima
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 43

Xaa Gly Ser Asp Lys Ile His His His His His Xaa Arg Lys Pro
1               5                   10                  15

Ile Glu His Thr Ala Asp Ile Ala Tyr Glu Ile Ser Gly Asn Ser Tyr
                20                  25                  30

Glu Glu Leu Leu Glu Glu Ala Arg Asn Ile Leu Glu Glu Glu Gly
            35                  40                  45

Ile Val Leu Asp Thr Glu Lys Glu Lys Xaa Tyr Pro Leu Glu Glu
50                  55                  60

Thr Glu Asp Ala Phe Phe Asp Thr Val Asn Asp Trp Ile Leu Glu Ile
65                  70                  75                  80

Ser Lys Gly Trp Ala Pro Trp Arg Ile Lys Arg Glu Gly Asn Glu Leu
                85                  90                  95

Lys Val Thr Phe Arg Lys Ile Arg Lys Lys Glu Gly Thr Glu Ile Lys
            100                 105                 110

Ala Leu Thr Tyr His Leu Leu Lys Phe Glu Arg Asp Gly Asp Val Leu
            115                 120                 125

Lys Thr Lys Val Val Phe Asp Thr
130                 135

<210> SEQ ID NO 44
<211> LENGTH: 179
<212> TYPE: PRT
<213> ORGANISM: Homo sapiens

<400> SEQUENCE: 44

Met Lys Gly Gly Ser Arg Val Ser Asn Pro Ala Val Met Ala Gln Glu
1               5                   10                  15

Glu Glu Asp Val Arg Asp Tyr Asn Leu Thr Glu Glu Gln Lys Ala Ile
```

```
                       20                  25                  30

Lys Ala Lys Tyr Pro Pro Val Asn Arg Lys Tyr Glu Tyr Leu Asp His
             35                  40                  45

Thr Ala Asp Val Gln Leu His Ala Trp Gly Asp Thr Leu Glu Glu Ala
         50                  55                  60

Phe Glu Gln Cys Ala Met Ala Met Phe Gly Tyr Met Thr Asp Thr Gly
 65                  70                  75                  80

Thr Val Glu Pro Leu Gln Thr Val Glu Val Thr Gln Gly Asp Asp
                 85                  90                  95

Leu Gln Ser Leu Leu Phe His Phe Leu Asp Glu Trp Leu Tyr Lys Phe
                100                 105                 110

Ser Ala Asp Glu Phe Phe Ile Pro Arg Glu Val Lys Val Leu Ser Ile
            115                 120                 125

Asp Gln Arg Asn Phe Lys Leu Arg Ser Ile Gly Trp Gly Glu Phe
        130                 135                 140

Ser Leu Ser Lys His Pro Gln Gly Thr Glu Val Lys Ala Ile Thr Tyr
145                 150                 155                 160

Ser Ala Met Gln Val Tyr Asn Glu Glu Asn Pro Glu Val Phe Val Ile
                165                 170                 175

Ile Asp Ile

<210> SEQ ID NO 45
<211> LENGTH: 717
<212> TYPE: DNA
<213> ORGANISM: Homo sapiens

<400> SEQUENCE: 45
ccgggccgaa gtccggtgga tgaagggcgg aagtagagtg tctaatcctg cagtcatggc      60
gcaggaagag gaagatgtta gagattacaa tttgactgaa gaacagaagg cgatcaaggc     120
caagtatccg ccagtcaata ggaagtacga gtatttggat catacagcag atgtccagtt     180
acacgcatgg ggagatactc tggaggaagc atttgagcaa tgtgcaatgg ccatgtttgg     240
ttacatgaca gatactggga cagtggagcc cctccaaaca gtagaagtag aaacccaagg     300
agatgactta cagtctcttc tgtttcactt tttggatgaa tggctttata agttcagtgc     360
tgatgaattc ttcataccccc gggaagtgaa agtacttagc attgatcaaa gaaatttcaa     420
attacgatca attgggtggg gagaagaatt ttcattgtcc aagcaccctc agggaacaga     480
agtcaaagca ataacatatt cagcaatgca ggtctataat gaagagaacc cggaagtttt     540
tgtgatcatt gacatttaag acaccaaaaa ataaaagact cctacgaaga actgtttttg     600
ttttcctctt cctttgaga agacactatg aattaaattc tacagctttt ttttgatata     660
tggaaatttg tagaacagaa atattttagt taaagtgtga ctttcagaaa gggaaaa       717

<210> SEQ ID NO 46
<211> LENGTH: 2081
<212> TYPE: DNA
<213> ORGANISM: Homo sapiens

<400> SEQUENCE: 46
gttgctcatc tgctgcggcg ctggtcgcgc ctgcgctttg ttcttggaa ggcggtgctc       60 tgagaagccg gactacgcgg cagcggctct tcaaagcgga gccgggagtt tttgctacag     120
ttttcgccac catgagtcgc agctataatg atgagctgca gttcttggag aagatcaata     180
aaaactgctg gaggatcaag aagggcttcg tgcccaacat gcaggttgaa ggtgtttttct     240
```

```
atgtgaatga tgctctggag aaattgatgt ttgaggaatt aaggaatgcc tgtcgaggtg    300
gtggtgttgg tggcttcctg ccagccatga aacagattgg caatgtggca gccctgcctg    360
gaattgttca tcgatctatt gggcttcctg atgtccattc aggatatggg tttgctattg    420
ggaacatggc agcctttgat atgaatgacc ctgaagcagt agtatcccca ggtggtgtcg    480
ggtttgacat caactgtggt gtccgcttgc taagaaccaa tttagatgaa agtgatgtcc    540
agcctgtgaa ggagcaactt gcccaagcta tgtttgacca cattcctgtt ggggtggggt    600
caaaaggtgt catcccaatg aatgccaaag acttggagga ggccttggag atggggtgg     660
actggtcctt aagagaaggg tatgcctggg ctgaagacaa ggagcactgc gaggagtacg    720
gaaggatgct gcaggctgac cccaataaag tttctgcaag ggcgaagaaa agaggccttc    780
ctcagttggg gaccctggga gcaggcaacc attatgcaga atccaggtt gtggatgaga     840
ttttcaatga gtatgctgct aaaaaaatgg gcatcgacca taagggacag gtgtgtgtga    900
tgatccacag tggaagcaga ggcttgggcc accaagtagc cacagatgcg ctggtagcta    960
tggagaaggc catgaagaga gacaagatta tagtcaatga tcggcagttg gcttgtgctc   1020
gaatcgcttc cccagagggt caagactatc tgaagggaat ggcagctgct gggaactatg   1080
cctgggtcaa ccgctcttcc atgaccttct taacccgtca ggctttcgcc aaggtcttca   1140
acacaacccc tgatgacttg gacctacatg tgatctatga tgtttctcac aacattgcca   1200
aagtggagca gcatgtggtg gacggaaagg aacggacact gttagtacac aggaagggat   1260
ccacccgcgc tttccctcct caccatcccc tcattgctgt tgattaccaa ctcactggac   1320
agccagtgct cattggtggc accatgggaa cctgtagtta tgttcttact ggcactgaac   1380
agggcatgac tgagaccttt ggaacaacct gtcatggagc gggccgtgca ttgtcccgag   1440
caaaatctcg acgtaattta gatttccagg atgtcttaga caaattggca gatatggaa    1500
ttgcgatccg tgttgcctca cccaaactgg ttatggaaga ggctcctgag tcctataaga   1560
atgtgacaga tgtggtaaat acctgccatg atgctggaat cagcaagaaa gccattaaac   1620
tgagaccaat tgctgtgatc aaaggataga accttggaca gcagggctgc ctgacaccac   1680
caaccctctc tgaagtggaa gtggactgac atgctcttct gacatcagac tcaaggcggg   1740
acaagttgca aagtgtgcag ctgtaactgc tcacgccaaa atggctgatg gggaggctgc   1800
tgctttcagg ggcccgtgct tgtaaaataa ccttccagga agaggcacat gcccaccttt   1860
tggaaaggga ggaatatgcc ttctccttgg ttgttccaca gagttttagg aaaatctgtt   1920
agggatgggt agatgtcaaa ctgccttacg cagtcatact gatctttagc catcagattg   1980
atcttcttca caccaagctc tgtttacatt ccgagaggtg tcatgaagaa agttctgttc   2040
aataaggttt tggaatgttt cctttcaaaa aaaaaaaaa a                        2081
```

<210> SEQ ID NO 47
<211> LENGTH: 21
<212> TYPE: DNA
<213> ORGANISM: Artificial Sequence
<220> FEATURE:
<223> OTHER INFORMATION: Synthetic siRNA (sense strand)

<400> SEQUENCE: 47

```
ugacauuuaa gacaccaaat t                                               21
```

<210> SEQ ID NO 48
<211> LENGTH: 21
<212> TYPE: DNA
<213> ORGANISM: Artificial Sequence

```
-continued

<220> FEATURE:
<223> OTHER INFORMATION: Synthetic siRNA (antisense strand)

<400> SEQUENCE: 48
uuuggugucu uaaaugucat t                                              21
```